(12) United States Patent
Studer et al.

(10) Patent No.: US 12,404,489 B2
(45) Date of Patent: Sep. 2, 2025

(54) ESTABLISHING TOPOGRAPHIC ORGANIZATION IN THREE-DIMENSIONAL TISSUE CULTURE

(71) Applicant: MEMORIAL SLOAN-KETTERING CANCER CENTER, New York, NY (US)

(72) Inventors: Lorenz Studer, New York, NY (US); Gustav Cederquist, New York, NY (US)

(73) Assignee: MEMORIAL SLOAN-KETTERING CANCER CENTER, New York, NY (US)

(*) Notice: Subject to any disclaimer, the term of this patent is extended or adjusted under 35 U.S.C. 154(b) by 637 days.

(21) Appl. No.: 16/773,341

(22) Filed: Jan. 27, 2020

(65) Prior Publication Data

US 2020/0239841 A1 Jul. 30, 2020

Related U.S. Application Data

(63) Continuation of application No. PCT/US2018/044296, filed on Jul. 30, 2018.

(60) Provisional application No. 62/538,350, filed on Jul. 28, 2017.

(51) Int. Cl.
*C12N 5/079* (2010.01)
*G01N 33/50* (2006.01)

(52) U.S. Cl.
CPC ....... *C12N 5/0618* (2013.01); *G01N 33/5082* (2013.01); *C12N 2501/15* (2013.01); *C12N 2501/155* (2013.01); *C12N 2501/16* (2013.01); *C12N 2501/41* (2013.01); *C12N 2501/415* (2013.01); *C12N 2503/02* (2013.01); *C12N 2506/02* (2013.01); *C12N 2513/00* (2013.01)

(58) Field of Classification Search
CPC .............. C12N 5/0618; C12N 2501/41; C12N 2513/00; G01N 33/5082
See application file for complete search history.

(56) References Cited

U.S. PATENT DOCUMENTS

| | | | |
|---|---|---|---|
| 2010/0021422 A1* | 1/2010 | Temple | A61K 35/30 424/85.2 |
| 2011/0091869 A1 | 4/2011 | Sasai et al. | |
| 2015/0330970 A1 | 11/2015 | Knoblich et al. | |
| 2016/0289635 A1 | 10/2016 | Sasai et al. | |

(Continued)

FOREIGN PATENT DOCUMENTS

| | | |
|---|---|---|
| EP | 2743345 A1 | 6/2014 |
| WO | WO 2009/131166 A1 | 10/2009 |

(Continued)

OTHER PUBLICATIONS

McGuigan et al. Tissue Patterning: Translating Design Principles from In Vivo to In Vitro. Annu. Rev. Biomed. Eng. 2016.18:1-24. (Year: 2016).*

(Continued)

*Primary Examiner* — Taeyoon Kim
(74) *Attorney, Agent, or Firm* — Baker Botts L.L.P

(57) ABSTRACT

The present disclosure relates to methods and compositions for generating topographically organized tissues in vitro, for the resulting cultured tissue and components thereof, and for uses of such cultured tissue and its components in drug discovery, toxicology studies, and therapy.

17 Claims, 37 Drawing Sheets

(56) References Cited

U.S. PATENT DOCUMENTS

Figure 1:
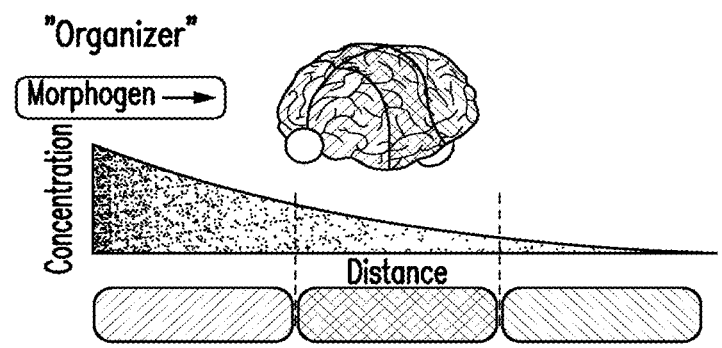

2016/0312181 A1   10/2016  Freed et al.
2019/0367868 A1\*  12/2019  Rubin .................. C12N 5/0619

FOREIGN PATENT DOCUMENTS

| WO | WO 2009/155001 A2 | 12/2009 | |
|----|----|----|----|
| WO | WO 2010/096496 A2 | 8/2010 | |
| WO | WO 2011/149762 A2 | 12/2011 | |
| WO | WO 2013/067362 A1 | 5/2013 | |
| WO | WO 2014/176606 A1 | 10/2014 | |
| WO | WO 2015/076388 A1 | 5/2015 | |
| WO | WO 2015/077648 A1 | 5/2015 | |
| WO | WO 2017/083705 A1 | 5/2017 | |
| WO | WO-2018197544 A1 \* | 11/2018 | ........... C12N 5/0618 |

OTHER PUBLICATIONS

Balaskas et al. Gene Regulatory Logic for Reading the Sonic Hedgehog Signaling Gradient in the Vertebrate Neural Tube. Cell 148, 273-284 (Year: 2012).\*
Giobbe et al. Functional differentiation of human pluripotent stem cells on a chip. Nature Methods. vol. 12, No. 7, p. 637-643 (Year: 2015).\*
Rimkus et al. Targeting the Sonic Hedgehog Signaling Pathway: Review of Smoothened and GLI Inhibitors. Cancers 2016, 8, 22, p. 1-23 (Year: 2016).\*
Hansen et al. Deriving Excitatory Neurons of the Neocortex from Pluripotent Stem Cells. Neuron 70. p. 645-660 (Year: 2011).\*
Gulacsi et al. Shh Maintains Nkx2.1 in the MGE by a Gli3-Independent Mechanism. Cerebral Cortex 2006; 16:189-195 (Year: 2006).\*
Alland et al., "Dual myristylation and palmitylation of Src family member p59$^{fyn}$ affects subcellular localization," *J Biol Chem* 269:16701-16705 (1994).
Bagley et al., "Fused dorsal-ventral cerebral organoids model interactions between diverse brain regions," *Nat Methods*. 14(7):743-751 (2017).
Bellosta et al., "Safety of statins: focus on clinical pharmacokinetics and drug interactions," *Circulation* 109:50-57 (2004).
Berthiaume et al., "Synthesis and use of iodo-fatty acid analogs." *Methods Enzymol* 250:454-466 (1995).
Birey et al., "Assembly of functionally integrated human forebrain spheroids" *Nature* 545:54-59 (2017).
Blaess et al., "Sonic hedgehog signaling in the development of the mouse hypothalamus," *Front Neuroanat* 8:156 (2015).
Blassberg et al., "Reduced cholesterol levels impair Smoothened activation in Smith-Lemli-Opitz syndrome," *Hum Mol Genet* 25:693-705 (2016).
Briscoe et al., "A hedgehog-insensitive form of patched provides evidence for direct long-range morphogen activity of sonic hedgehog in the neural tube," *Mol Cell* 7:1279-1291 (2001).
Briscoe et al., "The mechanisms of Hedgehog signalling and its roles in development and disease," *Nat Rev Mot Cell Biol* 14:416-429 (2013).
Buglino et al., "Hhat is a palmitoylacyltransferase with specificity for N-palmitoylation of Sonic Hedgehog," *J Biol Chem* 283:22076-22088 (2008).
Byrne et al., "Structural basis of Smoothened regulation by its extracellular domains," *Nature* 535:517-522 (2016).
Cai et al., "BMP and TGF-β pathway mediators are critical upstream regulators of Wnt signaling during midbrain dopamine differentiation in human pluripotent stem cells," Dev Biol, Jan. 23, 2013, vol. 376, No. 1, pp. 62-73.
Chambers et al., "Highly efficient neural conversion of human ES and iPS cells by dual inhibition of SMAD signaling," Nature Biotechnology 27:275-280 (2009).
Chambers et al., "Combined small-molecule inhibition accelerates developmental timing and converts human pluripotent stem cells into nociceptors," Nature Biotechnology 30:715-720 (2012).
Chen et al., "Palmitoylation is required for the production of a soluble multimeric Hedgehog protein complex and long-range signaling in vertebrates," *Genes Dev* 18:641-659 (2004).
Chen et al., "Small molecule-mediated disruption of Wnt-dpendent signaling in tissue regeneration and cancer," Nat Chem Biol 5:100-7 (2009).
Chen et al., "Transcripts involved in calcium signaling and telencephalic neuronal fate are altered in induced pluripotent stem cells from bipolar disorder patients," *Transl Psychiatry* 4:e375 (2014).
Clevers, "Modeling Development and Disease with Organoids," Cell 165(7):1586-1597 (2016).
Cobos, I. et al., "Mice lacking *Dlx1* show subtype-specific loss of interneurons, reduced inhibition and epilepsy," *Nat Neurosci* 8:1059-1068 (2005).
Creanga et al., "Scube/You activity mediates release of dually lipid-modified Hedgehog Signal in soluble form," *Genes Dev* 26:1312-1325 (2012).
Cuny et al., "Structure-activity relationship study of bone morphogenetic protein (BMP) signaling inhibitors," Bioorg Med Chem Lett 18:4388-4392 (2008).
Di Lullo et al., The use of brain organoids to investigate neural development and disease. *Nat Rev Neurosci* 18:573-584 (2017).
Edison et al., "Central nervous system and limb anomalies in case reports of first-trimester statin exposure," *N Engl J Med* 350:1579-1582 (2004).
Edison et al., "Mechanistic and epidemiologic considerations in the evaluation of adverse birth outcomes following gestational exposure to statins," *Am J Med Genet* A 131:287-298 (2004).
Eiraku, M. et al., "Self-organizing optic-cup morphogenesis in three-dimensional culture," Nature 472:51-56 (2011).
Ericson, J. et al., "Sonic hedgehog induces the differentiation of ventral forebrain neurons: a common signal for ventral patterning within the neural tube," *Cell* 81:747-756 (1995).
Extended European Search Report dated Mar. 30, 2021 in Application No. EP 18838060.
Fan et al., "Patterning of mammalian somites by surface ectoderm and notochord: evidence for sclerotome induction by a hedgehog homolog," *Cell* 79:1175-1186 (1994).
Fattahi et al., "Deriving human ENS lineages for cell therapy and drug discovery in Hirschsprung disease," *Nature* 531:105-109 (2016).
Fontebasso, A. M. et al., "Recurrent somatic mutations in ACVR1 in pediatric midline high-grade astrocytoma," *Nat Genet* 46:462-466 (2014).
Gaspard et al., "An intrinsic mechanism of corticogenesis from embryonic stem cells," *Nature* 455:351-357 (2008).
Gonzalez, F. et al., "An iCRISPR platform for rapid, multiplexable, and inducible genome editing in human pluripotent stem cells," *Cell Stem Cell* 15:215-226 (2014).
Guerrero et al., "A conserved mechanism of Hedgehog gradient formation by lipid modifications," *Trends Cell Biol* 17:1-5 (2007).
Harfe, B. D. et al., "Evidence for an expansion-based temporal Shh gradient in specifying vertebrate digit identities," *Cell* 118:517-528 (2004).
Hong, M. et al., "BOC is a modifier gene in holoprosencephaly," *Hum Mutat* 38:1464-1470 (2017).
Honig, "Positional signal transmission in the developing chick limb," *Nature* 291:72-73 (1981).
Houart, C. et al., "Establishment of the telencephalon during gastrulation by local antagonism of Wnt signaling," *Neuron* 35:255-265 (2002).
Huang et al., "Tankyrase inhibition stabilizes axin and antagonizes Wnt signaling," *Nature* 461:614-620 (2009).
Huang, P. et al., "Cellular Cholesterol Directly Activates Smoothened in Hedgehog Signaling," *Cell* 166:1176-1187 e1114 (2016).
International Search Report dated Oct. 11, 2018 in International Application No. PCT/US2018/044296.
Jessell "Neuronal specification in the spinal cord: inductive signals and transcriptional codes," *Nat Rev Genet* 1:20-29 (2000).
Jo, J. et al., "Midbrain-like Organoids from Human Pluripotent Stem Cells Contain Functional Dopaminergic and Neuromelanin-Producing Neurons," *Cell Stem Cell* 19:248-257 (2016).

(56) References Cited

OTHER PUBLICATIONS

Kadoshima, T. et al., "Self-organization of axial polarity, inside-out layer pattern, and species-specific progenitor dynamics in human ES cell-derived neocortex," Proc Natl Acad Sci US A 110:20284-20289 (2013).
Kazmin et al.., "Risks of statin use during pregnancy: a systematic review," J Obstet Gynaecol Can 29:906-908 (2007).
Kelava et al., "Stem Cell Models of Human Brain Development," Cell Stem Cell 18:736-748 (2016).
Kiecker et al., "A morphogen gradient of Wnt/beta-catenin signalling regulates anteroposterior neural patterning in Xenopus," Development 128:4189-4201 (2001).
Lancaster et al., "Cerebral organoids model human brain development and microcephaly," Nature, 501(7467):373-379 (2013).
Lancaster et al., "Generation of cerebral organoids from human pluripotent stem cells," Nat Protoc, 9:2329-2340 (2014).
Lancaster et al., "Organogenesis in a dish: Modeling development and disease using organoid technologies," Science 345:1247125 (2014).
Lancaster et al., "Guided self-organization and cortical plate formation in human brain organoids," Nat Biotechnol 35:659-666 (2017).
Lei et al., "Wnt signaling inhibitors regulate the transcriptional response to morphogenetic Shh-Gli signaling in the neural tube," Dev Cell 11:325-337 (2006).
Lewis et al., "Cholesterol modification of sonic hedgehog is required for long-range signaling activity and effective modulation of signaling by Ptc1" Cell 105:599-612 (2001).
Lupo et al., "Mechanisms of ventral patterning in the vertebrate nervous system," Nat Rev Neurosci 7:103-114 (2006).
Mariani et al., "FOXG1-Dependent Dysregulation of GABA/Glutamate Neuron Differentiation in Autism Spectrum Disorders," Cell 162:375-390 (2015).
Maroof et al., "Directed differentiation and functional maturation of cortical interneurons from human embryonic stem cells," Cell Stem Cell 12:559-572 (2013).
McGlinn et al., "Mechanistic insight into how Shh patterns the vertebrate limb," Curr Opin Genet Dev 16:426-432 (2006).
Menendez et al., "Wnt signaling and a Smad pathway blockade direct the differentiation of human pluripotent stem cells to multipotent neural crest cells," Proceedings of The National Academy of Sciences, 108(48):19240-19245 (2011).
Merchan et al., "Comparison of Pretectal Genoarchitectonic Pattern between Quail and Chicken Embryos," Front Neuroanat 5:23 (2011).
Merkle et al., "Generation of neuropeptidergic hypothalamic neurons from human pluripotent stem cells," Development 142:633-643 (2015).
Muguruma et al., "Self-organization of polarized cerebellar tissue in 3D culture of human pluripotent stem cells," Cell Rep 10:537-550 (2015).
Niida et al., "DKK1, a negative regulator of Wnt signaling, is a target of the beta-catenin/TCF pathway," Oncogene 23:8520-8526 (2004).
O'Leary et al., "Area patterning of the mammalian cortex," Neuron 56:252-269 (2007).
Oliver et al., "Six3, a murine homologue of the sine oculis gene, demarcates the most anterior border of the developing neural plate and is expressed during eye development," Development 121:4045-4055 (1995).
Pasca et al., "Functional cortical neurons and astrocytes from human pluripotent stem cells in 3D culture," Nat Methods 12(7):671-678 (2015).
Qian et al., "Brain-Region-Specific Organoids Using Mini-bioreactors for Modeling ZIKV Exposure," Cell 165:1238-1254 (2016).
Quadrato et al., "The promises and challenges of human brain organoids as models of Neuropsychiatric disease," Nat Med 22:1220-1228 (2016).
Renner et al., "Self-organized developmental patterning and differentiation in cerebral organoids," FMBO J36:1316-1329 (2017).
Sagner et al., "Morphogen interpretation: concentration, time, competence, and signaling dynamics," Wiley Interdiscip Rev Dev Biol 6 (2017).
Sanders et al., "Specialized filopodia direct long-range transport of SHH during vertebrate tissue patterning," Nature 497:628-632 (2013).
Sasai et al., "In vitro organogenesis in three dimensions: self-organising stem cells," Development 139:4111-4121 (2012).
Shinya et al., "Zebrafish Dkk1, induced by the pre-MBT Wnt signaling, is secreted from the prechordal plate and patterns the anterior neural plate," Mech Dev 98:3-17 (2000).
Shiraishi et el., "Generation of thalamic neurons from mouse embryonic stem cells," Development 144:1211-1220 (2017).
Suga et al., "Self-formation of functional adenohypophysis in three-dimensional culture," Nature 480:57-62 (2011).
Taguchi et al., "Prenatal exposure to HMG-CoA reductase inhibitors: Effects on fetal and neonatal outcomes," Reprod Toxicol 26:175-177 (2008).
Tian, et al., "Mouse Disp1 is required in sonic hedgehog-expressing cells for paracrine activity of the cholesterol-modified ligand," Development 132:133-142 (2005).
Tukachinsky et al., "Dispatched and scube mediate the efficient secretion of the cholesterol-modified hedgehog ligand," Cell Rep 2:308-320 (2012).
Vaillant et al., "SHH Pathway and Cerebellar Development," Cerebellum, 8(3):291-301 (2009).
Winterfeld et al., "Pregnancy outcome following maternal exposure to statins: a multicentre prospective study," BJOG 120:463-471 (2012).
Wu et al., "Enhanced production of neuroprogenitors, dopaminergic neurons, and identification of target genes by overexpression of sonic hedgehog in human embryonic stem cells," StemCells Dev, 21(5):729-741 (2011).
Xiang et al., "Fusion of Regionally Specified hPSC-Derived Organoids Models Human Brain Development and Interneuron Migration," Cell Stem Cell 21:383-398 (2017).
Yin et al., "Engineering Stem Cell Organoids," Cell Stem Cell, 118(1):25-38 (2016).
Yu et al., "BMP type I receptor inhibition reduces heterotopic ossification," Nat Med., 14:1363-1369 (2008).
Zeng et al., "A freely diffusible form of Sonic hedgehog mediates long-range signaling," Nature 411:716-720 (2001).
Zhang et al., "Differential developmental strategies by Sonic hedgehog in thalamus and hypothalamus," J Chem Neuroanat 75:20-27 (2016).

\* cited by examiner

TOPOGRAPHY IS SPECIFIED BY GRADED MORPHOGEN SIGNALING

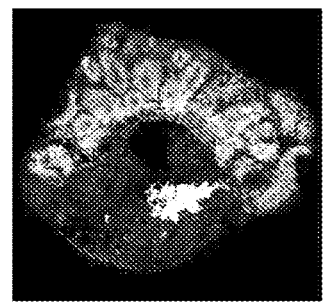
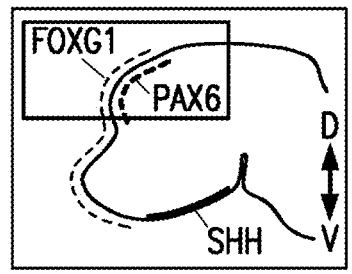
FIG. 7A   FIG. 7B
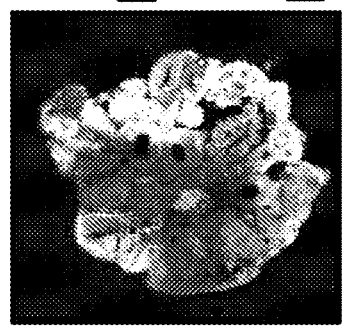
FIG. 8A
FIG. 8B

EYE FIELD DEVELOPMENT

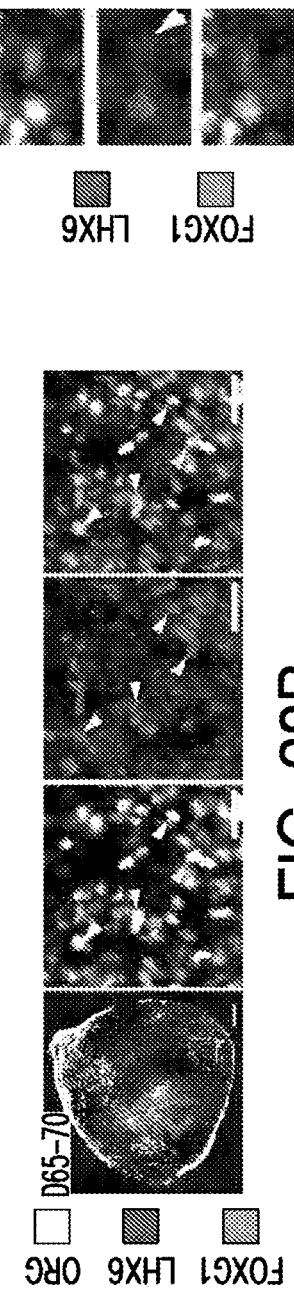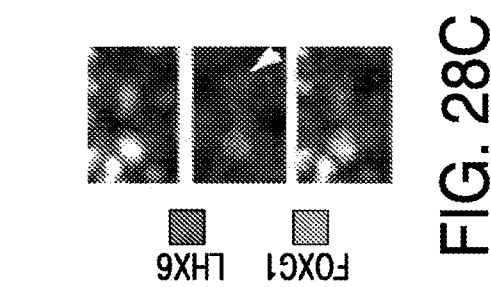
FIG. 28A
FIG. 28B
FIG. 28C

ESTABLISHING TOPOGRAPHIC ORGANIZATION IN THREE-DIMENSIONAL TISSUE CULTURE

CROSS-REFERENCE TO RELATED APPLICATION

This application is a Continuation of International Patent Application No. PCT/US18/44396 filed Jul. 30, 2018, which claims priority to U.S. Provisional Application No. 62/538,350 filed on Jul. 28, 2017, the contents of each of which are incorporated by reference in their entirety, and to each of which priority is claimed.

1. INTRODUCTION

The present disclosure relates to methods and compositions for generating topographically organized tissues in vitro, for the resulting cultured tissue and components thereof, and for uses of such cultured tissue and its components in drug discovery, toxicology studies, and therapy.

2. BACKGROUND OF THE INVENTION

Human pluripotent stem cells (hPSCs) have the intrinsic capacity to self-organize into multicellular organ-like structures called organoids. Brain organoids recapitulate the cellular diversity and micro-architectural features definitive of discrete brain regions, providing unprecedented opportunities to model human brain development and disease. However, in these organoids, discrete brain regions are not ordered with the characteristic anterior-posterior, dorso-ventral, and medio-lateral positioning observed in vivo. The absence of a defined topography is a crucial shortcoming of current brain organoid technologies.

Topographic maps are fundamental organizing features of the human brain that allow for the establishment of precise neuronal connectivity. Topographic maps are established during the earliest stages of development by the graded activity of signaling molecules, which transmit positional information into neural tissue. Signaling molecules are secreted from signaling centers at the edges of presumptive brain regions and establish concentration-dependent and/or time-dependent signaling gradients. The level of signaling activity recorded by each cell assigns its positional identity. In the absence of positional information, neuronal connectivity proceeds in a haphazard fashion, precluding normal brain function.

Sonic Hedgehog (SHH) is a canonical signaling factor that parcellates the mammalian forebrain into distinct functional subdivisions along its dorso-ventral, medio-lateral, and anterior-posterior axes. High levels of SHH signaling promote ventral, medial, or posterior positional identities, whereas lower levels of SHH signaling permit the emergence of dorsal, lateral, or anterior fates. In the absence of SHH signaling, dorsal forebrain identities such as the cortex expand ventrally into the ganglionic eminences. In humans, mutations in the SHH signaling pathway result in holoprosencephaly, a structural brain disorder in which midline structures are absent. Thus, the graded, asymmetric activity of SHH signaling specifies and organizes the functional topography of the forebrain along all three body axes.

In contrast to the graded signaling activity observed in vivo, protocols used heretofore to generate organoids employ signaling activity that is uniformly distributed throughout the tissue. These protocols can largely be classified into two categories: growth factor dependent or growth factor independent. Growth factor dependent protocols utilize bath-applied soluble proteins and small molecules to restrict tissue identity to specified sub-regions of the brain including the retina, cerebral cortex, ventral forebrain, hypothalamus, and midbrain. Growth factor independent protocols rely on intrinsic signaling to spontaneously direct differentiation into various brain tissues. In either case, the developing organoid tissue is not subject to a symmetry-breaking event, such as the graded, asymmetric signaling activity of SHH in vivo, which can specify the three body axes.

3. SUMMARY OF THE INVENTION

The present invention relates to topographically organized tissues generated from precursor cells in vitro. It is based, at least in part, on the discovery that application of an artificially created protein gradient can be used to promote topographic organization in three-dimensional tissue culture, and, in particular, that application of a concentration gradient of Sonic Hedgehog ("SHH") protein may be used to promote topographic organization of differentiating human embryonic stem cells to generate brain organoids having distinct sub-regions organized in their appropriate anatomical positions.

In one aspect, the present disclosure provides a method of producing a topographically organized brain organoid comprising: (i) providing an organizer that is a source of a diffusible organizing agent; (ii) placing the organizer in apposition to an aggregate of undifferentiated or partially differentiated stem cells to form an organizer/aggregate complex; and (iii) culturing the organizer/aggregate complex in vitro under conditions that promote the differentiation of the cells in the aggregate and the formation of the brain organoid, wherein the organizer releases the organizing agent to form a gradient concentration of the organizing agent effective in generating cells, in the organoid, having different phenotypes at different distances from the organizer.

In certain embodiments, the (iii) further comprises contacting the organizer/aggregate complex with at least one inhibitor selected from the group consisting of bone morphogenetic protein (BMP) inhibitors, transforming growth factor beta (TGFβ)/Activin-Nodal inhibitors, and Wingless (Wnt) inhibitors. In certain embodiments, the at least one inhibitor promotes the formation of forebrain tissue. In certain embodiments, the (iii) further comprises contacting the organizer/aggregate complex with at least one BMP inhibitor, at least one TGFβ/Activin-Nodal inhibitor, and at least one Wnt inhibitor. In certain embodiments, the method further comprises contacting the organizer/aggregate complex with the at least one BMP inhibitor, the at least one TGFβ/Activin-Nodal inhibitor, and the at least one Wnt inhibitor concurrently.

In certain embodiments, the organizer/aggregate complex is contacted with the at least one inhibitor for up to about 6, about 7, or about 8 days. In certain embodiments, the at least one BMP inhibitor comprises LDN193189. In certain embodiments, the at least one TGFβ/Activin-Nodal inhibitor comprises SB432542. In certain embodiments, the at least one Wnt inhibitor comprises XAV939.

In certain embodiments, the stem cells are human stem cells. In certain embodiments, the stem cells are selected from the group consisting of embryonic stem cells (ESCs), induced pluripotent stem cells (iPSCs), and combinations thereof. In certain embodiments, the organizer comprises one or more genetically modified cells that express the organizing agent. In certain embodiments, the genetically modified cells are selected from the group consisting of ESCs, iPSCs, and combinations thereof. In certain embodiments, the organizing agent is induciblely expressed or conditionally expressed.

In certain embodiments, the organizer comprises one or more beads that release the organizing agent in a sustainable form. In certain embodiments, the organizing agent is a Sonic Hedgehog Protein (SHH). In certain embodiments, the organizing agent is a human SHH (hSHH).

In certain embodiments, the organizing agent is selected from the group consisting of SHH protein agonists, molecules that induce SHH protein expression, molecules that promote SHH activity, and combinations thereof. In certain embodiments, the organizer is localized at a pole of the organoid.

In certain embodiments, the method further comprises culturing the organizer/aggregate complex in vitro for at least about 20 days to form the topographically organized brain organoid.

In another aspect, the present disclosure provides a method of producing a topically organized brain organoid comprising: (i) providing an organizer comprised of human stem cells engineered to express a hSHH; (ii) placing the organizer in apposition to an aggregate of undifferentiated or partially differentiated pluripotent human stem cells to form an organizer/aggregate complex having the organizer at one pole of the aggregate, wherein the aggregate has a spheroid shape; and (iii) culturing the organizer/aggregate complex in vitro under conditions that promote the differentiation of the cells in the aggregate and the formation of the brain organoid, wherein the organizer releases the hSHH to form a gradient concentration of the hSHH effective in generating the brain organoid comprising at least distinct forebrain and posterior regions.

In certain embodiments, the (iii) further comprises contacting the organizer/aggregate complex with at least one inhibitor selected from the group consisting of bone morphogenetic protein (BMP) inhibitors, transforming growth factor beta (TGFβ)/Activin-Nodal inhibitors, and Wingless (Wnt) inhibitors. In certain embodiments, the at least one inhibitor promotes the formation of forebrain tissues. In certain embodiments, the (iii) further comprises contacting the organizer/aggregate complex with the at least one BMP inhibitor, the at least one TGFβ/Activin-Nodal inhibitor, and the at least one Wnt inhibitor. In certain embodiments, the method further comprises contacting the organizer/aggregate complex with the at least one BMP inhibitor, the at least one TGFβ/Activin-Nodal inhibitor, and the at least one Wnt inhibitor concurrently. In certain embodiments, the organizer/aggregate complex is contacted with the at least one inhibitor for up to about 6, about 7, or about 8 days. In certain embodiments, the at least one BMP inhibitor comprises LDN193189. In certain embodiments, the at least one TGFβ/Activin-Nodal inhibitor comprises SB432542. In certain embodiments, the at least one Wnt inhibitor comprises XAV939.

In certain embodiments, the genetically modified human stem cells are selected from the group consisting of ESCs, iPSCs, and combinations thereof. In certain embodiments, the hSHH is induciblely expressed or conditionally expressed.

In certain embodiments, the method further comprises culturing the organizer/aggregate complex in vitro for at least about 20 days to form the topographically organized brain organoid. In yet another aspect, the present disclosure provides a composition comprising a brain organoid, wherein the brain organoid is prepared from an organizer/aggregate complex by culturing said organizer/aggregate complex in vitro under conditions that promote the differentiation of the cells in the aggregate and the formation of the brain organoid, wherein the organizer/aggregate complex comprises an organizer that is a source of a diffusible organizing agent, and an aggregate of undifferentiated or partially differentiated stem cells, wherein the organizer is placed in apposition to the aggregate to form the organizer/aggregate complex; wherein the brain organoid comprises cells having different phenotypes at different distances from the organizer.

In certain embodiments, the organizer/aggregate complex is contacted with at least one inhibitor selected from the group consisting of bone morphogenetic protein (BMP) inhibitors, transforming growth factor beta (TGFβ)/Activin-Nodal inhibitors, and Wingless (Wnt) inhibitors. In certain embodiments, the organizer/aggregate complex is contacted with the at least one inhibitor for up to about 6, about 7, or about 8 days.

In certain embodiments, the at least one BMP inhibitor comprises LDN193189. In certain embodiments, the at least one TGFβ/Activin-Nodal inhibitor comprises SB432542. In certain embodiments, the at least one Wnt inhibitor comprises XAV939.

In certain embodiments, the stem cells are selected from the group consisting of embryonic stem cells (ESCs), induced pluripotent stem cells (iPSCs), and combinations thereof. In certain embodiments, the organizer comprises one or more genetically modified cells that express the organizing agent.

In certain embodiments, the genetically modified cells are selected from the group consisting of ESCs, iPSCs, and combinations thereof. In certain embodiments, the organizing agent is induciblely expressed or conditionally expressed.

In certain embodiments, the organizer comprises one or more beads that release the organizing agent in a sustainable form. In certain embodiments, the organizing agent is a SHH. In certain embodiments, the organizing agent is a hSHH. In certain embodiments, the organizing agent is selected from the group consisting of SHH protein agonists, molecules that induce SHH protein expression, molecules that promote SHH activity, and combinations thereof.

In certain embodiments, the organizer is localized at a pole of the organoid.

In certain embodiments, the organizer/aggregate complex is cultured in vitro for at least about 20 days to form the brain organoid.

In certain embodiments, the brain organoid comprises at least one region selected from the group consisting of regions having characteristics of the cerebral cortex, regions having characteristics of the hippocampus, regions having characteristics of the lateral ganglionic eminence ("LGE"), regions having characteristics of the medial ganglionic eminence ("MGE"), and regions having characteristics of the hypothalamus ("HtH").

In certain embodiments, the regions having characteristics of the HtH comprise a region having characteristics of the anterior hypothalamic and a region having characteristic of the ventro-posterior hypothalamic.

In certain embodiments, the brain organoid comprises: (i) a demarcated cortex-like region comprising cells expressing FOXG1 and/or PAX6; (ii) a demarcated LGE-like region comprising cells expressing GSH2 and contiguous to a region expressing PAX6; (iii) a demarcated MGE-like region comprising cells expressing NKX2.1 and FOXG1;

(iv) a demarcated hypothalamus-like region comprising cells expressing NKX2.2 and NKX2.1; (v) a demarcated anterior hypothalamic-like region comprising cells expressing NKX2.2; and/or (vi) a demarcated ventro-posterior hypothalamic-like region comprising cells expressing NKX2.1 but not FOXG1.

In another aspect, the present disclosure provides a plurality of cells prepared from the brain organoid as disclosed herein, wherein the cells comprise: (i) a plurality of cells expressing FOXG1 and/or PAX6; (ii) a plurality of cells expressing GSH2; (iii) a plurality of cells expressing NKX2.1 and FOXG1; (iv) a plurality of cells expressing NKX2.2 and NKX2.1; (v) a plurality of cells expressing NKX2.2; and/or (vi) a plurality of cells expressing NKX2.1 but not FOXG1.

In another aspect, the present disclosure provides a method for identification of the toxicity of a drug, comprising: providing a composition comprising an organizer/aggregate complex, wherein the organizer/aggregate complex comprises an organizer that is a source of a diffusible organizing agent, and an aggregate of undifferentiated or partially differentiated stem cells, wherein the organizer is apposition the aggregate to form the organizer/aggregate complex; contacting the composition with the drug; culturing the organizer/aggregate complex in vitro under conditions that promote the differentiation of the cells in the aggregate and the formation of the brain organoid; and evaluating the patterning and/or growth of the brain organoid.

4. BRIEF DESCRIPTION OF THE FIGURES

FIG. 1. Schematic of relationship between concentration of morphogen (referred to as "organizing agent" herein) and topology of differentiated brain tissue.

Figure 2A:
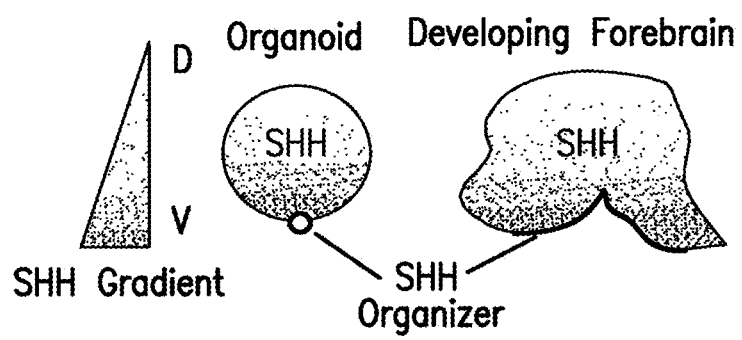
Figure 2B:
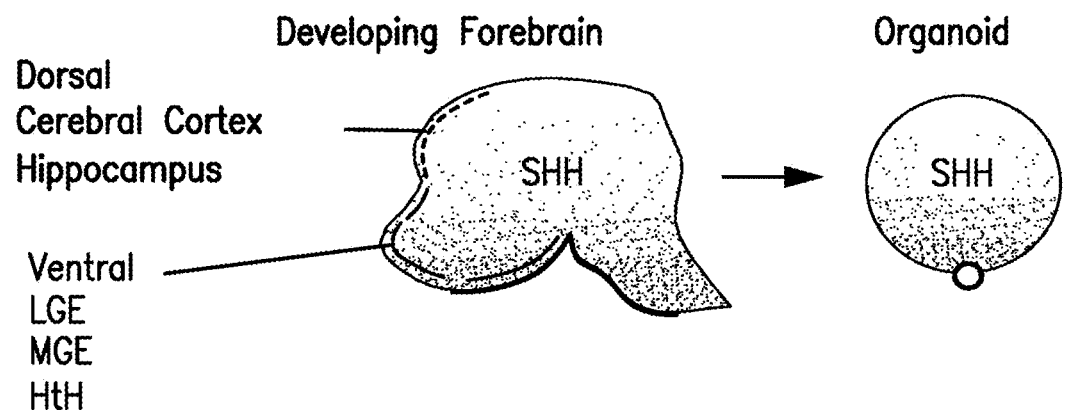

FIGS. 2A-2B. (A) Schematic shows the ventral (V) to dorsal (D) SHH concentration gradient in brain tissue, shown in sagittal view (rightmost figure), where organizer appears as a thick dark gray line, and in organoid (middle figure), where organizer appears as a dark gray circle. (B) Strategy to organize sub-regions within the brain organoid into discrete and invariant positional domains. Brain regions of interest are indicated on the sagittal section of developing forebrain: Dorsal Region including the cerebral cortex and hippocampus and Ventral Region including the lateral ganglionic eminence ("LGE"), medial ganglionic eminence ("MGE") and hypothalamus-like domains ("HtH").

Figure 3A:
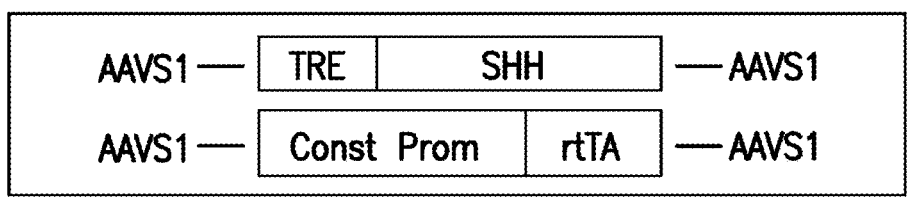
Figure 3B:
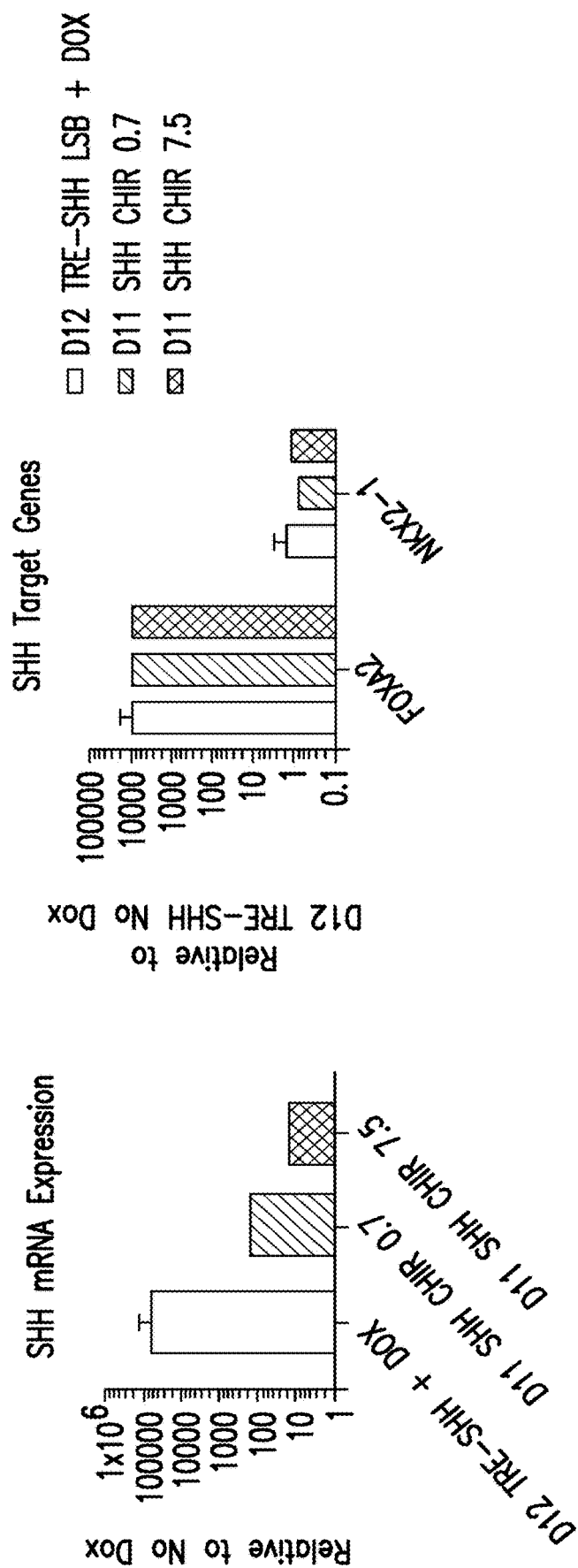

FIGS. 3A-3B. Construction and function of SHH organizer tissue. (A) Schematic of genome targeting strategy to create an hESC line that expresses SHH under the control of doxycycline. (B) SHH expression in engineered hESC cell line (left panel) and expression of target gene FOXA2 in response to induced SHH (right panel).

Figure 4:
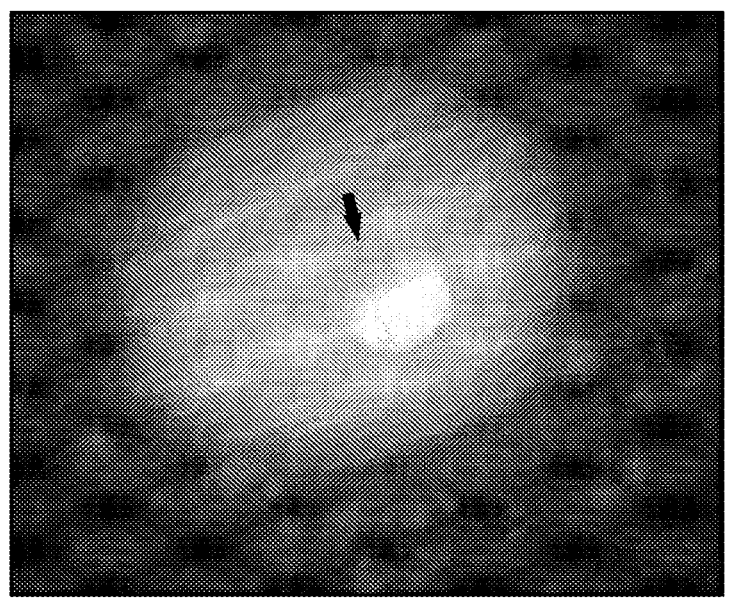

FIG. 4. Fluorescent micrograph of an hESC spheroid in which organizer tissue (white arrow) has been embedded at one pole of the spheroid.

Figure 5:
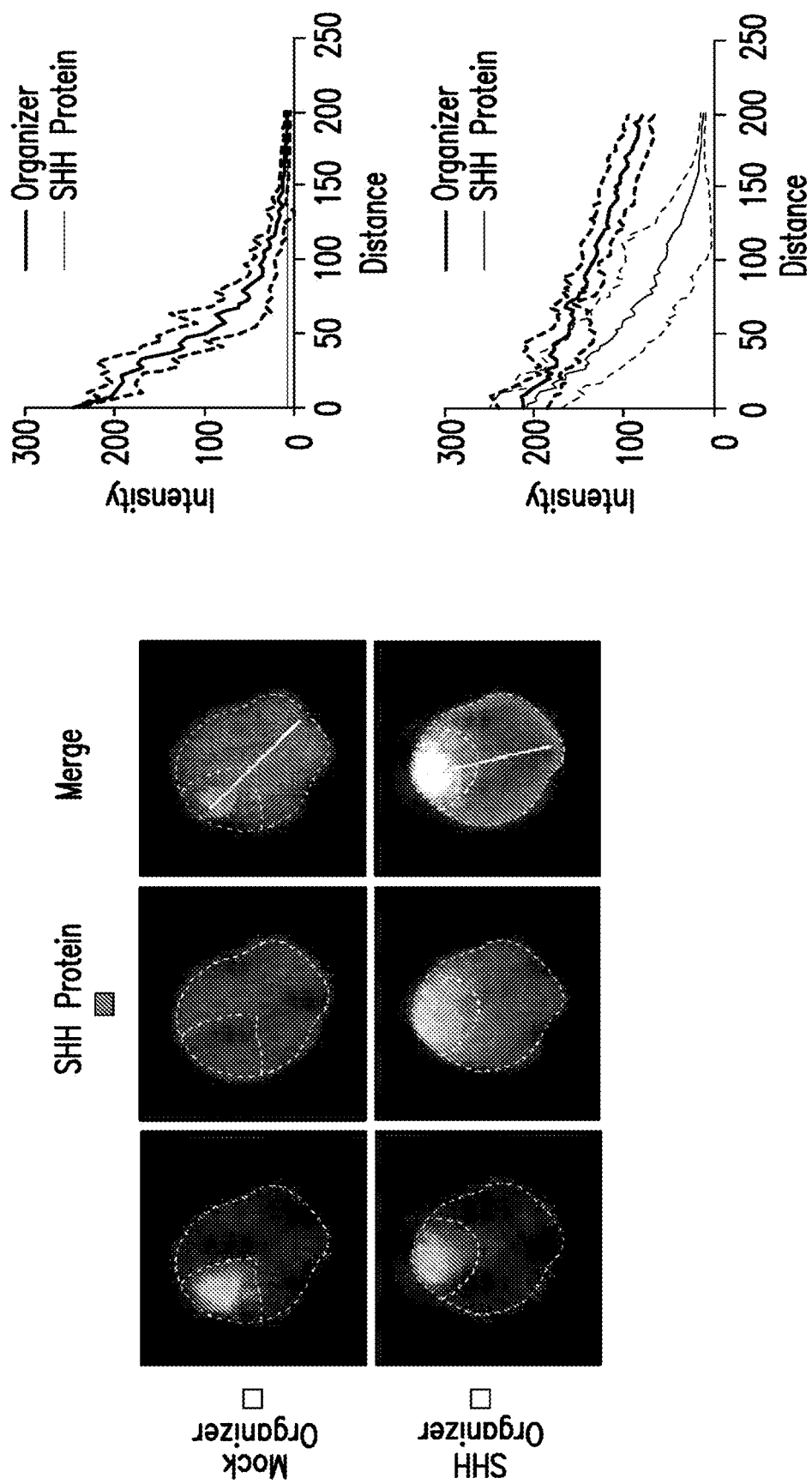

FIG. 5. Establishment of protein gradient in brain organoids; comparison of SHH levels in organoids containing a mock organizer (top panels) versus a SHH-expressing and secreting organizer (bottom panels), showing establishment of a gradient in the latter.

Figure 6A:
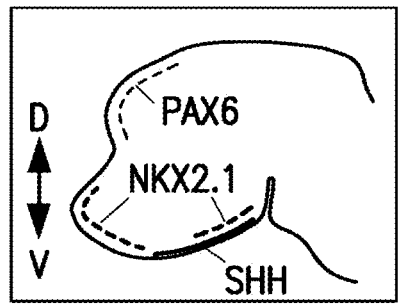
Figure 6B:
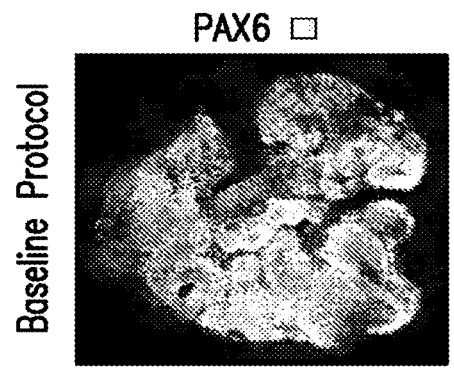
Figure 6C:
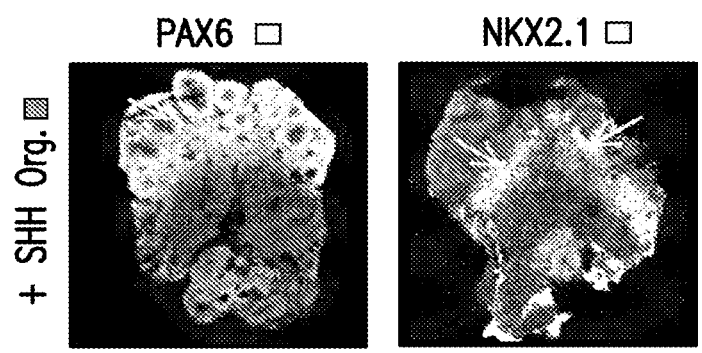

FIGS. 6A-6C. SHH organizer organizes dorsal versus ventral domains. (A) Location of PAX6 (dorsal) and NKX2.1 (ventral) expression. (B) Immunofluorescent staining showing expression of PAX6 throughout the entire organoid in the absence of organizer. (C) Immunofluorescence staining showing expression (indicated by arrows) of PAX6 (left panel) and NKX2.1 (right panel) in organoids having an organizer (adjacent to white asterisk).

FIGS. 7A-7B. (A) Immunofluorescence staining of PAX6 and FOXG1 co-expression (white arrow) in organoids with SHH-organizer (adjacent to white asterisk). (B) In the brain's cerebral cortex, PAX6 and FOXG1 are expressed in a region distal from SHH-expressing tissue.

FIGS. 8A-8B. SHH organoids contain lateral ganglionic eminence (LGE) territory. (A) The LGE expresses GSH2 and is continuous with PAX6-expressing cerebral cortex. SHH-organizer is marked with a white asterisk. (B) Immunofluorescence staining showing that in SHH organoids, the GSH2 territory is also continuous with the PAX6 territory.

Figure 9A:
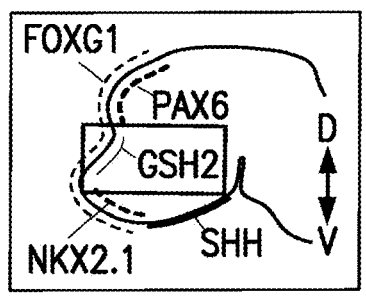
Figure 9B:

FIGS. 9A-9B. (A) The medial ganglionic eminence (MGE) is a brain region that expresses NKX2.1 and FOXG1. The MGE is in the most ventral domain of FOXG1 expression in vivo. (B) In SHH organoids, the MGE territory is also in the most ventral FOXG1 territory (see, e.g. white circled area). SHH-organizer is marked with a white asterisk.

Figure 10A:
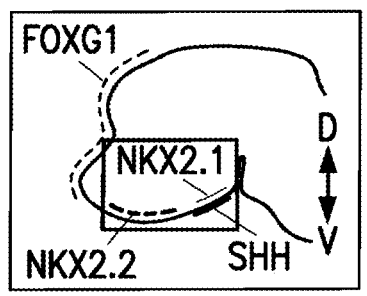
Figure 10B:
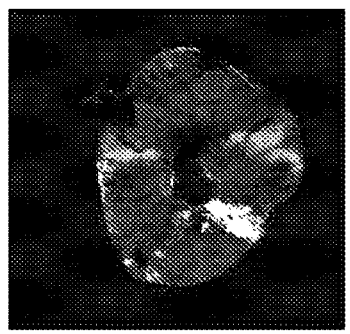
Figure 10B:
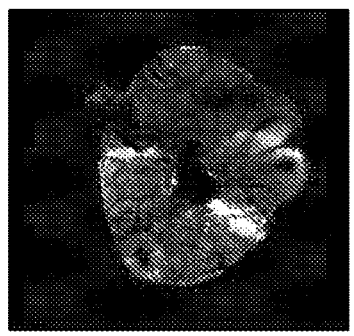

FIGS. 10A-10B. (A) The hypothalamus (HtH) in the brain expresses NKX2.2 and NKX2.1. The HtH is located proximal to, and overlapping with the source of SHH protein (adjacent to white asterisk) in the brain. (B) This distribution is mirrored in SHH organoids, indicating proper topographic organization.

Figures 11A, 11B, 11C:
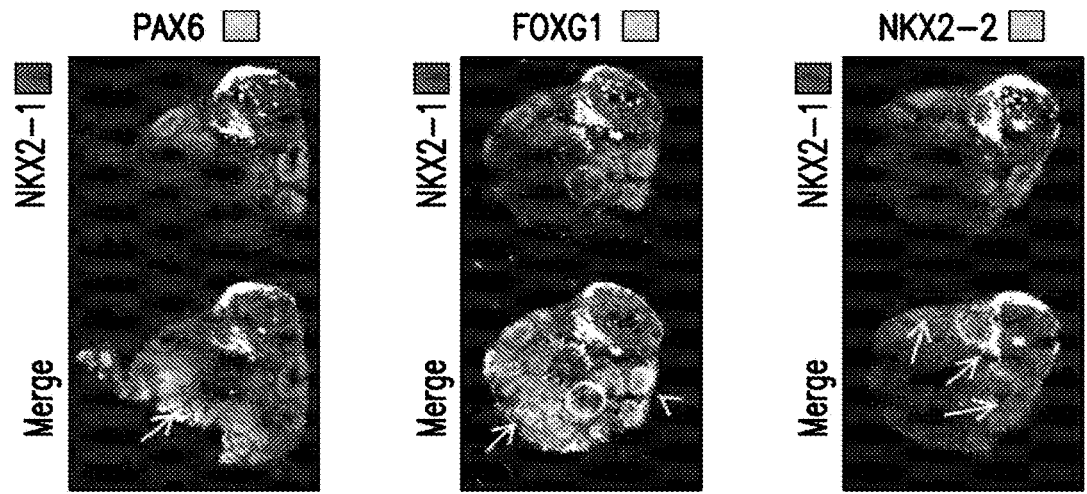

FIGS. 11A-11C. Immunofluorescent staining showing expression of SHH (dotted arrow), PAX6 (A, white arrow), FOXG1 alone (B, white arrow), FOXG1 co-expressed with NKX2-1 (white arrowhead), NKX2-2 (C, three white arrows) and NKX2-1, in the correct anatomical positioning.

Figure 12:
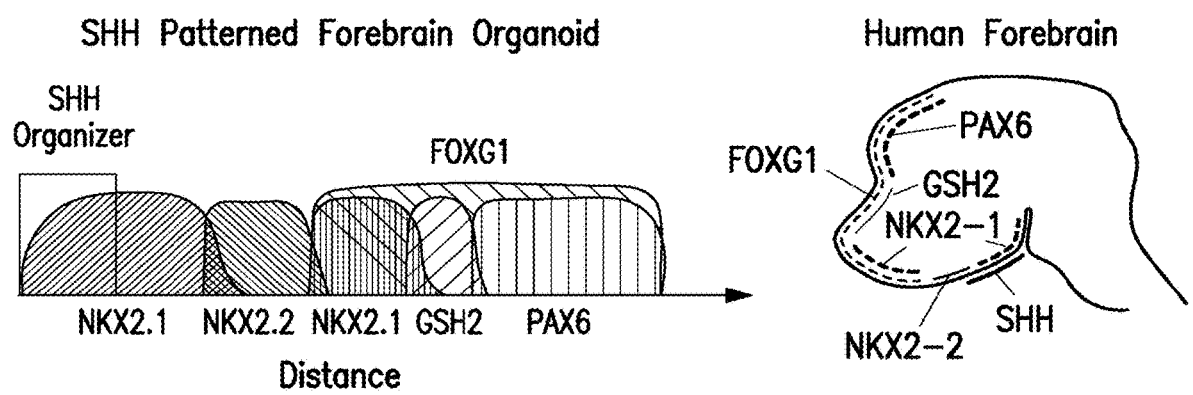

FIG. 12. Summary of observed topography in SHH-organizer containing organoids.

Figure 13:
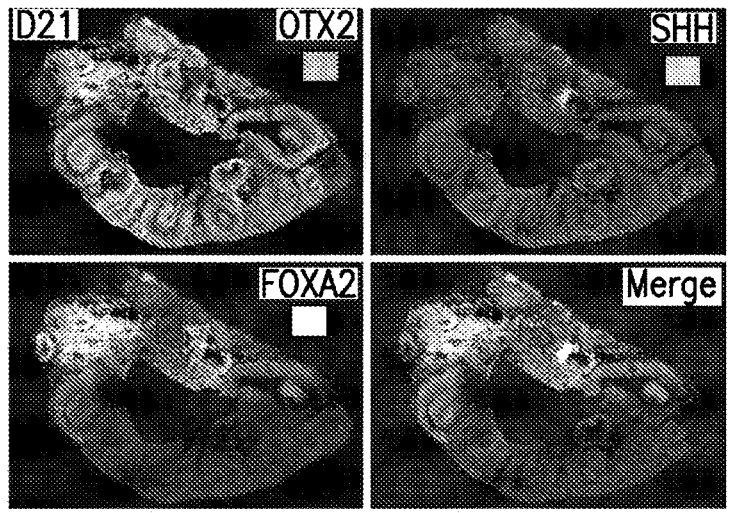

FIG. 13. Immunofluorescent staining showing expression of OTX2, SHH, and FOXA2 in SHH organizer-containing organoids grown in the absence of WNT-inhibitor.

Figure 14:
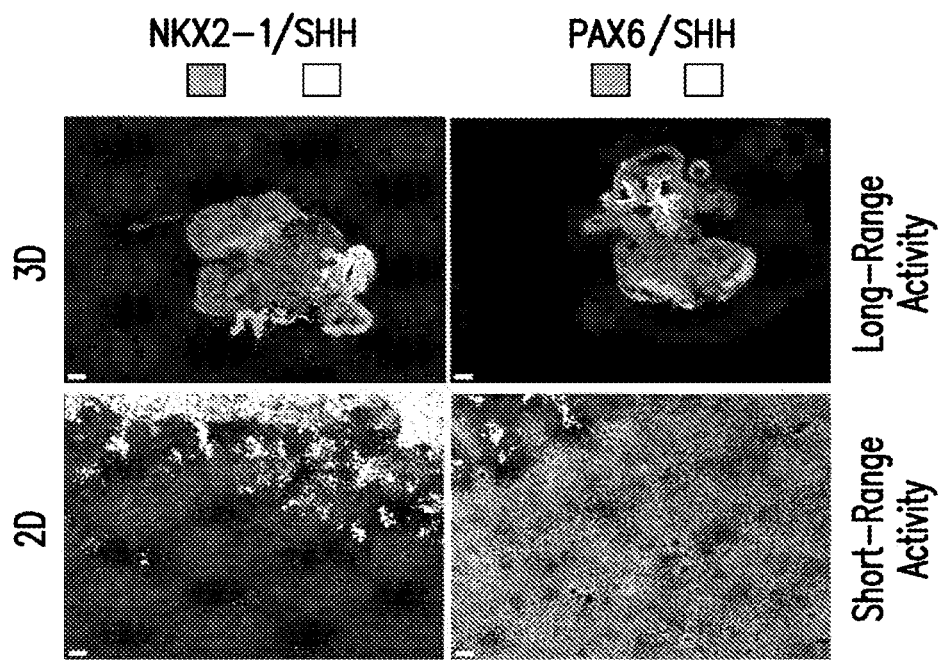

FIG. 14. Short and long-range activity of SHH in SHH organizer-containing organoids (top row) and SHH organizer-containing monolayer, adherent cultures (bottom row).

Figure 15:
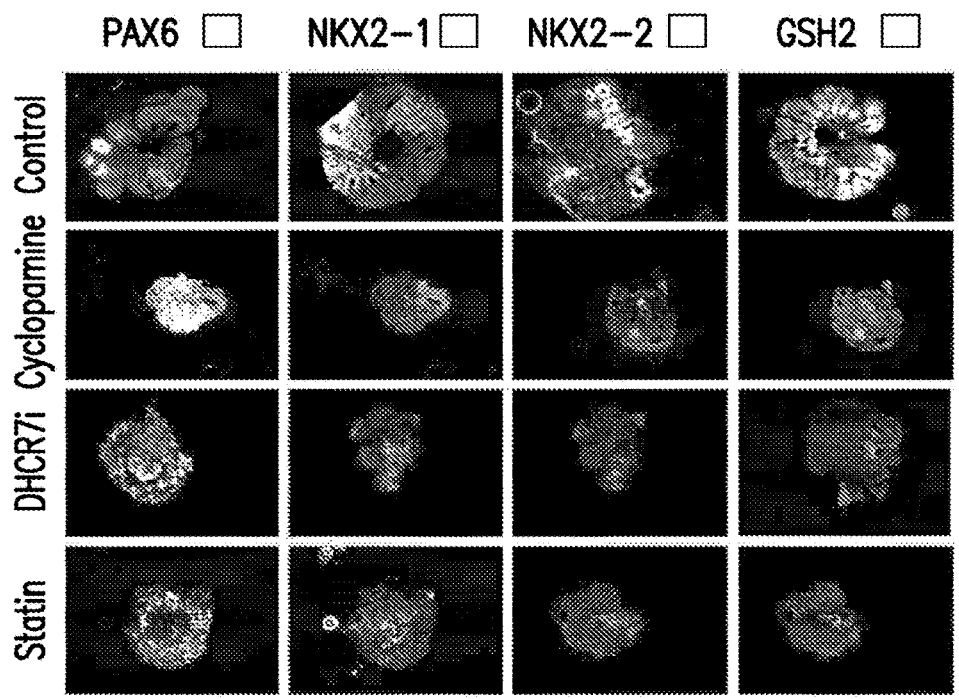

FIG. 15. Effects of statins and other cholesterol inhibitors on development in SHH organizer-containing organoids.

Figure 16:
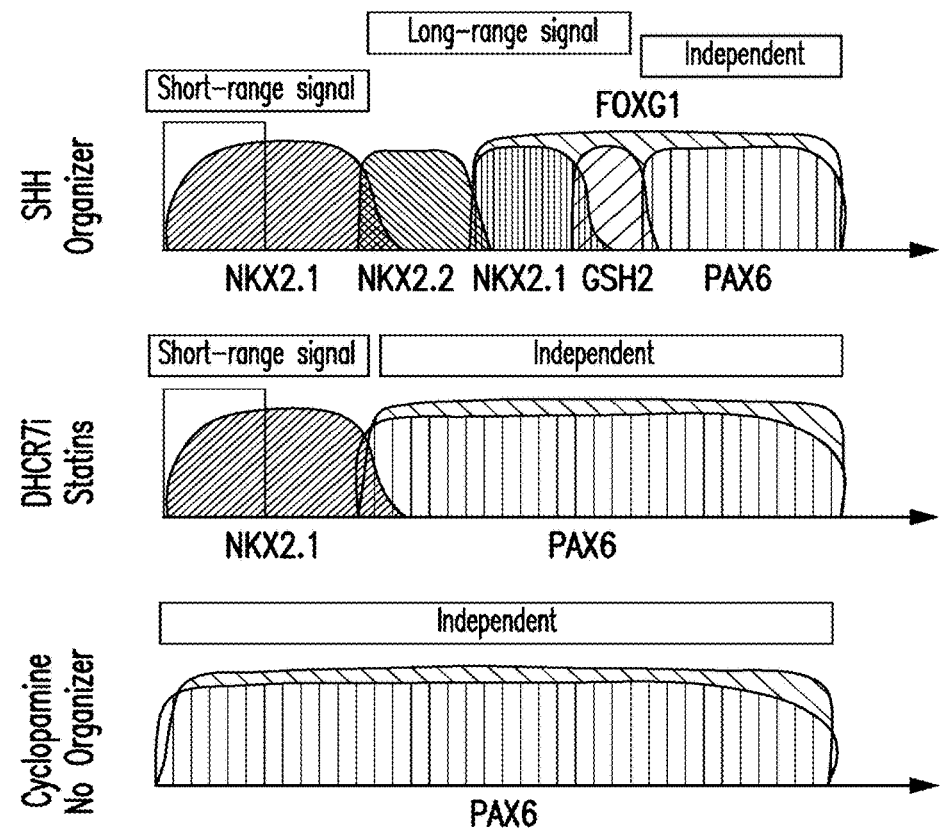

FIG. 16. Summary of the effects of cholesterol inhibition on SHH organizer-containing organoids.

Figure 17:
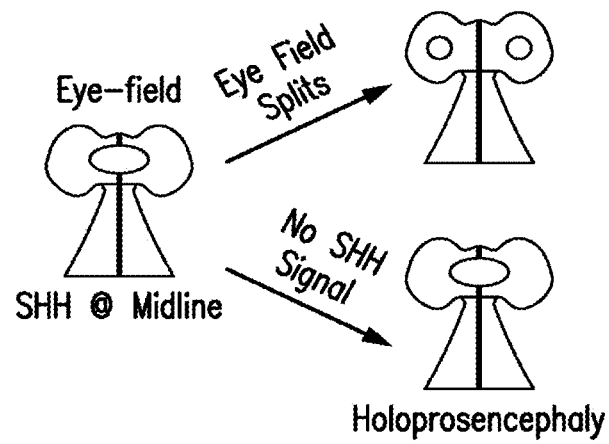

FIG. 17. Effect of SHH on eye field development.

Figure 18:
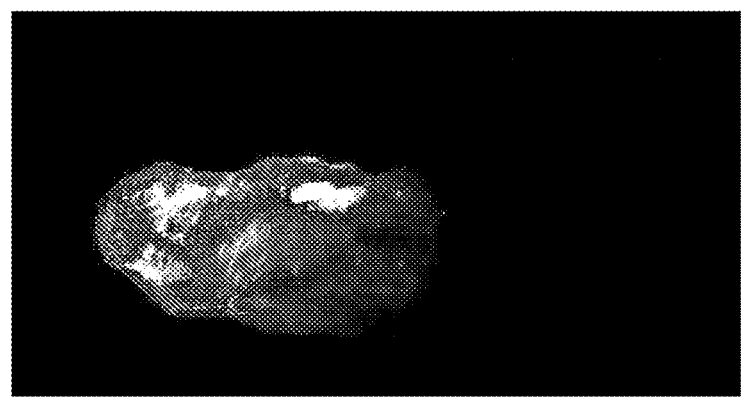

FIG. 18. Wholemount immunofluorescent staining of eye field development in SHH organizer-containing organoid with organizer positioned at midline, showing expression of SHH (dark gray) and CHX10 (light gray).

FIGS. 19A-19J. Establishment of dorso-ventral and antero-posterior developmental axes in SHH organoids. (A) Strategy to specify positional identity in forebrain organoids. SHH exhibits a ventral-high to dorsal-low gradient in the developing forebrain. A doxycycline-inducible SHH (iSHH) hPSC line was engineered using TALEN-mediated homologous recombination. The iSHH line could be positioned at one pole of developing forebrain organoids. (B) qRT-PCR analysis shows robust and titratable induction of SHH transcript expression in iSHH but not H9 hPSC line. Individual replicates plotted on bar graphs, mean±S.D. One-way ANOVA with Dunnett Test. * P=0.0003, P=0.0001. N=3 for each iSHH condition, N=4 for each H9 condition. (C) qRT-PCR analysis of SHH and FOXA2, a SHH target gene, during neural differentiation shows that iSHH expresses biologically active protein, comparable to levels from hPSC-derived floorplate. Individual replicates plotted on bar graphs, mean±S.D. One-way ANOVA with Dunnett Test. *P<0.001, P<0.01. N=3 differentiations for all conditions. (D) Schematic of the method for generating forebrain organoids with a SHH protein gradient. Timeline and small molecules used for neural induction are shown. The specific timing of matrigel embedding can exhibit slight variation among differentiations. (E) Visualization of SHH protein gradient using tyramide signal amplification (TSA). A line scan was used to quantify SHH protein signal. Graph shows mean±95% confidence interval. Intensity of SHH signal (y-axis, green) normalized to maximum iSHH fluorescence. Origin (X-axis) set to position of maximum iSHH fluorescence. (F) Quantification of the distance at which the iSHH-organizer signal (ORG) and SHH protein signal (SHH) reach 25% of maximum intensity demonstrates that the SHH protein gradient extends beyond the limit of the organizer cells. Student two-tailed t-test. N=6 spheroids, 2 batches. (G) Schematic illustrating that PAX6 and NKX2.1 define dorsal and ventral forebrain, respectively. H9 organoids (H9) or SHH-organoids grown without doxycycline (−DOX) largely express PAX6 without detectable NKX2.1 expression, indicating dorsal identity. SHH-organoids grown in the presence of doxycycline (400 ng/ml, +DOX) suppress PAX6 and induce NKX2.1 near the iSHH organizer, indicating induction of ventral identity. Representative images are shown. H9, N=7 organoids; −DOX, N=8 organoids; SHH+Dox, N=11 organoids. Samples are from at least 2 batches. (H) Schematic illustrating that FOXG1 and OTX2 define anterior and posterior forebrain domains. H9 organoids (H9) or SHH-organoids grown without doxycycline (−DOX) largely express FOXG1 with only small amounts of OTX2 expression, indicating predominant telencephalic (anterior forebrain) identity. SHH-organoids grown in the presence of doxycycline (400 ng/ml, +DOX) suppress FOXG1 and induce OTX2 near the iSHH organizer, indicating induction of diencephalic (posterior forebrain) identity. Representative images are shown. H9, N=8 organoids; −DOX, N=8 organoids; +DOX, N=12 organoids. Samples are from at least 2 batches. (I) Schematic illustrating that TCF7L2 and SIX3 define diencephalic and hypothalamic domains. SHH-organoids grown without doxycycline (−DOX) show minimal TCF7L2 and lack SIX3 expression. TCF7L2 and SIX3 are expressed in the presence of doxycycline (400ng/ml, +DOX) close to RFP+iSHH organizer. (J) Dose-dependent activation of DKK1 by SHH. DKK1 is a secreted antagonist of the WNT pathway that helps to establish anterior-posterior WNT patterning activity. N=6-8 for each dose, organoids from two batches. Individual replicates plotted on bar graphs, mean±S.D. One-way ANOVA, P<0.0001, with Dunnett Test.  P<0.0001, P<0.01. Scale Bars: 200 µm.

FIGS. 20A-20E. In vivo-like topographic organization of major forebrain subdivisions in SHH-organoids. (A) In situ hybridization images depicting forebrain topography. The neocortex co-expresses FOXG1 (blue) and PAX6 (green) and is located distal to the SHH source (red). The lateral ganglionic eminence (LGE) co-expresses FOXG1 and GSH2 (orange) and is just ventral to the neocortex. The medial ganglionic eminence (MGE) co-expresses FOXG1 and NKX2.1 (light purple) and is just ventral to the LGE. NKX2.1 is also expressed in the ventro-posterior hypothalamus (dark purple) and is distinguished from the MGE by exclusion of FOXG1 expression. The anterior hypothalamus expresses NKX2.2 (cyan) and resides in the gap between MGE and Hypothalamic NKX2.1 expression. SHH (red) is strongly expressed in the ventro-posterior hypothalamus and is also weakly expressed in the ventral MGE. Images are from © 2008 Allen Institute for Brain Science. Allen Developing Mouse Brain Atlas. Available from developingmouse-.brain-map.org. (B) Quantification of position of regional domains in SHH organoids (400 ng/ml doxycycline). Immunofluorescent signals of each regional marker are plotted as a function of distance from the iSHH organizer (see methods and Supplementary FIG. 2 for details of quantification). Mean±S.E.M. N=30 organoids from 6 batches. (C) Sections from a single organoid showing that SHH-organoids develop with in vivo-like topography. A neocortex-like domain that co-expresses FOXG1 and PAX6 is distal to the SHH organizer (red). A GSH2 domain is observed partially overlapping with and adjacent to the PAX6 domain. A FOXG1/NKX2.1 co-expression domain occupies an intermediate position between the neocortex-like domain and the SHH organizer. Finally, NKX2.2 and NKX2.1 are expressed in the FOXG1 negative territory, with NKX2.1 most proximal to the SHH organizer. Colors of arrowheads correspond to regional identities in panel 2a and delineate presumptive forebrain domains. (D) SHH-organoids grown without doxycycline treatment mainly express FOXG1 (N=6 organoids, 2 batches) and PAX6 (N=6 organoids, 2 batches), with some GSH2 expression (N=9 organoids, 3 batches). No NKX2.1 or NKX2.2 is observed (N=10 organoids, 3 batches). (E) The length of ZO-1+ apical neuroepithelia differs between PAX6+ and NKX2.1+ regions. PAX6+ regions contain circular, rosette-like neuroepithelia, while NKX2.1+ regions contain highly-extended neuroepithelia. High-magnification images correspond to insets. Quantification shows average neuroepithelium length in PAX6 versus NKX2.1 domains. Dots represent individual organoids. Student two-tailed t-test. N=7 organoids, 2 batches for each condition. Scale bars: 200 µm (Low magnification), 50 µm (High magnification).

Figure 21A:
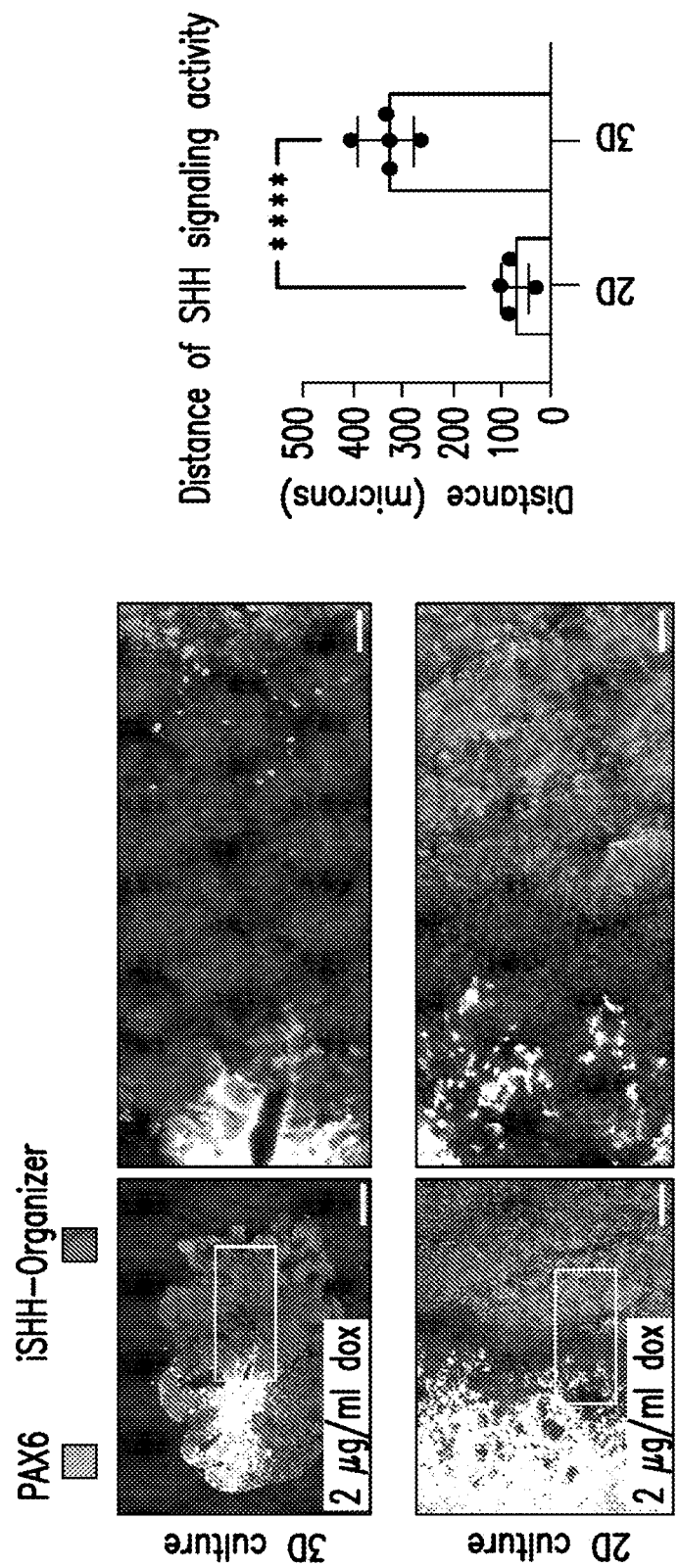
Figure 21B:
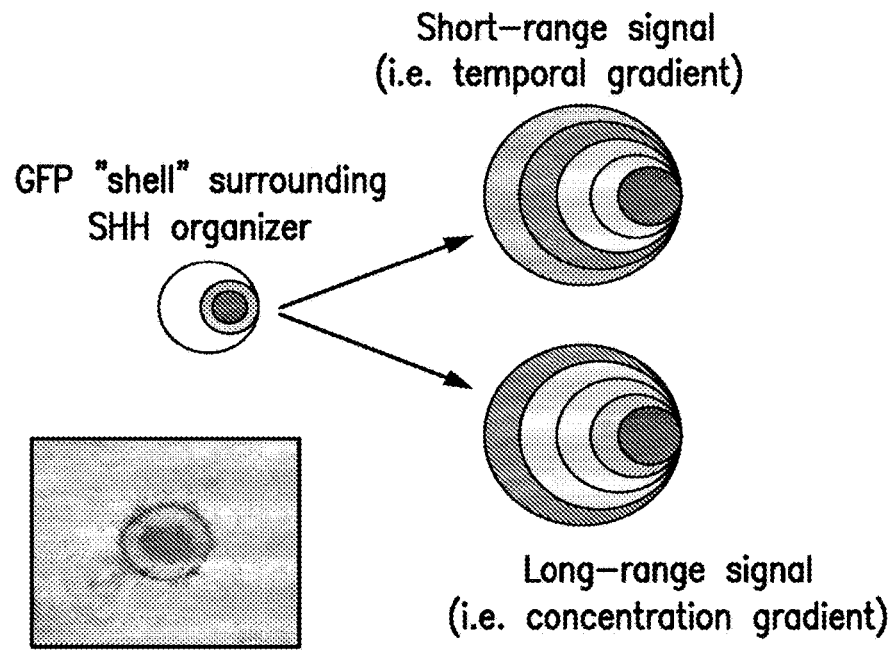
Figure 21C:
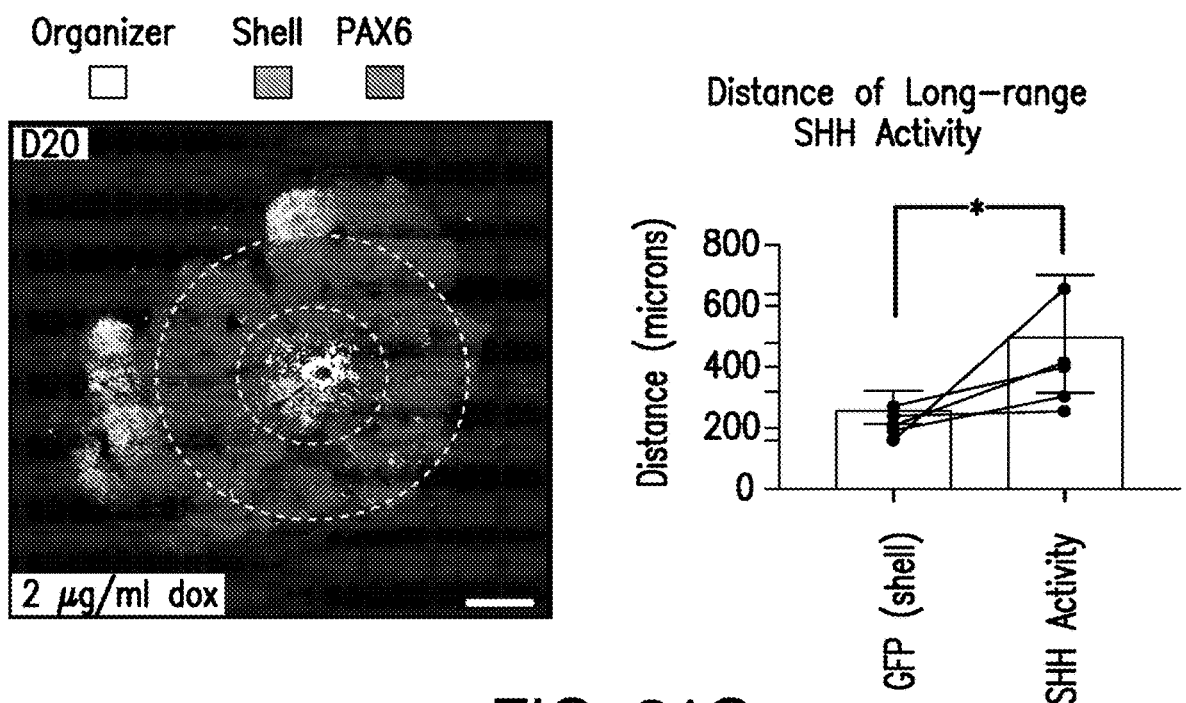

FIGS. 21A-21C. Characterization of long-range SHH signaling mechanism. (A) Comparison of distance of SHH-signaling activity after 12 days of differentiation in 3D and 2D culture using 2 ug/ml doxycycline. In 3D culture, SHH acts over 335±54 µm from the iSHH-organizer, assessed by suppression of PAX6 expression. In 2D culture, SHH acts 75±31 µm from the iSHH-organizer cells. Insets show high-magnification images. Quantification shows mean±S.D. Individual replicates are plotted on graphs. Student two-tailed t-test. **** P<0.0001. N=5 organoids, 2 batches (3D), n=4 differentiations (2D). (B) Depiction of experiment to distinguish between two theoretical mechanisms for long-range SHH activity in 3D culture. A shell of GFP-expressing hPSCs is embedded around the iSHH organizer (see methods). A temporal model is supported if all SHH activity remains encapsulated within the GFP shell. A concentration-dependent model is supported if SHH activity extends past the GFP shell. (C) After 20 days of differentiation in 2 µg/ml doxycycline, SHH activity is observed to extend past the GFP shell. The green dotted circle indicates the boundary of the GFP shell and the purple dotted circle indicates the boundary of the SHH activity, assessed by suppression of PAX6 activity. Quantifications show that the GFP shell extends 268±24 µm from the iSHH-organizer, while SHH activity extends 508±86 µm from the iSHH-organizer. Quantification shows mean±S.D. Student two-tailed t-test. * P=0.028. Individual replicates are plotted on graphs and data points for matched organoids are connected. N=5 organoids, 2 batches. Scale bars: 200 µm (low magnification), 50 µm (high magnification).

FIGS. 22A-22D. Statins perturb tissue growth and SHH signaling. (A) Experimental design to test effect of statins on SHH-organoid development. (B) Four distinct positional domains are identified in day 20 SHH-organoids (400 ng/ml doxycycline). SHH-organoids treated with cyclopamine (1

μm) largely express PAX6, with some GSH2 immunoreactivity, suggesting a near complete inhibition of SHH activity. SHH-organoids treated by AY9944 (1.25 μm) fail to induce NKX2.2 and only retain NKX2.1 expression in the immediate vicinity of the organizer, suggesting a strong reduction the range of SHH-signaling activity. SHH organoids treated with Lovastatin (5 μm) exhibit a moderate reduction in NKX2.2 induction, with a concomitant increase in the relative area of the GSH2 expression domain. Summary of drug phenotypes and potential impact on SHH signaling activity is depicted at bottom of panel. (C) Quantification of area of each positional domain, relative to total area. Dots represent individual organoids, Error bars are S.D. No drug N=8-14; Cyclopamine N=5-14; AY9944 N=8-16; Lovastatin N=7-13. * $P<0.05$; *$P<0.001$, **$P<0.0001$. (D) Lovastatin produces a dose-dependent reduction in the distance at which NKX2.2 is induced from the organizer (red dotted boundary). Frequency histograms plot the relative distribution of organizer and NKX2.2 positive cells as a function of distance from the center of the organizer. Dotted lines represent S.E.M. Bar graphs quantify the average distance between the center of NKX2.2 and organizer distributions, illustrated by horizontal grey bars in frequency histograms. Dots represent individual organoids. Error bars are S.D. No drug, N=23; Lovastatin (Lova) 2 μm N=18; Lova 5 μm N=24; Lova 20 μm N=23; Simvastatin (Simv) N=12; Atorvastatin (Atorv) N=10 Scale bars: 200 μm (Day 20): 50 μm (Day 6).

FIGS. 23A-23D. Additional data related to FIG. 19. (A) Schematic of $[I^{125}]$ Iodopalmitate labeling experiment (left). SHH produced from the iSHH line is palmitoylated at levels proportional to the amount of SHH protein expressed, suggesting that overexpression does not saturate processing machinery. (B) Reproducibility of organizer plating and formation of SHH-H9 spheroids. 1,000 iSHH cells are plated in low-attachment microwells and allowed to aggregate overnight. 10,000 wildtype hPSCs are plated on top of the iSHH organizer cells. (C) Spheroids are embedded in matrigel, and the day of embedding is critical to efficient neuroepithelial growth. SHH organoids (no dox) embedded on day 5 exhibit no neuroepithelial growth, while SHH organoids (no dox) embedded on day 6 exhibit efficient neuroepithelial formation. (D) Typically, the iSHH organizer remains clustered at one pole during differentiation, though in ~25% of instances the organizer can split into multiple distinct clusters. Scale bars: 200 μM.

Figure 24A:
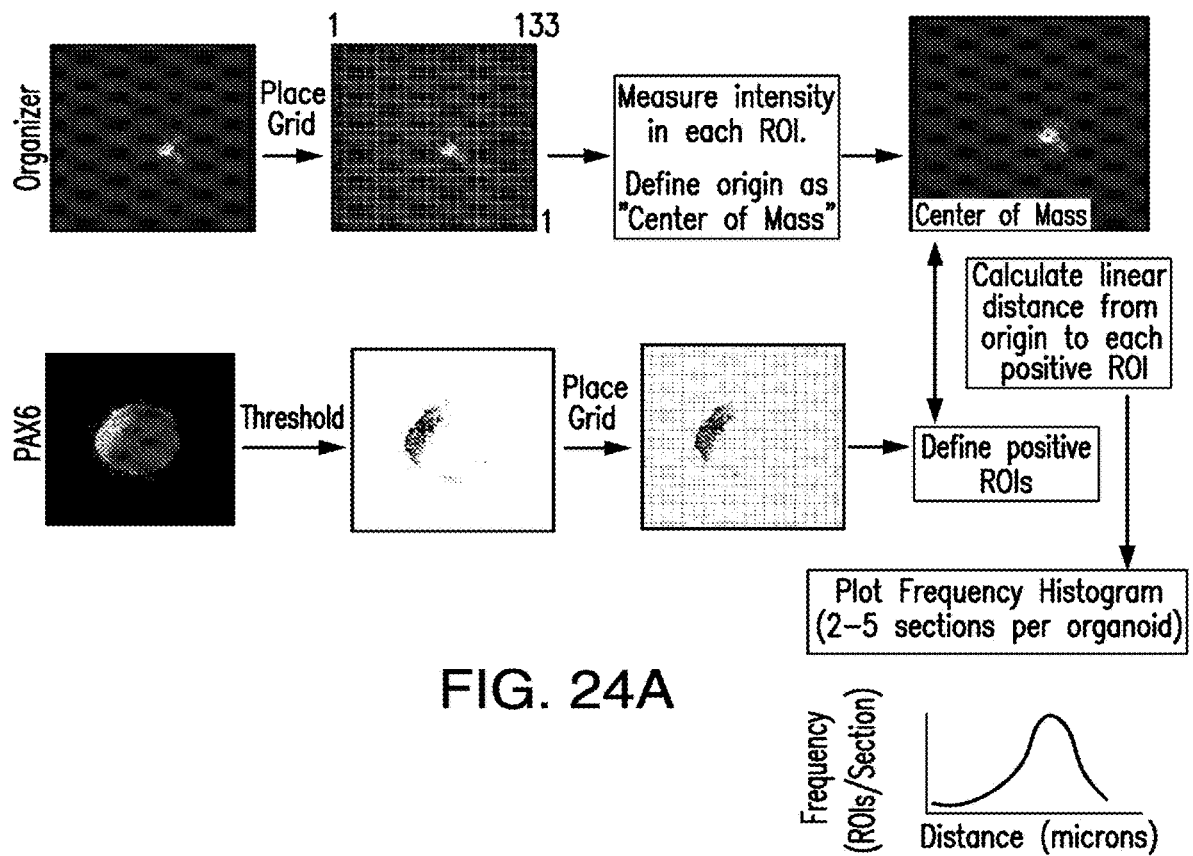
Figure 24B:
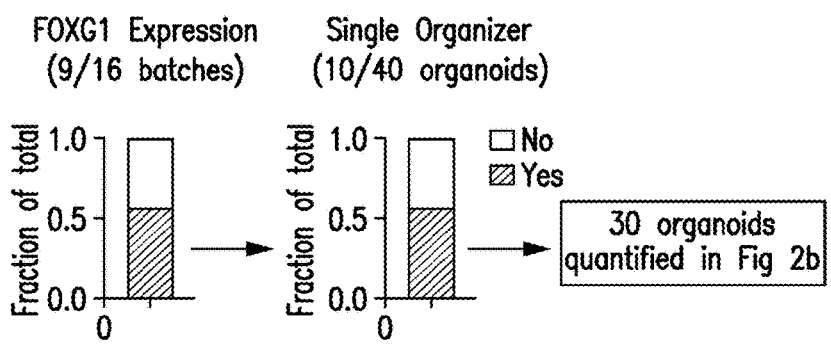
Figure 24C:
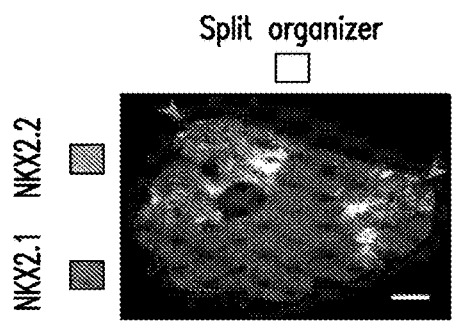

FIGS. 24A-24C. Quantification method for characterizing SHH-organoid topography. (A) SHH-organoids are quantified using a grid of regions of interest (ROIs), and each ROI is associated with an X and Y coordinate. The origin is defined for each section by calculating the "center of mass" of the organizer signal. The grid is then used to define ROIs that are positive for regional markers (e.g. PAX6). The linear distance from all positive ROIs to the origin is calculated, and these data can be plotted as a frequency histogram. (B) Organoids that did not express FOXG1, or that had a split organizer (C) were not included in the quantification. Scale bars: 200 μM.

Figure 25:
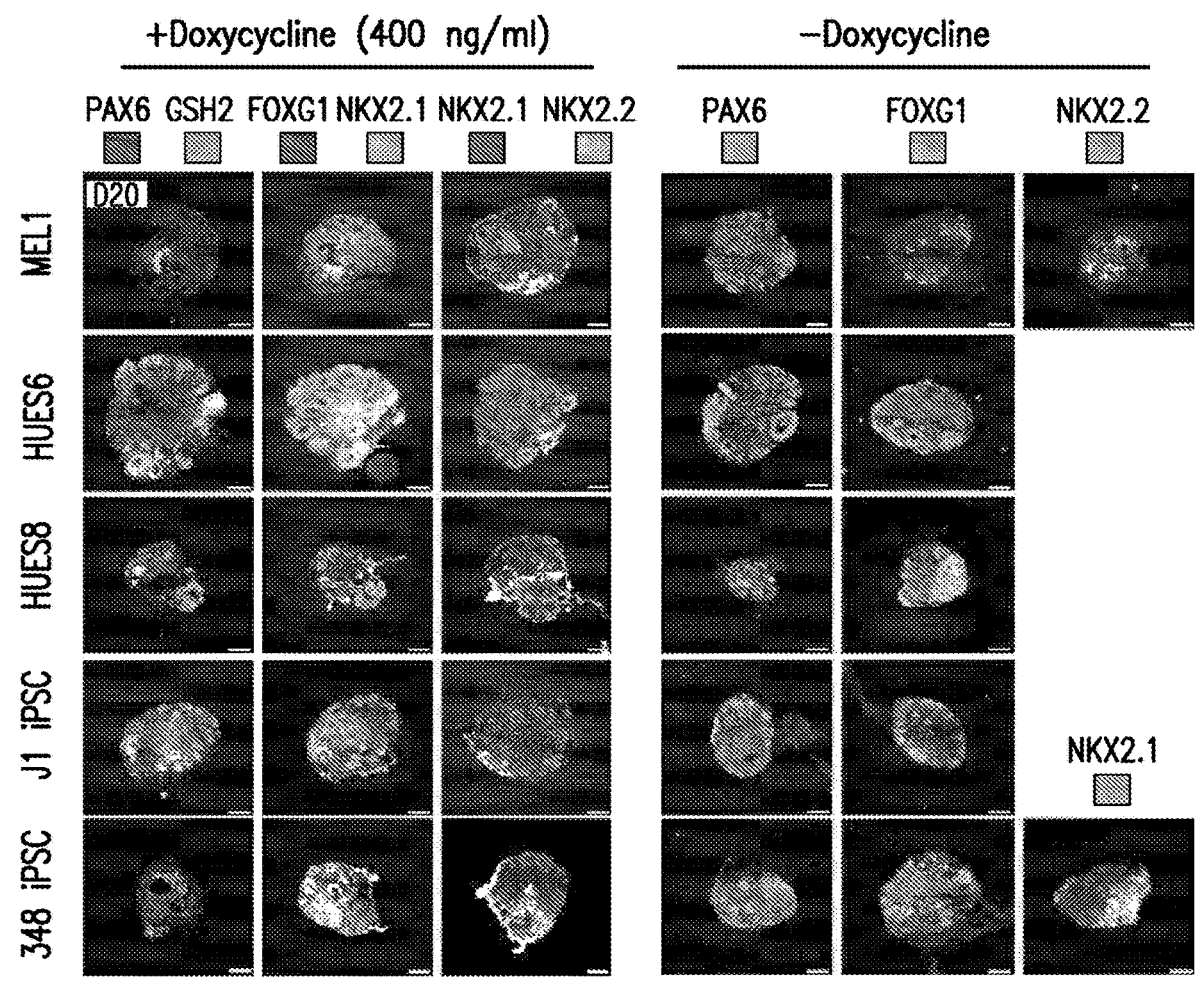

FIG. 25. Topographic patterning in 3 additional hPSC lines (MEL1, HUES6, HUES8) and 2 iPSC lines (J1 and 348). the iSHH organizer can induce distinct regional domains that emerge in the anatomically correct topographic order. However, the size of domains and overall growth rate of organoids may differ between lines. Without doxycycline all lines are predominantly PAX6 and FOXG1 positive. Sparse induction of NKX2.1 and NKX2.2 was observed in MEL1 and 348 lines. +Doxycycline, n=8 organoids, 2 batches for all lines; −Doxycycline, n=4 organoids, 1 batch. Scale bars: 200 μM.

Figure 26A:
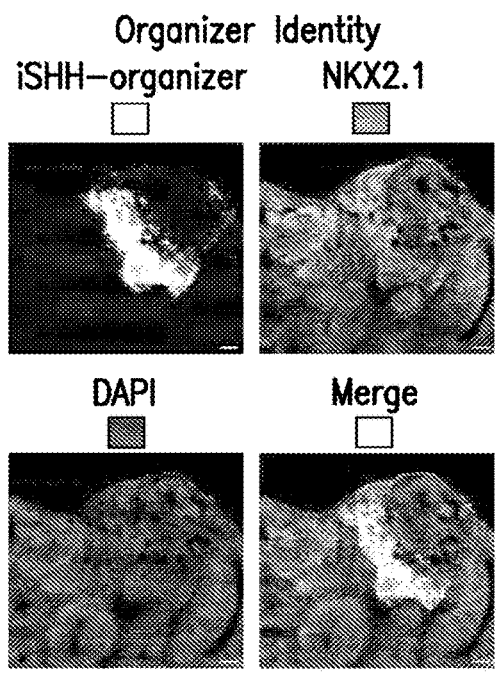
Figure 26C:
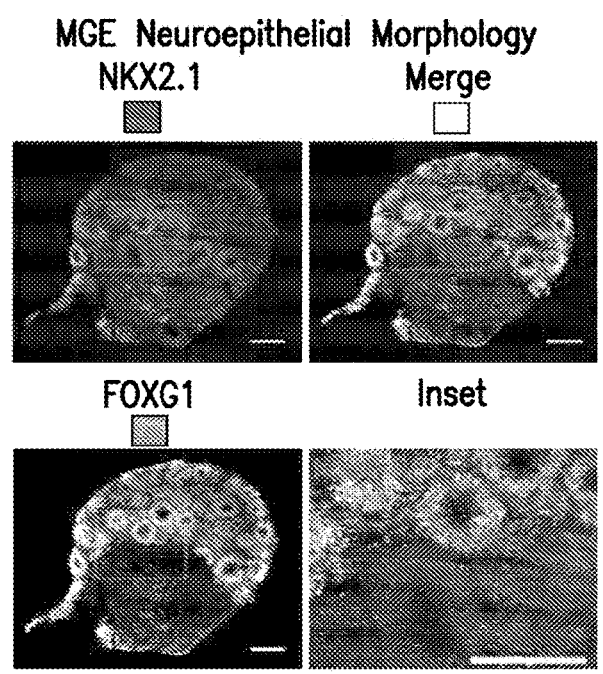
Figure 26B:
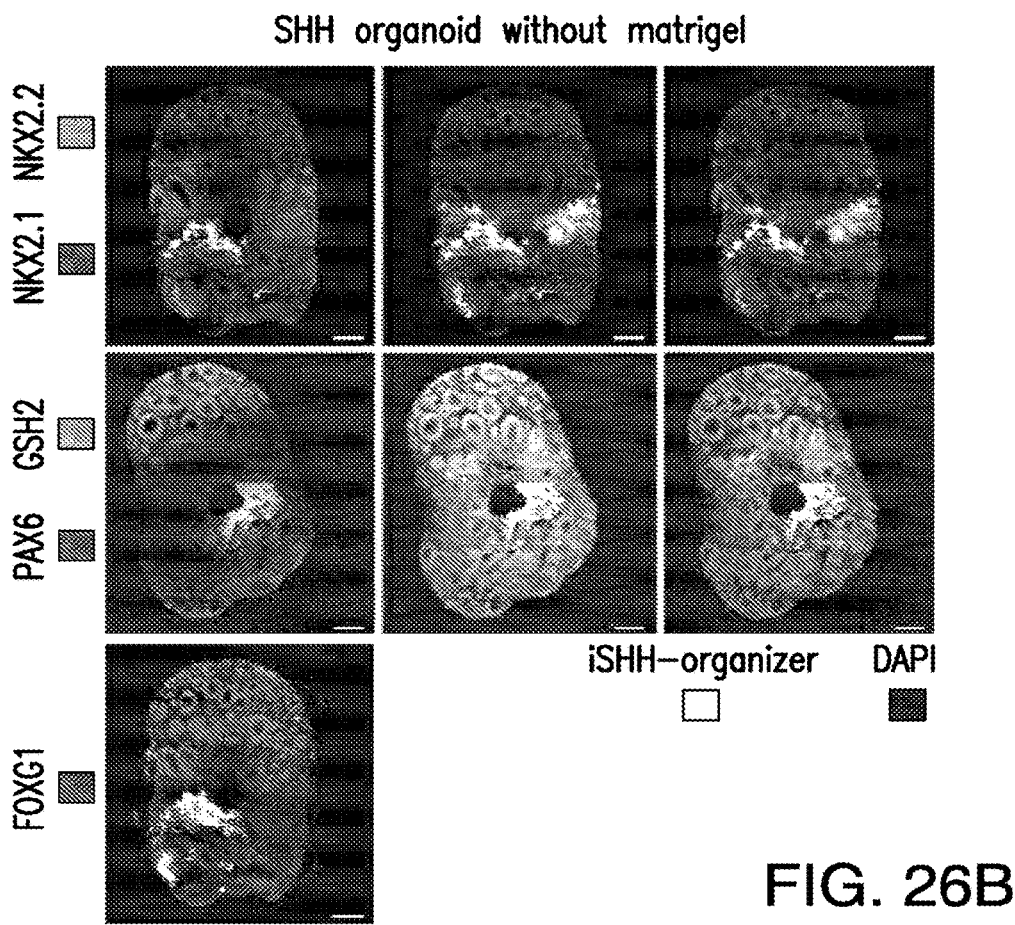

FIGS. 26A-26C. Additional data related to FIG. 20. (A) iSHH organizer cells (red) at least partially express NKX2.1 (green) and are negative for FOXG1, suggesting hypothalamic identity. (B) SHH-dependent topographic patterning can be achieved without matrigel embedding. (C) MGE-like neuroepithelium (FOXG1+/NKX2.1+) acquires a circular, rosette-like structure suggestion a radial organization. Scale bars: 50 μM (26A), 200 μM (B-C).

FIGS. 27A-27F. Characterization of interneuron diversity in SHH-organoids using LHX6-citrine line. (A) LHX6+ cells emerge in regions proximal to the organizer, and co-express NKX2.1. (B) A subset of LHX6+ cells expresses FOXG1, consistent with striatal or cortical interneuron identity. (C) Some FOXG1+/LHX6+ cells have a leading process morphology, characteristic of migrating cortical interneurons. (D-F) Diverse interneuron populations expressing somatostatin (D), parvalbumin (E), and calretinin (F) are observed. Parvalbumin+ cells do not express LHX6, suggesting a non-MGE source of these cells. Scale bars: 50 μM (high magnification), 100 μM (intermediate magnification), 200 μM (low magnification).

FIGS. 28A-28F. Characterization of interneuron diversity in SHH-organoids using LHX6-citrine line. (A) LHX6+ cells emerge in regions proximal to the organizer, and co-express NKX2.1. (B) A subset of LHX6+ cells expresses FOXG1, consistent with striatal or cortical interneuron identity. (C) Some FOXG1+/LHX6+ cells have a leading process morphology, characteristic of migrating cortical interneurons. (D-F) Diverse interneuron populations expressing somatostatin (D), parvalbumin (E), and calretinin (F) are observed. Parvalbumin+ cells do not express LHX6, suggesting a non-MGE source of these cells. Scale bars: 50 μM (high magnification), 100 μM (intermediate magnification), 200 μM (low magnification).

FIGS. 29A-29D. Additional data related to FIG. 22. (A) AY9944 and lovastatin treated organoids retain NKX2.1 and OTX2 expression within the organizer at day 20. (B) Absolute and relative quantification of organizer size in drug treated organoids at day 20. (C) AY9944 strongly inhibits induction of NKX2.2 in day 6 organoids at all concentrations tested. (D) Western blot for SHH protein from day 4 hPSC-derived neural differentiations shows appropriate processing of SHH peptide length (N=3).  $P<0.01$; *$P<0.001$, ****$P<0.0001$. Scale bars: 100 μM (intermediate magnification).

5. DETAILED DESCRIPTION OF THE INVENTION

Provided herein are methods and compositions for generating a gradient of differentiating agent within a three-dimensional body of embryonic stem cells, and subsequent culturing of the tissue, to produce a patterned tissue which is asymmetrical in at least one, at least two, or three dimensions. In particular non-limiting embodiments, the present disclosure provides methods and compositions to generate, in vitro, topographically patterned 3-dimensional neural tissue (brain organoids) having an anterior region (forebrain) and a posterior region (hindbrain) which bear distinctive features.

For clarity and not by way of limitation, this detailed description is divided into the following subsections:

5.1 Definitions;
5.2 Methods of producing topographically organized brain organoids;
5.3 Compositions comprising topographically organized brain organoids; and
5.4 Uses for topographically organized brain organoids.

5.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "signaling" refers to a "signal transduction protein" refers to a protein that is activated or otherwise affected by ligand binding to a membrane receptor protein or some other stimulus. Examples of signal transduction protein include, but are not limited to, JNK, transforming growth factor beta (TGFβ), Activin, Nodal, Wingless (Wnt), bone morphogenetic protein (BMP), fibroblast growth factor (FGF), and glycogen synthase kinase 3β (GSK3 β) proteins. For many cell surface receptors or internal receptor proteins, ligand-receptor interactions are not directly linked to the cell's response. The ligand activated receptor can first interact with other proteins inside the cell before the ultimate physiological effect of the ligand on the cell's behavior is produced. Often, the behavior of a chain of several interacting cell proteins is altered following receptor activation or inhibition. The entire set of cell changes induced by receptor activation is called a signal transduction mechanism or signaling pathway.

As used herein, the term "signals" refer to internal and external factors that control changes in cell structure and function. They can be chemical or physical in nature.

As used herein, the term "ligands" refers to molecules and proteins that bind to receptors, e.g., Activin, Nodal, Wnt, BMP, FGF etc.

"Inhibitor" or "antagonist" as used herein, refers to a compound or molecule (e.g., small molecule, peptide, peptidomimetic, natural compound, siRNA, anti-sense nucleic acid, aptamer, or antibody) that interferes with (e.g., reduces, decreases, suppresses, eliminates, or blocks) the signaling function of a protein or pathway. An inhibitor can be any compound or molecule that changes any activity of a named protein (signaling molecule, any molecule involved with the named signaling molecule, a named associated molecule) (e.g., including, but not limited to, the signaling molecules described herein), for one example, via directly contacting the signaling protein, contacting mRNA, causing conformational changes of the protein, decreasing protein levels, or interfering with interactions with signaling partners (e.g., including those described herein), and affecting the expression of target genes (e.g. those described herein). Inhibitors also include molecules that indirectly regulate biological activity by intercepting upstream signaling molecules (e.g., within the extracellular domain). Antibodies that block upstream or downstream proteins are contemplated for use to neutralize extracellular activators of protein signaling, and the like. Inhibitors are described in terms of competitive inhibition (binds to the active site in a manner as to exclude or reduce the binding of another known binding compound) and allosteric inhibition (binds to a protein in a manner to change the protein conformation in a manner which interferes with binding of a compound to that protein's active site) in addition to inhibition induced by binding to and affecting a molecule upstream from the named signaling molecule that in turn causes inhibition of the named molecule. An inhibitor can be a "direct inhibitor" that inhibits a signaling target or a signaling target pathway by actually contacting the signaling target.

"Activators," as used herein, refer to compounds that increase, induce, stimulate, activate, facilitate, or enhance activation the signaling function of the molecule or pathway, e.g., Wnt signaling, Nodal signaling, etc.

As used herein, the term "derivative" refers to a chemical compound with a similar core structure.

As used herein, the term "a population of cells" or "a cell population" refers to a group of at least two cells. In non-limiting examples, a cell population can include at least about 10, at least about 100, at least about 200, at least about 300, at least about 400, at least about 500, at least about 600, at least about 700, at least about 800, at least about 900, at least about 1000 cells. The population may be a pure population comprising one cell type, or a population of undifferentiated stem cells. Alternatively, the population may comprise more than one cell type, for example a mixed cell population.

As used herein, the term "stem cell" refers to a cell with the ability to divide for indefinite periods in culture and to give rise to specialized cells. In certain embodiments, the stem cells are human stem cells.

As used herein, the term "embryonic stem cell" and "ESC" refer to a primitive (undifferentiated) cell that is derived from preimplantation-stage embryo, capable of dividing without differentiating for a prolonged period in culture, and are known to develop into cells and tissues of the three primary germ layers. A human embryonic stem cell refers to an embryonic stem cell that is from a human embryo. As used herein, the term "human embryonic stem cell" or "hESC" refers to a type of pluripotent stem cells derived from early stage human embryos, up to and including the blastocyst stage, that is capable of dividing without differentiating for a prolonged period in culture, and are known to develop into cells and tissues of the three primary germ layers.

As used herein, the term "embryonic stem cell line" refers to a population of embryonic stem cells which have been cultured under in vitro conditions that allow proliferation without differentiation for up to days, months to years.

As used herein, the term "pluripotent" refers to an ability to develop into the three developmental germ layers of the organism including endoderm, mesoderm, and ectoderm. In certain embodiments, the pluripotent cell is selected from the group consisting human, nonhuman primate or rodent non-embryonic stem cells; human, nonhuman primate or rodent embryonic stem cells; human, nonhuman primate or rodent induced pluripotent stem cells; and human, nonhuman primate or rodent recombinant pluripotent cells.

As used herein, the term "induced pluripotent stem cell" or "iPSC" refers to a type of pluripotent stem cell formed by the introduction of certain embryonic genes (such as but not limited to OCT4, SOX2, and KLF4 transgenes) (see, for example, Takahashi and Yamanaka Cell 126, 663-676 (2006), herein incorporated by reference) into a somatic cell, for examples, CI 4, C72, and the like. An induced pluripotent stem cell may be prepared from any fully (e.g., mature or adult) or partially differentiated cell using methods known in the art. For example, but not by way of limitation, an induced pluripotent stem cell may be prepared from a fibroblast, such as a human fibroblast; an epithelial cell, such as a human epithelial cell; a blood cell such as a lymphocyte or hematopoietic cell or cell precursor or myeloid cell, such as a human lymphocyte, hematopoietic cell or cell precursor or human myeloid cell; or a renal epithelial cell, such as a human renal epithelial cell. In certain non-limiting embodiments, an induced pluripotent stem cell contains one or more introduced reprogramming factor associated with producing pluripotency. In certain non-limiting embodiments, a human induced pluripotent stem cell is not identical to a human embryonic pluripotent stem cell.

As used herein, the term "somatic cell" refers to any cell in the body other than gametes (egg or sperm); sometimes referred to as "adult" cells.

As used herein, the term "somatic (adult) stem cell" refers to a relatively rare undifferentiated cell found in many organs and differentiated tissues with a limited capacity for both self-renewal (in the laboratory) and differentiation.

As used herein, the term "undifferentiated" refers to a cell that has not yet developed into a specialized cell type.

As used herein, the term "differentiation" refers to a process whereby an unspecialized cell acquires the features of a specialized cell such as a neuron, heart, liver, or muscle cell. Differentiation is controlled by the interaction of a cell's genes with the physical and chemical conditions outside the cell, usually through signaling pathways involving proteins embedded in the cell surface.

As used herein, the term "directed differentiation" refers to a manipulation of stem cell culture conditions to induce differentiation into a particular (for example, desired) cell type.

As used herein, the term "directed differentiation" in reference to a stem cell refers to the use of small molecules, growth factor proteins, and other growth conditions to promote the transition of a stem cell from the pluripotent state into a more mature or specialized cell fate.

As used herein, the term "inducing differentiation" in reference to a cell refers to changing the default cell type (genotype and/or phenotype) to a non-default cell type (genotype and/or phenotype). Thus, "inducing differentiation in a stem cell" refers to inducing the stem cell (e.g., stem cell) to divide into progeny cells with characteristics that are different from the stem cell, such as genotype (e.g., change in gene expression as determined by genetic analysis such as a microarray) and/or phenotype (e.g., change in expression of a protein).

As used herein, the term "cell culture" refers to a growth of cells in vitro in an artificial medium for research or medical treatment.

As used herein, the term "culture medium" refers to a liquid that covers cells in a culture vessel, such as a Petri plate, a multi-well plate, and the like, and contains nutrients to nourish and support the cells. Culture medium may also include growth factors added to produce desired changes in the cells.

As used herein, the term "contacting" a cell or cells with a compound (e.g., one or more inhibitor, activator, and/or inducer) refers to exposing or otherwise providing the compound in a location that permits the cell or cells access to the compound. The contacting may be accomplished using any suitable method. For example, contacting can be accomplished by adding the compound, in concentrated form, to a cell or population of cells, for example in the context of a cell culture, to achieve the desired concentration. Contacting may also be accomplished by including the compound as a component of a formulated culture medium.

As used herein, the term "in vitro" refers to an artificial environment and to processes or reactions that occur within an artificial environment. In vitro environments exemplified, but are not limited to, test tubes and cell cultures.

As used herein, the term "in vivo" refers to the natural environment (e.g., an animal or a cell) and to processes or reactions that occur within a natural environment, such as embryonic development, cell differentiation, neural tube formation, etc.

As used herein, the term "expressing" in relation to a gene or protein refers to making an mRNA or protein which can be observed using assays such as microarray assays, antibody staining assays, and the like.

As used herein, the term "marker" or "cell marker" refers to gene or protein that identifies a particular cell or cell type. A marker for a cell may not be limited to one marker, markers may refer to a "pattern" of markers such that a designated group of markers may identity a cell or cell type from another cell or cell type.

As used herein, the term "derived from" or "established from" or "differentiated from" when made in reference to any cell disclosed herein refers to a cell that was obtained from (e.g., isolated, purified, etc.) a parent cell in a cell line, tissue (such as a dissociated embryo), or fluids using any manipulation, such as, without limitation, single cell isolation, culture in vitro, treatment and/or mutagenesis using for example proteins, chemicals, radiation, infection with virus, transfection with DNA sequences, such as with a morphogen, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, protein or RNA expression, sorting procedure, and the like.

An "individual" or "subject" herein is a vertebrate, such as a human or non-human animal, for example, a mammal. Mammals include, but are not limited to, humans, non-human primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

An "effective amount" of a substance as that term is used herein is that amount sufficient to effect beneficial or desired results, including clinical results, and, as such, an "effective amount" depends upon the context in which it is being applied. An effective amount can be administered in one or more administrations.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more sign or symptoms, diminishment of extent of disease, stabilized (i.e., not worsening) state of disease, prevention of disease, delay or slowing of disease progression, and/or amelioration or palliation of the disease state. The decrease can be a 10%, 20%, 30%, 40%, 50%, 60%, 70%, 80%, 90%, 95%, 98% or 99% decrease in severity of complications or symptoms. "Treatment" can also mean prolonging survival as compared to expected survival if not receiving treatment.

5.2 Methods of Producing Topographically Organized Brain Organoids

In certain embodiments, the present disclosure provides methods of producing a topographically organized brain organoid. In certain embodiments, the method comprises;

(i) providing an "organizer" that is a source of diffusible organizing agent, (ii) placing the organizer in apposition to an aggregate of undifferentiated or partially differentiated stem cells to form an organizer/aggregate complex; and (iii) culturing the organizer/aggregate complex in vitro to result in differentiation of the cells in the aggregate to promote the formation of neural tissue, wherein the organizer releases organizing agent to form a gradient concentration of organizing agent effective in generating, in the organoid, cells having different phenotypes at different distances from the organizer.

In certain non-limiting embodiments, the cells in the organizer and/or aggregate are human or non-human cells. In certain non-limiting embodiments, the cells in the organizer and/or aggregate are human or non-human stem cells. Non-limiting examples of non-human cells (or stem cells) include non-human primate cells, mouse cells, rat cells, hamster cells, rabbit cells, dog cells, cat cells, horse cells, etc.

In certain non-limiting embodiments, the stem cells ("SCs") are embryonic stem cells ("ESCs") or induced pluripotent stem cells ("iPSCs"). In certain embodiments, the stem cells are pluripotent stem cells ("PSCs") or multipotent stem cells. In certain non-limiting embodiments, the stem cells are PSCs. In certain non-limiting embodiments, the stem cells are maintained in hESC medium, for example Essential 8 medium (Life Technologies). In certain non-limiting embodiments, the stem cells can be partially differentiated prior to formation of the aggregate or prior to contacting with the organizer. In certain non-limiting embodiments, one or more stem cell comprised in the organoids described herein contain a heterologous nucleic acid, for example, but not limited to, a nucleic acid encoding, in expressible form, an organizing agent; a nucleic acid encoding, in expressible form, a detectable reporter molecule such as, but not limited to, a fluorescent protein or luciferase; a nucleic acid encoding a differentiation factor or growth factor or transcription modulator; or a nucleic acid encoding, for example in inducible form, a suicide gene (e.g. that promotes apoptosis or another form of cell death).

In certain non-limiting embodiments, the organizing agent is a protein. In certain non-limiting embodiments, the protein is a Sonic Hedgehog Protein ("SHH"), which, for example, can be of the same species as the cells comprised in the aggregate. In certain non-limiting embodiments, where an organoid includes human cells, the organizing agent is of human origin. For example, the organizing agent can be human SHH. In certain non-limiting embodiments, the protein is a SHH protein agonist or a protein that induces SHH protein expression or promotes its activity. In certain non-limiting embodiments, the organizing agent is an agent that activates TGFβ/Nodal signaling. In certain non-limiting embodiments, the organizing agent is a fibroblast growth factor ("FGF"). In certain embodiments, the organizing agent is FGF8b. In certain non-limiting embodiments, the organizing agent is FGF2. In certain non-limiting embodiments, the organizing agent is a Wnt activator. In certain embodiments, the organizing agent is WNT7a. In certain non-limiting embodiments, the organizing agent is WNT3a. In certain non-limiting embodiments, the organizing agent is WNT1. In certain non-limiting embodiments, the organizing agent is an agent that promotes the expression of transcription factor SIM2. In certain non-limiting embodiments, the organizing agent is an agent that promotes the expression of transcription factor FOXA2. In certain non-limiting embodiments, the organizing agent is an SHH homolog, for example Indian Hedgehog ("IHH") or Desert Hedgehog ("DHH"). In certain non-limiting embodiments, the organizing agent is a small molecule activator of the hedgehog pathway, such as, but not limited to, Smoothened agonist ("SAG") or retinoic acid.

In certain non-limiting embodiments, the organizer comprises a cell or group of cells that express(es) and secrete(s) an organizing agent. In certain non-limiting embodiments, the cells of the organizer are stem cells, as described above. In certain non-limiting embodiments, the organizer is a cell or cells that express(es) and secrete(s) a SHH protein. In certain non-limiting embodiments, the cells are engineered to express and secrete an organizing agent. In certain non-limiting embodiments, the cells are engineered to express and secrete a SHH. In certain non-limiting embodiments, the organizer comprises ESCs or iPSCs that are engineered to express and secrete a SHH. In certain non-limiting embodiments, expression of the organizing agent is inducible or conditional. In certain non-limiting embodiments, the organizer is a bead or beads comprising an organizing agent in a sustained release form. In certain non-limiting embodiments, the organizer is a bead or beads comprising a SHH in a sustained release form.

In certain non-limiting embodiments, the organizer is comprised of cells that conditionally express an organizing agent. For example, the organizer is comprised of cells that conditionally express SHH. For example, the organizer is comprised of hESCs or iPSCs that conditionally express hSHH when cultured in the presence of the small molecule doxycycline. To generate this cell line, a bicistronic gene cassette can be inserted into the AAVS1 locus of a human pluripotent stem cell line. The gene cassette can comprise 1) a constitutively expressed reverse tetracycline transactivator (rTTa), and 2) a gene coding for a protein (e.g. SHH, FGF, WNT, TGFbeta), that is expressed under the control of a tetracycline response element (TRE). The human pluripotent stem cell line can be marked with a fluorescent reporter protein, such as RFP. The gene cassette can be inserted into the AAVS1 locus via targeted genome editing (e.g. TALENs, CRISPR) (see FIG. 3A).

In certain non-limiting embodiments, the stem cell aggregate is formed prior to placing it in apposition to the organizer. In alternate embodiments, the aggregate is formed concurrently with apposition to the organizer. In still further non-limiting embodiments, the aggregate is formed subsequent to apposition to the organizer.

In certain non-limiting embodiments, the organizer is localized at a pole of the organoid. Organizing agent is released from the organizer to establish a gradient in the organoid as organizing agent diffuses away from the organizer source.

For example, and not by way of limitation, an organizer-containing organoid can be prepared by a method comprising embedding the organizer at one pole of an ESC or iPSC spheroid, and then culturing the organizer-containing ESC or iPSC spheroid to promote differentiation into a desired tissue, for example, a neural tissue. For example, and not by way of limitation, a sequential aggregation protocol can be used to assemble the hESC spheroid/organizer chimera. First, 1000 organizer cells can be plated in a low-attachment "V"-bottom dish. Cells will collect in the bottom of the "V" shaped dish, and aggregate into a sphere. 24 hours later, 10,000 wild-type hESCs can be plated on top of the pre-aggregated organizer cells. In this way, the organizer tissue resides neatly at one pole of the larger hESC spheroid.

In certain non-limiting embodiments, more than one organizer can be placed in apposition to a stem cell aggregate (meaning that a plurality of distinct organizer (areas) are present, separated by a distance).

In certain non-limiting embodiments, an organizer acts similar to a point source. In other non-limiting embodiments, an organizer may manifest more of a linear, planar, or three-dimensional (e.g. spherical or conical) configuration.

Once the hESC spheroid/organizer chimera has been assembled, it can be differentiated into the desired neural tissue via a directed differentiation protocol. For example, to generate topographically patterned forebrain tissue, the chimera can be treated with XAV939 (5 µM), an antagonist of the canonical WNT pathway, for 4 days. In addition, SHH is expressed from the organizer for the first 20 days of differentiation via culturing in doxycycline (2 µg/mL). The organoid can be embedded in matrigel after 4 days of differentiation to promote neuroepithelial organization and outgrowth. After day 8, the organoid cultures can be placed on an orbital shaker or bio-reactor to prevent fusion of organoids in the same dish and promote oxygenation of the tissue. Differentiation medium is preferably Essential 6 medium (Life Technology) for the first 4 days of differentiation, and NeuroBasal/DMEMF-12 with B27 and N2 supplement after 4 days of differentiation.

In addition to topographically organized forebrain tissue, the present disclosure can be used to generate topographically organized midbrain tissue, and tissues of other brain regions. To generate midbrain tissue, the forebrain protocol is used, except XAV939 is not used during the first four days of differentiation. To generate a hindbrain tissue, organoids are treated with FGF2 during the first four days of differentiation, and to generate a spinal cord tissue, organoids are treated with retinoic acid for the first four days of differentiation.

In a particular, non-limiting embodiment, the present disclosure provides methods of producing a topically organized brain organoid. In certain embodiments, the method comprises:

(i) providing an "organizer" comprised of human stem cells (hESCs or hiPSCs) engineered to express and secrete a hSHH;

(ii) placing the organizer in apposition to an aggregate of undifferentiated or partially differentiated pluripotent human stem cells (hESCs or hiPSCs) to form an organizer/aggregate complex having the organizer at one pole of a spheroid stem cell aggregate; and (iii) culturing the organizer/aggregate complex in vitro in medium that promotes differentiation of the cells to form a neural tissue, wherein the organizer releases a hSHH to form a gradient concentration effective in generating a brain organoid comprising at least distinct forebrain and posterior regions.

In certain non-limiting embodiments, the brain organoid comprises one or more of: a region having characteristics of the cerebral cortex; a region having characteristics of the hippocampus; a region having characteristics of the lateral ganglionic eminence ("LGE"); a region having characteristics of the medial ganglionic eminence ("MGE"); and/or a region having characteristics of the hypothalamus ("HtH"). In certain embodiments, the region having characteristics of the HtH comprises a region having characteristics of the anterior hypothalamic and a region having characteristic of the ventro-posterior hypothalamic. In certain non-limiting embodiments, the brain organoid comprises a PAX6-expressing region distinct from a NKX2.1-expressing region. In certain non-limiting embodiments, the brain organoid comprises a demarcated cortex-like region comprising cells expressing FOXG1 and/or PAX6. In certain non-limiting embodiments, the brain organoid comprises a demarcated LGE-like region comprising cells expressing GSH2 and contiguous to a region expressing PAX6. In certain non-limiting embodiments, the brain organoid comprises a demarcated MGE-like region comprising cells expressing NKX2.1 and FOXG1. In certain non-limiting embodiments, the brain organoid comprises a demarcated hypothalamus-like region comprising cells expressing NKX2.2 and NKX2.1. In certain non-limiting embodiments, the brain organoid comprises a demarcated anterior hypothalamic-like region comprising cells expressing NKX2.2. In certain non-limiting embodiments, the brain organoid comprises a demarcated ventro-posterior hypothalamic-like region comprising cells expressing NKX2.1 but not FOXG1. In certain non-limiting embodiments, the brain organoid comprises a forebrain-like region comprising, in order from dorsal to ventral: (i) a demarcated cortex-like region comprising cells expressing FOXG1 and/or PAX6; (ii) a demarcated LGE-like region comprising cells expressing GSH2 and contiguous to a region expressing PAX6; (iii) a demarcated MGE-like region comprising cells expressing NKX2.1 and FOXG1; and (iv) a demarcated hypothalamus-like region comprising cells expressing NKX2.2 and NKX2.1. In certain embodiments, the demarcated hypothalamus-like region comprises a demarcated anterior hypothalamic-like region comprising cells expressing NKX2.2. In certain embodiments, the demarcated hypothalamus-like region comprises a demarcated ventro-posterior hypothalamic-like region comprising cells expressing NKX2.1 but not FOXG1.

In certain embodiments, the methods disclosed herein further comprise contacting the organizer/aggregate complex with an effective amount of one or more bone morphogenetic protein (BMP) inhibitor, one or more transforming growth factor beta (TGFβ)/Activin-Nodal inhibitor, and/or one or more Wingless (Wnt) inhibitor. Contacting the organizer/aggregate complex with such inhibitors assists the specific induction of forebrain identity.

In certain embodiments, a presently disclosed method comprises contacting the organizer/aggregate complex with effective amounts of one or more TGFβ/Activin-Nodal inhibitor, which results in inhibition of Small Mothers Against Decapentaplegic (SMAD) signaling. In certain embodiments, the TGFβ/Activin-Nodal inhibitor neutralizes the ligands including TGFβs, BMPs, Nodal, and activins, or blocking their signal pathways through blocking the receptors and downstream effectors.

Non-limiting examples of TGFβ/Activin-Nodal inhibitors are disclosed in WO/2010/096496, WO/2011/149762, WO/2013/067362, WO/2014/176606, WO/2015/077648, Chambers et al., Nature Biotechnology 27, 275-280 (2009), and Chambers et al., Nature biotechnology 30, 715-720 (2012), which are incorporated by reference in their entireties herein for all purposes. In certain embodiments, the one or more TGFβ/Activin-Nodal inhibitor is a small molecule selected from the group consisting of SB431542, derivatives thereof, and mixtures thereof "SB431542" refers to a molecule with a number CAS 301836-41-9, a molecular formula of $C_{22}H_{18}N_4O_3$, and a name of 4-[4-(1,3-benzodioxol-5-yl)-5-(2-pyridinyl)-1H-imidazol-2-yl]-benzamide, for example, see structure below:

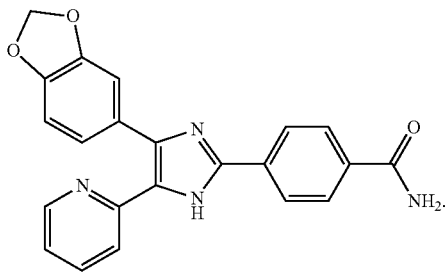 [SMILES: NC(=O)c1ccc(-c2nc(-c3ccc4c(c3)OCO4)c(-c3ccccn3)[nH]2)cc1]

In certain embodiments, a presently disclosed method comprises contacting the organizer/aggregate complex with effective amounts of one or more Wnt inhibitor. The term "Wnt inhibitor" as used herein refers not only to any agent that may act by directly inhibiting the normal function of the Wnt protein, but also to any agent that inhibits the Wnt signaling pathway, and thus recapitulates the function of Wnt. Examples of the Wnt inhibitors include XAV939 (Hauang et al. Nature 461:614-620 (2009)), vitamin A (retinoic acid), lithium, flavonoid, Dickkopf1 (Dkk1), insulin-like growth factor-binding protein (IGFBP) (WO2009/131166), and siRNAs against β-catenin.

Exemplary Wnt inhibitors include, but are not limited to, XAV939, IWP-2, DKK1 (Dickkopf protein 1), and IWR1. Additional Wnt inhibitors include, but are not limited to, IWR compounds, IWP compounds, and other Wnt inhibitors described in WO09155001 and Chen et al., Nat Chem Biol 5:100-7 (2009).

XAV939 is a potent, small molecule inhibitor of tankyrase (TNKS) 1 and 2 with $IC_{50}$ values of 11 and 4 nM, respectively. Huang et al., Nature 461:614-620 (2009). By inhibiting TNKS activity, XAV939 increases the protein levels of the axin-GSK3β complex and promotes the degradation of β-catenin in SW480 cells. Known Wnt inhibitors also include Dickkopf proteins, secreted Frizzled-related proteins (sFRP), Wnt Inhibitory Factor 1 (WIF-1), and Soggy. Members of the Dickkopf-related protein family (Dkk-1 to -4) are secreted proteins with two cysteine-rich domains, separated by a linker region. Dkk-3 and -4 also have one prokineticin domain. Dkk-1, -2, -3, and -4 function as antagonists of canonical Wnt signaling by binding to LRP5/6, preventing LRP5/6 interaction with Wnt-Frizzled complexes. Dkk-1, -2, -3, and -4 also bind cell surface Kremen-1 or -2 and promote the internalization of LRP5/6. Antagonistic activity of Dkk-3 has not been demonstrated. Dkk proteins have distinct patterns of expression in adult and embryonic tissues and have a wide range of effects on tissue development and morphogenesis.

The Dkk family also includes Soggy, which is homologous to Dkk-3 but not to the other family members. The sFRPs are a family of five Wnt-binding glycoproteins that resemble the membrane-bound Frizzleds. The largest family of Wnt inhibitors, they contain two groups, the first consisting of sFRP1, 2, and 5, and the second including sFRP3 and 4. All are secreted and derived from unique genes, none are alternate splice forms of the Frizzled family. Each sFRP contains an N-terminal cysteine-rich domain (CRO). Other Wnt inhibitors include WIF-1 (Wnt Inhibitory Factor 1), a secreted protein that binds to Wnt proteins and inhibits their activity.

In certain embodiments, a presently disclosed method comprises contacting the organizer/aggregate complex with effective amounts of one or more BMP inhibitor. Exemplary BMP inhibitors include, but are not limited to: Noggin, BMP receptor inhibitors, inhibitors of SMAD1/5/8 phosphorylation, inhibitors of the interaction of SMAD1/5/8 and SMAD4, and activators/agonists of SMAD6 and SMAD7. The categorizations described below are merely for organizational purposes and one of skill in the art would know that compounds can affect one or more points within a pathway, and thus compounds may function in more than one of the defined categories.

Inhibitors of SMAD1/5/8 phosphorylation include, but are not limited to, antibodies to, dominant negative variants, antisense nucleic acids, and small molecules that target SMAD1, SMAD5, or SMAD8. Specific examples of inhibitors include LDN-193189 and Dorsomorphin (commercially available from, e.g., Stemgent)

BMP receptor inhibitors include, but are not limited to, antibodies to, dominant negative variants of, siRNA or antisense nucleic acids, or small molecules that target BMP receptors. Specific examples of inhibitors include, but are not limited to, DMH-1, Dorsomorphin dihydrochloride, and LDN-193189 (commercially available, from, e.g., Tocris Biosciences).

LDN193189 (i.e., DM-3189, IUPAC 4-(6-(4-(piperazin-1-yl)phenyl)pyrazolo[1,5-a]pyrimidin-3-yl)quinolone) is a commercially available small molecule inhibitor of SMAD signaling. LDN193189 is also a highly potent small molecule inhibitor of ALK2, ALK3, ALK6, protein tyrosine kinases (PTK), inhibiting signaling of members of the ALK1 and ALK3 families of type I TGFβ receptors, resulting in the inhibition of the transmission of multiple biological signals, including the bone morphogenetic proteins (BMP) BMP2, BMP4, BMP6, BMP7, and Activin cytokine signals and subsequently SMAD phosphorylation of Smad1, Smad5, and Smad8. Yu et al., Nat Med 14:1363-1369 (2008) and Ctmy et al., Bioorg Med Chem Lett 18:4388-4392 (2008). The structure of LDN193189 is listed below:

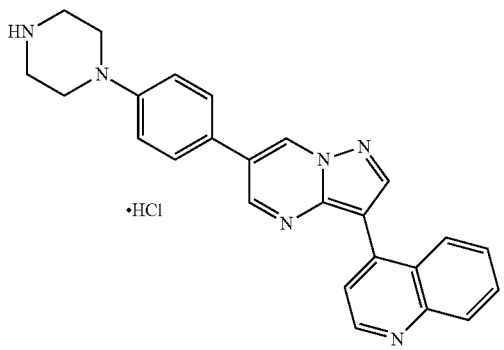 [SMILES: c1ccc2c(-c3cnn4cc(-c5ccc(N6CCNCC6)cc5)cnc34)ccnc2c1 ; Cl]

·HCl

In certain embodiments, the organizer/aggregate complex is contacted with the one or more BMP inhibitor at a concentration of between about 10 and 500 nM, between about 20 and 450 nM, between about 30 and 400 nM, between about 40 and 350 nM, between about 50 and 300 nM, between about 60 and 250 nM, between about 70 and 200 nM, between about 80 and 150 nM, between about 90 and 140 nM, between about 95 and 120 nM, or about 100 nM.

In certain embodiments, the organizer/aggregate complex is contacted with the one or more BMP inhibitor at a concentration of at least about 10, 20, 30, 40, 50, 60, 70, 80, 90, 100, 110, 120, 130, 140, or 150 nM or more.

In certain embodiments, the organizer/aggregate complex is contacted with the one or more BMP inhibitor for at least, or up to, 1, 2, 3, 4, 5, 6, 7, 8, 9, 10, 11, or 12 days or more. In certain embodiments, the organizer/aggregate complex is contacted with the one or more BMP inhibitor for up to, or up to, at least 6, 7, or 8 days.

In certain embodiments, the organizer/aggregate complex is contacted with the one or more TGFβ/Activin-Nodal inhibitor at a concentration of between about 1 and 50 nM, between about 2 and 45 µM, between about 3 and 40 µM, between about 4 and 35 µM, between about 5 and 30 µM, between about 6 and 25 µM, between about 7 and 20 µM, between about 8 and 15 µM, between about 9 and 14 µM, between about 9.5 and 12 µM, or about 10 µM.

In certain embodiments, the organizer/aggregate complex is contacted with the one or more TGFβ/Activin-Nodal inhibitor at a concentration of at least about 1, 2, 3, 4, 5, 6, 7, 8, 9, 10, 11, 12, 13, 14, or 15 µM or more.

In certain embodiments, the organizer/aggregate complex is contacted with the one or more TGFβ/Activin-Nodal inhibitor for at least, or up to, 1, 2, 3, 4, 5, 6, 7, 8, 9, 10, 11, or 12 days or more. In certain embodiments, the organizer/aggregate complex is contacted with the one or more TGFβ/Activin-Nodal inhibitor for up to, or up to, at least 6, 7, or 8 days.

In certain embodiments, the organizer/aggregate complex is contacted with the one or more Wnt inhibitor at a concentration of between about 0.5 and about 25 nM, between about 1 and about 25 µM, between about 1.5 and about 20 µM, between about 2 and about 18 µM, between about 2.5 and about 15 µM, between about 3 and about 10 µM, between about 3.5 and about 9 µM, between about 4 and about 8 µM, between about 4.5 and about 6 µM, or about 5 µM.

In certain embodiments, the organizer/aggregate complex is contacted with the one or more Wnt inhibitor ata concentration of at least about 0.5, 1, 1.5, 2, 2.5, 3, 3.5, 4, 4.5, or 5 µM or more.

In certain embodiments, the organizer/aggregate complex is contacted with the one or more Wnt inhibitor for at least, or up to, about 1, 2, 3, 4, 5, 6, 7, 8, 9, 10, 11, or 12 days or more. In certain embodiments, the organizer/aggregate complex is contacted with the one or more TGFβ/Activin-Nodal inhibitor for up to, or up to, at least 6, 7, or 8 days.

In certain embodiments, the organizer/aggregate complex is contacted with the one or more BMP inhibitor, one or more Wnt inhibitor, and one or more Wnt inhibitor concurrently, for at least, or up to, about 1, 2, 3, 4, 5, 6, 7, 8, 9, 10, 11, or 12 days or more. In certain embodiments, the organizer/aggregate complex is contacted with the one or more BMP inhibitor, one or more Wnt inhibitor, and/or one or more Wnt inhibitor concurrently for up to, or up to, at least about 6, 7, or 8 days. In certain embodiments, the organizer/aggregate complex is contacted with one or more BMP inhibitor at a concentration of about 100 nM, one or more Wnt inhibitor at a concentration of about 10 µM, and one or more Wnt inhibitor of about 5 µM concurrently.

In certain embodiments, the organizer/aggregate complex can be embedded in matrigel after about 1, 2, 3, 4, 5, 6, 7, 8, 9, 10, 11, or 12 days of differentiation to promote neuroepithelial organization and outgrowth and to form a brain organoid. In certain embodiments, the organizer/aggregate complex can be embedded in matrigel after about 6, 7, or 8 days of differentiation to promote neuroepithelial organization and outgrowth and to form a brain organoid.

In certain embodiments, the organizer/aggregate complex is cultured in vitro in medium for at least about 10, 15, 20, 25, 30, 35, 40, 45, 50, 55, 60, 65, or 70 days to form a topically organized brain organoid. In certain embodiments, the organizer/aggregate complex is cultured in vitro in medium for at least about 20 days to form a topically organized brain organoid. In certain embodiments, the organizer/aggregate complex is cultured in vitro in medium for up to about 40, 45, 50, 55, 60, 65, 70, 75, 80, 85, 90, 95, 100, 105, 110, 115, or 120 days to form a topically organized brain organoid. In certain embodiments, the organizer/aggregate complex is cultured in vitro in medium for up to 70 days to form a topically organized brain organoid. In certain non-limiting embodiments, the organizer can be "deactivated" once the desired differentiation has been achieved. For example, where the organizer inducibly or conditionally expresses organizing agent, the inducing agent or condition can be withdrawn. Alternatively, if the organizer cells contain an inducible suicide gene, the suicide gene can be induced to result in death or senescence of the organizer cell. Further, in non-limiting embodiments, an organizer can be physically separated from the brain organoid. Brain organoids prepared by the foregoing method may therefore, in non-limiting embodiments, can comprise a deactivated organizer or lack a functional organizer.

In further non-limiting embodiments, the present disclosure provides for a method of generating a brain organoid having multiple eye fields comprising introducing, into a brain organoid prepared as set forth above, an organizer that expresses and secretes SHH along the midline of the organoid in an amount effective in producing more than one eye-field.

In further non-limiting embodiments, the present disclosure provides for producing therapeutically useful populations of cells comprising preparing brain organoids as described herein and harvesting, from those organoids, cells or tissue having a therapeutically useful phenotype, which may be used in cell-based therapy. Such cells and/or tissue may be separated from the brain organoids manually and/or by cell sorting methods (based, for example, on antigen expression). The present invention has far-reaching applicability for the generation of many different types of cells from human embryonic stem cells that could be used for cell-replacement therapy. The present disclosure demonstrated the ability to generate multiple neural cell types in 3D culture. A critical roadblock that cell therapy companies will face as they move their products from the laboratory to the clinic will be establishing high-quality methods of commercial-scale cell production. The method of cell production should meet at least three criteria: scale, precision, and cost. A method of cell production based on this invention could meet all three criteria:

A) Scale: Scale refers to the ability to reliably expand the quantity of cells from a small production setting to a large production setting. Current methods of cell production are based on traditional cell culture technique in which cells are grown on and adhere to plastic tissue culture dishes. Scaling such methods is often impractical, as one needs to maintain hundreds or even thousands of individual tissue culture dishes. The process is time-consuming, expensive, and difficult to quality control. In contrast, this invention cultures cells in suspension (i.e. floating in culture medium). Suspension culture allows cells to be grown in bio-reactors, which are large vats that support the growth of volumes of tissue. Bio-reactors are preferred over adherent tissue culture dishes for commercial-scale production of monoclonal antibodies, which rely on cell culture.

B) Precision: Many cell types in the body, especially in the nervous system, are specified by fine gradations of a signaling factor (i.e. a protein gradient). For example, the spinal cord contains at least 5 major cell-types that are differentiated only by small gradations in the levels of Sonic Hedgehog signaling protein they encounter. In traditional monolayer cell culture, it is often difficult to reproducibly achieve the exact signaling level required for a specific cell type, resulting in batch-to-batch variability. This invention, which relies on a gradient of organizing agent, allows the desired signaling level to be achieved at some place in the culture. Subsequent purification methods can be used to capture the desired cell type from the heterogeneous culture.

C) Cost: One of the most significant sources of cost in cell production from human embryonic stem cells is purchasing large quantities of clinical-grade recombinant growth factors (e.g. Sonic Hedgehog, FGF, and WNT). In this invention, most, if not all, recombinant proteins required for cell production are genetically encoded within cells of the tissue culture, and thus do not need to be added to culture medium. This significantly reduces cost of production.

5.3 Topographically-Organized Brain Organoids

In certain non-limiting embodiments, the present disclosure provides compositions comprising an organoid, such as a brain organoid, which is asymmetrical in at least one, at least two, or three dimensions.

In certain non-limiting embodiments, the present disclosure provides compositions comprising an organoid, such as a brain organoid, prepared according to a method described in the preceding section.

In certain non-limiting embodiments, the present disclosure provides compositions comprising a brain organoid comprising topographically patterned 3-dimensional neural tissue having an anterior region (forebrain) and a posterior region (hindbrain)

In certain non-limiting embodiments, the present disclosure provides compositions comprising a brain organoid comprising an organizer, as described above, in apposition to an aggregate of undifferentiated or partially differentiated stem cells to form an organizer/aggregate complex. In related non-limiting embodiments, the present disclosure provides a brain organoid prepared from said organizer/aggregate complex by culturing said organizer/aggregate complex in vitro under differentiating conditions, comprising cells having different phenotypes at different distances from the organizer.

In certain non-limiting embodiments, the organoid comprises cells that are human or non-human cells. Non-limiting examples of non-human cells include non-human primate cells, mouse cells, rat cells, hamster cells, rabbit cells, dog cells, cat cells, horse cells, etc.

In certain non-limiting embodiments, the stem cells ("SCs") are embryonic stem cells ("ESCs") or induced pluripotent stem cells ("iPSCs"). In certain embodiments, the stem cells are pluripotent stem cells or multipotent stem cells. In certain non-limiting embodiments, the stem cells are pluripotent stem cells. In certain non-limiting embodiments, the stem cells are maintained in hESC medium, for example Essential 8 medium (Life Technologies). In certain non-limiting embodiments, the stem cells can be partially differentiated prior to formation of the aggregate or prior to contacting with the organizer. In certain non-limiting embodiments, one or more stem cell comprised in the organoids described herein contain a heterologous nucleic acid, for example, but not limited to, a nucleic acid encoding, in expressible form, an organizing agent; a nucleic acid encoding, in expressible form, a detectable reporter molecule such as, but not limited to, a fluorescent protein or luciferase; or a nucleic acid encoding a differentiation factor or growth factor or transcription modulator.

In certain non-limiting embodiments, the organizing agent is a protein. In certain non-limiting embodiments, the protein is a Sonic Hedgehog Protein ("SHH"), which, for example, may be of the same species as the cells comprised in the aggregate. In certain non-limiting embodiments, where an organoid includes human cells, the organizing agent is of human origin. For example, the organizing agent can be a human SHH. In certain non-limiting embodiments, the protein is a SHH protein agonist or a protein that induces a SHH protein expression or promotes its activity. In certain non-limiting embodiments, the organizing agent is an agent that activates TGFβ/Nodal signaling. In certain non-limiting embodiments, the organizing agent is a FGF. In certain embodiments, the organizing agent is a FGF8b. In certain non-limiting embodiments, the organizing agent is FGF2. In certain non-limiting embodiments, the organizing agent is Wnt activator. In certain embodiments, the organizing agent is WNT7a. In certain non-limiting embodiments, the organizing agent is WNT3a. In certain non-limiting embodiments, the organizing agent is WNT1. In certain non-limiting embodiments, the organizing agent is retinoic acid. In certain non-limiting embodiments, the organizing agent is an agent that promotes the expression of a transcription factor SIM2. In certain non-limiting embodiments, the organizing agent is an agent that promotes the expression of a transcription factor FOXA2. In certain non-limiting embodiments, the organizing agent is an SHH homolog, for example Indian Hedgehog ("IHH") or Desert Hedgehog ("DHH"). In certain non-limiting embodiments, the organizing agent is a small molecule activator of the hedgehog pathway, such as, but not limited to, smoothened agonist ("SAG") or retinoic acid.

In certain non-limiting embodiments, the organizer comprises a cell or group of cells that express(es) and secrete(s) an organizing agent. In certain non-limiting embodiments, the organizer is a cell or cells that express(es) and secrete(s) a Sonic Hedgehog protein. In certain non-limiting embodiments, the cells are engineered to express and secrete an organizing agent. In certain non-limiting embodiments, the cells are engineered to express and secrete a SHH. In certain non-limiting embodiments, the organizer comprises ESCs that are engineered to express and secrete a SHH. In certain non-limiting embodiments, expression of organizing agent is inducible or conditional. In certain non-limiting embodiments, the organizer is a bead or beads containing organizing agent in sustained release form. In certain non-limiting embodiments, the organizer is a bead or beads comprising SHH in a sustained release form.

In certain non-limiting embodiments, the organizer may be comprised of cells that conditionally express organizing agent. For example, the organizer may be comprised of cells that conditionally express a SHH. For example, the organizer may be comprised of hESCs that conditionally express a hSHH when cultured in the presence of the small molecule doxycycline. To generate this cell line, a bicistronic gene cassette can be inserted into the AAVS1 locus of a human pluripotent stem cell line. The gene cassette can comprise 1) a constitutively expressed reverse tetracycline transactivator (rTTa), and 2) a gene coding for a protein (e.g. SHH, FGF, WNT, TGFbeta), that is expressed under the control of a tetracycline response element (TRE). The human pluripotent stem cell line can be marked with a fluorescent reporter protein, such as RFP. The gene cassette can be inserted into the AAVS1 locus via targeted genome editing (e.g. TALENs, CRISPR) (see FIG. 3A).

In certain non-limiting embodiments, the stem cell aggregate is formed prior to placing it in apposition to the organizer. In alternate embodiments, the aggregate is formed concurrently with apposition to the organizer. In still further non-limiting embodiments, the aggregate is formed subsequent to apposition to the organizer.

In certain non-limiting embodiments, the organizer is localized at a pole of the organoid. Organizing agent is released from the organizer to establish a gradient in the organoid as organizing agent diffuses away from the organizer source.

In certain non-limiting embodiments, more than one organizer can be placed in apposition to a stem cell aggregate (meaning that a plurality of distinct organizer (areas) are present, separated by a distance).

In certain non-limiting embodiments, the present disclosure provides compositions comprising a brain organoid comprising an organizer and comprising at least distinct forebrain and posterior regions. In certain non-limiting embodiments, said brain organoid comprises one or more of: a region having characteristics of the cerebral cortex; a region having characteristics of the hippocampus; a region having characteristics of the lateral ganglionic eminence ("LGE"); a region having characteristics of the medial ganglionic eminence ("MGE"); and/or a region having characteristics of the hypothalamus ("HtH"). In certain embodiments, the region having characteristics of the HtH comprises a region having characteristics of the anterior hypothalamic and a region having characteristic of the ventro-posterior hypothalamic. In certain non-limiting embodiments, said brain organoid comprises a PAX6-expressing region distinct from a NKX2.1-expressing region. In certain non-limiting embodiments, said brain organoid comprises a demarcated cortex-like region comprising cells expressing FOXG1 and/or PAX6. In certain non-limiting embodiments, said brain organoid comprises a demarcated LGE-like region comprising cells expressing GSH2 and contiguous to a region expressing PAX6. In certain non-limiting embodiments, said brain organoid comprises a demarcated MGE-like region comprising cells expressing NKX2.1 and FOXG1. In certain non-limiting embodiments, said brain organoid comprises a demarcated hypothalamus-like region comprising cells expressing NKX2.2 and NKX2.1. In certain non-limiting embodiments, said brain organoid comprises a forebrain-like region comprising, in order from dorsal to ventral: (i) a demarcated cortex-like region comprising cells expressing FOXG1 and/or PAX6; (ii) a demarcated LGE-like region comprising cells expressing GSH2 and contiguous to a region expressing PAX6; (iii) a demarcated MGE-like region comprising cells expressing NKX2.1 and FOXG1; and (iv) a demarcated hypothalamus-like region comprising cells expressing NKX2.2 and NKX2.1. In certain non-limiting embodiments, at least some of the cells of the brain organoid contain a heterologous (created by recombinant engineering) detectable reporter gene. In certain non-limiting embodiments, the organizer can be or can have been deactivated, ablated, or removed from any of the aforementioned brain organoids once its desired role in differentiation and topographical organization has been achieved.

In further non-limiting embodiments, the present disclosure provides a brain organoid comprising a midline organizer and having multiple eye fields.

In further non-limiting embodiments, the present disclosure provides compositions comprising a plurality of cells, prepared from brain organoids as described herein, and having a therapeutically useful phenotype. In certain non-limiting embodiments, the cells may be at least about 50 percent or at least about 60 percent or at least about 70 percent or at least about 80 percent or at least about 90 percent homogeneous based on phenotypic marker expression. For example, said phenotype may be a cortex phenotype, a hippocampus phenotype, a LGE phenotype, a MGE phenotype, a HtH phenotype, an anterior hypothalamic phenotype, a ventro-posterior hypothalamic phenotype. or a midbrain phenotype. In certain embodiments, the phenotype may be expression of either FOXG1 and PAX6; or GSH2; or NKX2.1 and FOXG1; NKX2.2 and NKX2.1; NKX2.2; or NKX2.1 but not FOXG1.

The foregoing compositions may further comprise cell culture medium, physiologic saline, or other medium appropriate for the maintenance of live cells. The foregoing compositions may optionally be cryogenically preserved.

5.4 Uses for Topographically-Organized Brain Organoids

In addition to their use as sources of cells for therapeutic application, topographically-organized brain organoids, as described herein, can be used as 3D tissue models for pre-clinical identification of drug toxicity: This invention provides access to complex, developmentally patterned human brain tissue, which can be used to test drugs for brain toxicity. For example, topographically patterned organoids are used to identify an unknown toxicity of statins (cholesterol lowering drugs) during early fetal brain development (see Example 6.2 and FIGS. 15-16)).

Topographically patterned organoids can be advantageously used for toxicology screening because they recapitulate critical features of the human brain that other cell and organoid models fail to capture. Specifically, they recapitulate the spatial positioning of individual brain regions, thus allowing the identification of complex brain malformations. On the other hand, current cell and organoid models would be limited to identifying changes in cell number and composition.

Similarly, brain organoids produced according to the invention may be used as 3D tissue models for drug discovery. For example, topographically patterned organoid could be generated with human stem cell lines harboring genetic mutations known to cause brain malformations. These disease organoids could be used to screen small molecule libraries to identify therapeutic compounds.

6. EXAMPLES

6.1 Generating Topographically-Organized Brain Organoids In Vitro

In native development in vivo, SHH is expressed from the ventral-most boundary of the developing neural tube, resulting in a ventral-high to dorsal-low gradient of SHH signaling. The gradient is dependent on native organizer tissue that expresses SHH protein (FIG. 2A). The experiments described below were designed to mimic this gradient in brain organoids in vitro. Among the goals were generating, in the organoids, properly organized brain regions that recapitulate those found in nature, including (dorsal to ventral): cerebral cortex, hippocampus, lateral geniculate eminence ("LGE"), medial geniculate eminence ("MGE"), and hypothalamus-like regions ("HtH") (FIG. 2B).

In order to produce the SHH gradient in vitro, an organizer tissue, or "organizer", was prepared: a human embryonic stem cell ("hESC") line was generated that inducibly expresses secretable SHH under the control of doxycycline. In particular, transcription activator-like effector nucleases ("TALENs") were used to insert a gene cassette into the AAVS1 locus of an RFP expressing hESC line. The reverse tetracycline transactivator (rtTA) is constitutively expressed from one allele, while human SHH is conditionally expressed under a tetracycline response element (TRE) (FIG. 3A). The hESC line expresses high levels of SHH mRNA, even more than SHH expressing floor plate tissue (D11 SHH CHIR) (FIG. 3B). Ectopically expressed SHH is biologically active, as demonstrated by its ability to induce FOXA2 expression (FIG. 3B).

hESC cells engineered to inducibly express and secrete human SHH were then embedded into one pole of a spheroid comprised of hESC cells (that had not been engineered to express SHH). This was achieved by a sequential aggregation procedure in which 1000 organizer cells were plated in a V-bottom low adhesion dish. Twenty-four hours later, 10,000 wildtype hESCs were plated on top of the organizer and allowed to aggregate for another 24 hours. The result is shown in FIG. 4, where the organizer is indicated as a fluorescent area (arrow).

It was then demonstrated that SHH organizer-containing organoids contained a SHH concentration gradient (FIG. 5). In the absence of doxycycline, there is no detectable SHH protein expression (top row). In the presence of doxycycline, SHH protein is expressed in a graded manner, that degrades as a function of distance from the organizer.

The resulting SHH organizer-containing organoids were then allowed to differentiate in culture, and demonstrated topographical organization that paralleled native brain regions. The SHH-organizer containing organoids were found to exhibit distinct dorsal and ventral domains. As shown in FIG. 6A, PAX6 and NKX2.1 are canonical proteins that delineate dorsal (PAX6) and ventral (NKX2.1) territories in the developing forebrain. In the baseline organoid protocol (no SHH organizer), the entire organoid is PAX6 positive, indicating dorsal identity (FIG. 6B). SHH induces NKX2.1 and suppresses PAX6 near the organizer (FIG. 6C), demonstrating the ability to organize tissue along the dorso-ventral axis. In addition, SHH organizer-containing organoids contain a cerebral cortex-like domain, as shown in FIG. 7A. The cerebral cortex is a brain region that controls higher cognition. In the brain, the cerebral cortex, which expresses PAX6 and FOXG1, resides in a region that is distal from the higher concentration of SHH (FIG. 7B). Similarly, in SHH pattered organoids, the PAX6+/FOXG1+ territory is distal to organizer (FIG. 7A).

SHH organizer-containing organoids were demonstrated to contain lateral ganglionic eminence territory (FIG. 8B). The lateral ganglion eminence ("LGE") is a brain region that gives rise to the striatum and expresses GSH2. The LGE territory is continuous with the cerebral cortex (PAX6) in vivo (FIG. 8A). In SHH organoids, the GSH2 territory is also continuous with the PAX6 territory, as seen in serial sections (FIG. 8B). Thus, the LGE exhibits an anatomically appropriate positioning in SHH organoids. SHH organizer-containing organoids also contain medial ganglionic eminence ("MGE") territory. The medial ganglion eminence (MGE) is a brain region that gives rise to cortical interneurons and expresses NKX2.1 and FOXG1 (FIG. 9A). The MGE is in the most ventral domain of FOXG1 expression in vivo. In SHH organoids, the MGE territory is also in the most ventral FOXG1 territory (FIG. 9B), exhibiting an anatomically appropriate positioning in SHH organoids.

In addition, SHH organizer-containing organoids contain hypothalamic territory (FIG. 10B). The hypothalamus (HtH) controls homeostatic functions in the brain and expresses NKX2.2 and NKX2.1 (FIG. 10A). The HtH is located proximal to, and overlapping with the source of SHH protein in the brain. This distribution is mirrored in SHH organoids (FIG. 10B), indicating proper topographic organization.

As shown in FIG. 11, positional identity within SHH organizer-containing organoids mimics in vivo forebrain anatomy. In SHH organoids, the FOXG1/PAX6 positive cortical territory (A, B, solid white arrows) is located distal to the SHH organizer (Top panel, dotted white arrows). In vivo, the FOXG1/PAX6 territory is also distal to the source of SHH. In SHH organoids, the NKX2.1 and NKX2.2 hypothalamic regions are proximal to, and overlapping with the SHH organizer (C, solid white arrows) as seen in vivo). In SHH organizer-containing organoids, the FOXG1/NKX2.1 positive territory resides in an intermediate domain, between the cortex and hypothalamus (B, white arrowhead). This positioning is also observed in vivo.

To summarize, SHH organizer-containing organoids contain multiple brain sub regions that are organized as a function of distance from the SHH source (left panel). The organization in SHH organoids matches what is observed in vivo in the human forebrain (FIG. 12).

It has further been shown that SHH can organize brain areas other than the forebrain (FIG. 13). SHH-containing organoids were differentiated without the presence of XAV939, a WNT-inhibitor that promotes anterior, forebrain identity. The removal of XAV939 allows organoids to assume a more posterior identity. Here, organoids were found to express OTX2 and FOXA2, and thus represent midbrain and posterior diencephalic territory. Like SHH forebrain organoids, these SHH midbrain organoids are organized in a topographic manner. FOXA2, which expressed in the most ventral part of the midbrain, is expressed proximal to the SHH organizer. Thus, the SHH organizer is a general strategy that can be used to organize multiple distinct brain areas (e.g. forebrain, midbrain, hindbrain, spinal cord).

SHH was observed to exhibit short and long-range signaling in the SHH-containing organoids. The SHH signal was found to be transmitted over 100 cell diameters, as indicated by activation of NKX2.1 expression and suppression of PAX6 expression (top panel of FIG. 14, 3D). When grown in standard monolayer cultures, the long-range signal is degraded, as diffusible SHH molecules dilute into the media. Still, a short-range signal that acts under 10 cell diameters from the SHH source remains (bottom panel of FIG. 14, 2D). The dual short-range and long-range activity of SHH is consistent with its known biology.

6.2. Use of SHH Organizer-Containing Organoids for Toxicology Testing

SHH-containing organoids were used in a series of experiments to study teratogenic potential of the widely used cholesterol lowering drugs known as statins. Cholesterol lowering statins are one of the most widely prescribed drugs in the US, and they are currently contraindicated in pregnancy. Some reports have identified an association between statins taken during pregnancy and adverse outcomes on the fetus, including limb abnormalities, intrauterine growth retardation, and CNS malformations, including rare cases of holoprosencephaly. All of these malformations are known to be associated with abnormal SHH signaling during embryonic development. However, other reports have not reproduced these findings.

To evaluate the effect of statins on fetal development, in certain embodiments SHH organizer-containing organoids are treated with statins. In certain embodiments, the SHH organizer-containing organoids are treated with cyclopamine, a drug that inhibits the SHH receptor smoothened, and AY9944, a drug that inhibits DHCR7, the terminal step of cholesterol synthesis.

The results of these experiments are shown in FIGS. 15 and 16. Compared to control SHH organizer-containing organoids, cyclopamine treated organoids exhibited no SHH signaling, as the entire organoid is PAX6+ (FIG. 15). Treatment with AY9944 (DHCR7i) or statins largely blocked SHH signaling, as the majority of the SHH organoid remained PAX6+ (FIG. 15), and SHH-induced genes, NKX2.2 and GSH2 were not expressed. Interestingly, the organizer remained NKX2.1 positive, suggesting that short-range signaling is still intact in the presence of cholesterol inhibitors.

FIG. 16 summarizes the effects of cholesterol inhibition on SHH organizer-containing organoids. Cholesterol synthesis inhibitors statins and DHCR7i were found to block long-range SHH signaling, but not short range signaling (middle panel). Cyclopamine, a SHH signaling antagonist, was found to block all SHH signaling.

6.3 Effect of SHH Organizer on Eve Field Development

Experiments were performed to test the effects of an SHH organizer placed at the midline of a developing brain organoid. In vivo, the presence of midline SHH results in an eye field split, whereas the absence of SHH signal results in holoprosencephaly (FIG. 17). As shown in FIG. 18, an SHH organizer positioned in the midline of a developing brain organoid resulted in the presence of multiple eye fields after 40 days of treatment.

6.4 Specification of Positional Identity in Forebrain Organoids

Human brain organoids are self-organizing, three-dimensional neural tissues derived from pluripotent stem cells. While organoids recapitulate histological features of the human brain, they lack a reproducible topographic organization, which is fundamental to brain structure and function. During development, spatial topography is determined by the graded activity of signaling molecules, which are released from discrete signaling centers. The present study showed that introduction of a signaling center into forebrain organoids would specify the positional identity of neural tissue in a distance-dependent manner. This study presented a system to trigger a sonic hedgehog (SHH) protein gradient in developing forebrain organoids that enabled ordered self-organization along dorso-ventral and antero-posterior positional axes. SHH-patterned forebrain organoids established major subdivisions of the forebrain, and strikingly, these subdivisions were positioned with in vivo-like topography. Consistent with its behavior in vivo, SHH exhibited long-range signaling activity in organoids. Finally, the present study used SHH-patterned cerebral organoids as a tool to study the potential teratogenic effects of statins during early fetal brain development. Together, the present study identified inductive signaling as an effective organizing strategy to recapitulate in vivo topography in human brain organoids.

Human pluripotent stem cells (hPSCs) have the intrinsic capacity to self-organize into multicellular, organ-like structures called organoids[1,2]. Brain organoids recapitulate the cellular diversity and micro-architectural features characteristic of discrete brain regions, providing unprecedented opportunities to model human brain development and disease[3-5]. However, in these organoids, individual brain regions are ordered randomly, non-reproducibly and lack the characteristic in vivo anterior-posterior, dorso-ventral, and medio-lateral positioning that supports the emergence of complex brain structure and function[1,4,6]. The absence of a defined topography is a crucial shortcoming of current brain organoid technologies.

During development, topographic maps are generated by gradients of signaling activity across neural tissue which allow cells to acquire discrete regional identities as a function of their specific position[7,8]. Region-specific organoids attempt to overcome positional heterogeneity by restricting cellular identities to a single brain area such as the optic cup[9], adenohypophysis[10], forebrain[11], midbrain[12], or hindbrain[13], using bath-application of patterning factors[14]. More recently, several groups have created a dorso-ventral axis by fusing dorsal and ventral forebrain organoids[15-17]. While these strategies recapitulate some processes associated with long-range tissue interactions, such as cell migration, they fail to capture broader aspects of regional diversity encompassed by the human forebrain.

Figure 19A:
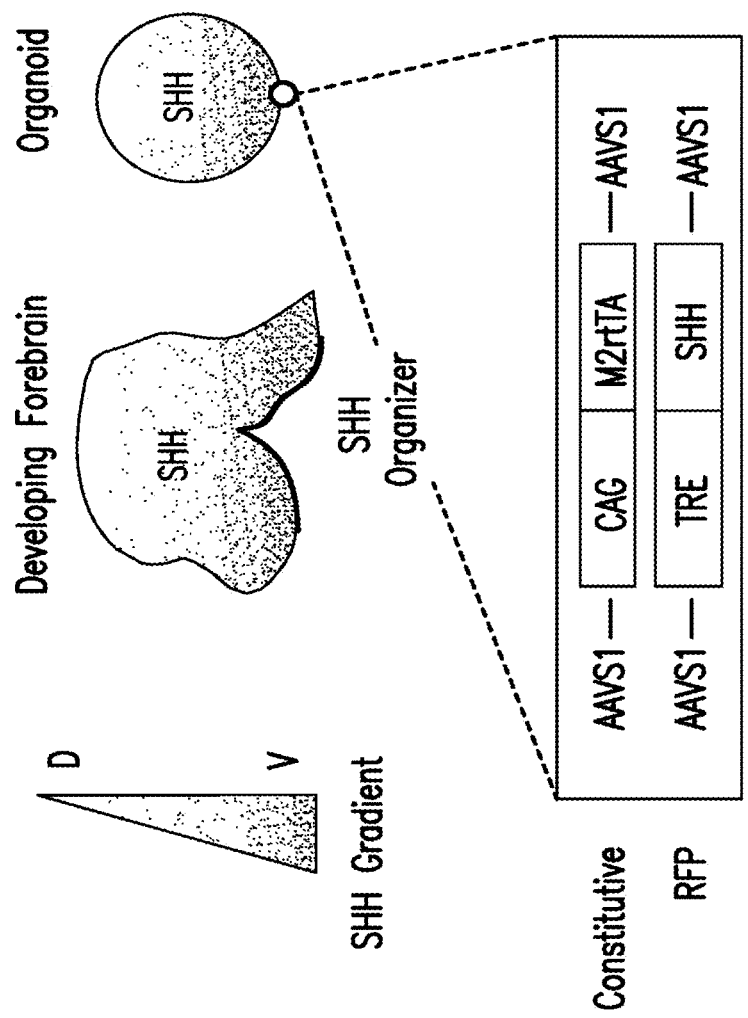
Figures 19B, 19C:
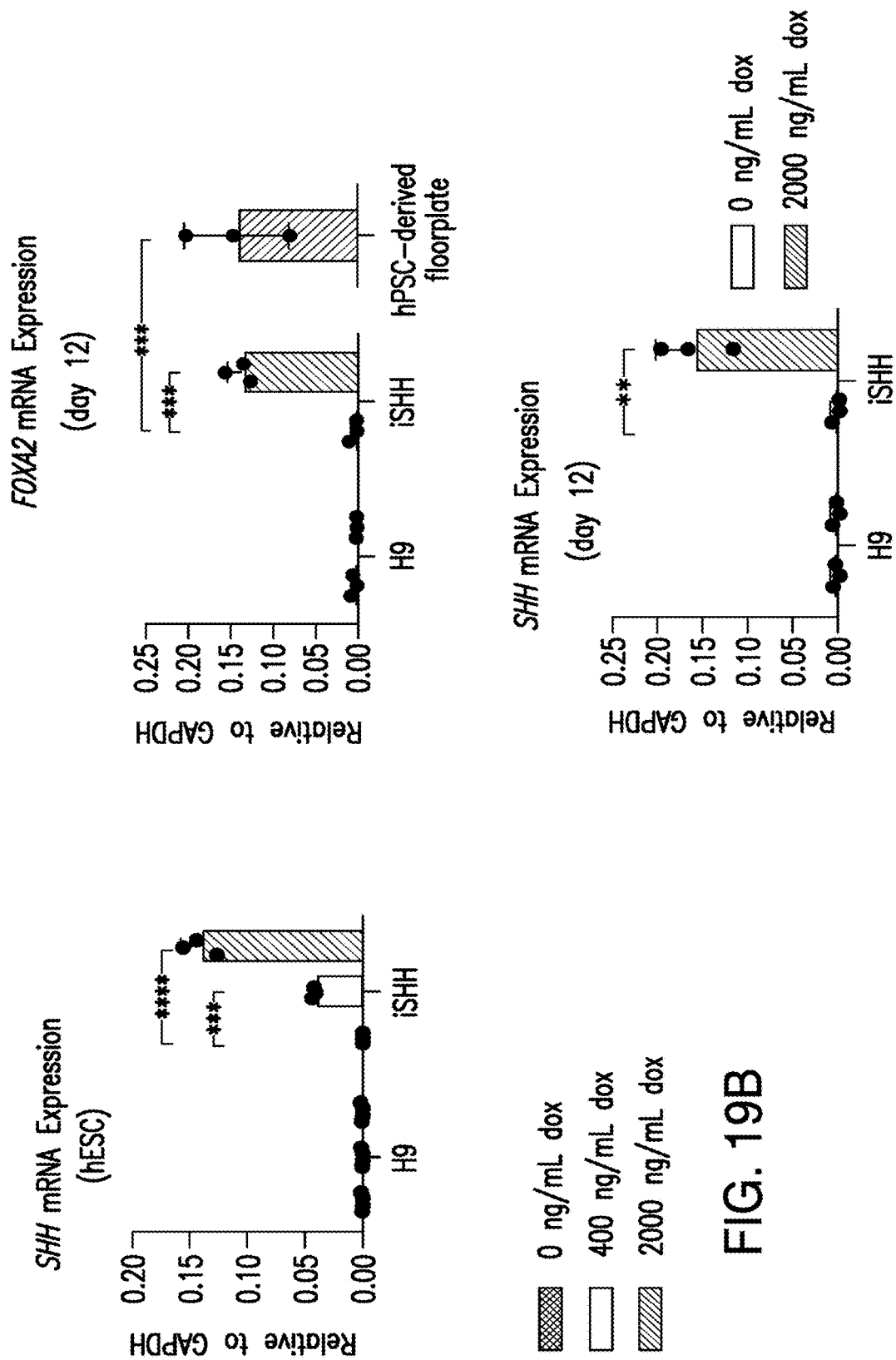
Figure 23A:
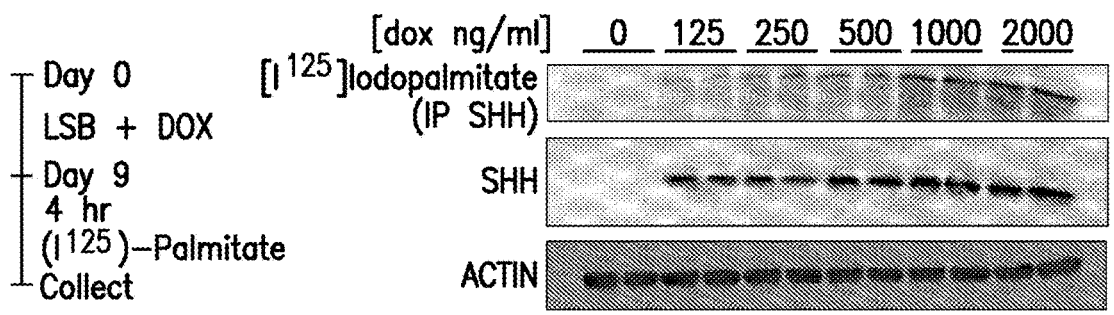

Sonic Hedgehog (SHH) is a signaling factor whose graded expression specifies the spatial organization of discrete progenitor domains across the neuraxis[18,19]. To test the hypothesis that introduction of a SHH signaling gradient into developing forebrain organoids could specify positional domains, the present study engineered an inducible SHH-expressing hPSC line (iSHH) that could be embedded at one pole of a developing organoid (FIG. 19A). The iSHH line was generated by TALEN-mediated gene targeting into the AAVS1 locus of an hPSC line with constitutive RFP expression[20,21]. A constitutively active reverse tetracycline transactivator is expressed from one allele of the AAVS1 locus, while full-length human SHH is expressed from the other allele, under the control of a tetracycline response element (TRE) (FIG. 19A). This strategy resulted in titratable SHH expression (FIG. 19B) and commensurate post-translational palmitoylation (FIG. 23A). The iSHH line induced robust expression of the SHH target gene FOXA2 during neural differentiation in the presence of doxycycline, indicating appropriate biological activity (FIG. 19C).

Figure 19D:
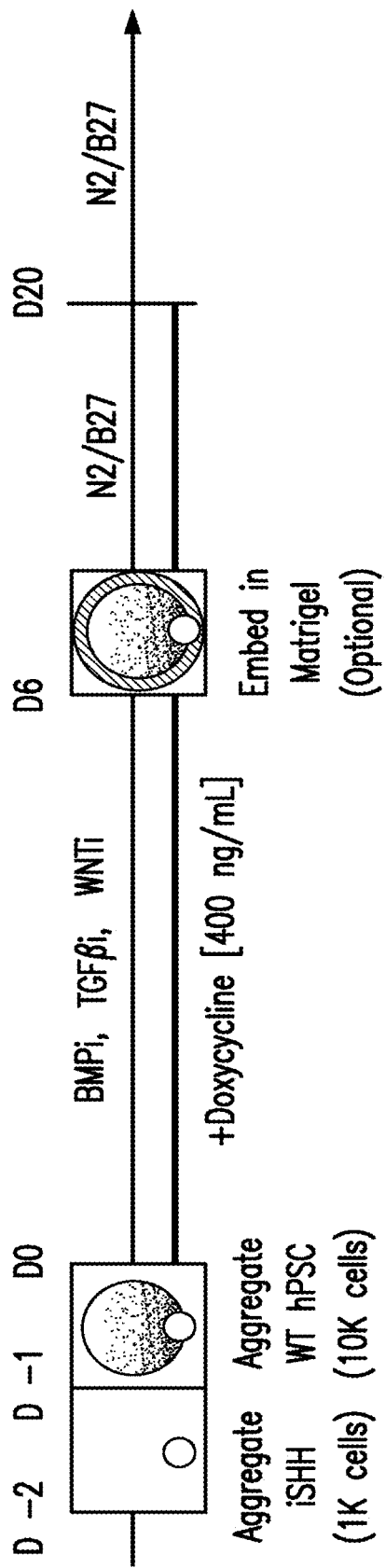
Figure 19E:
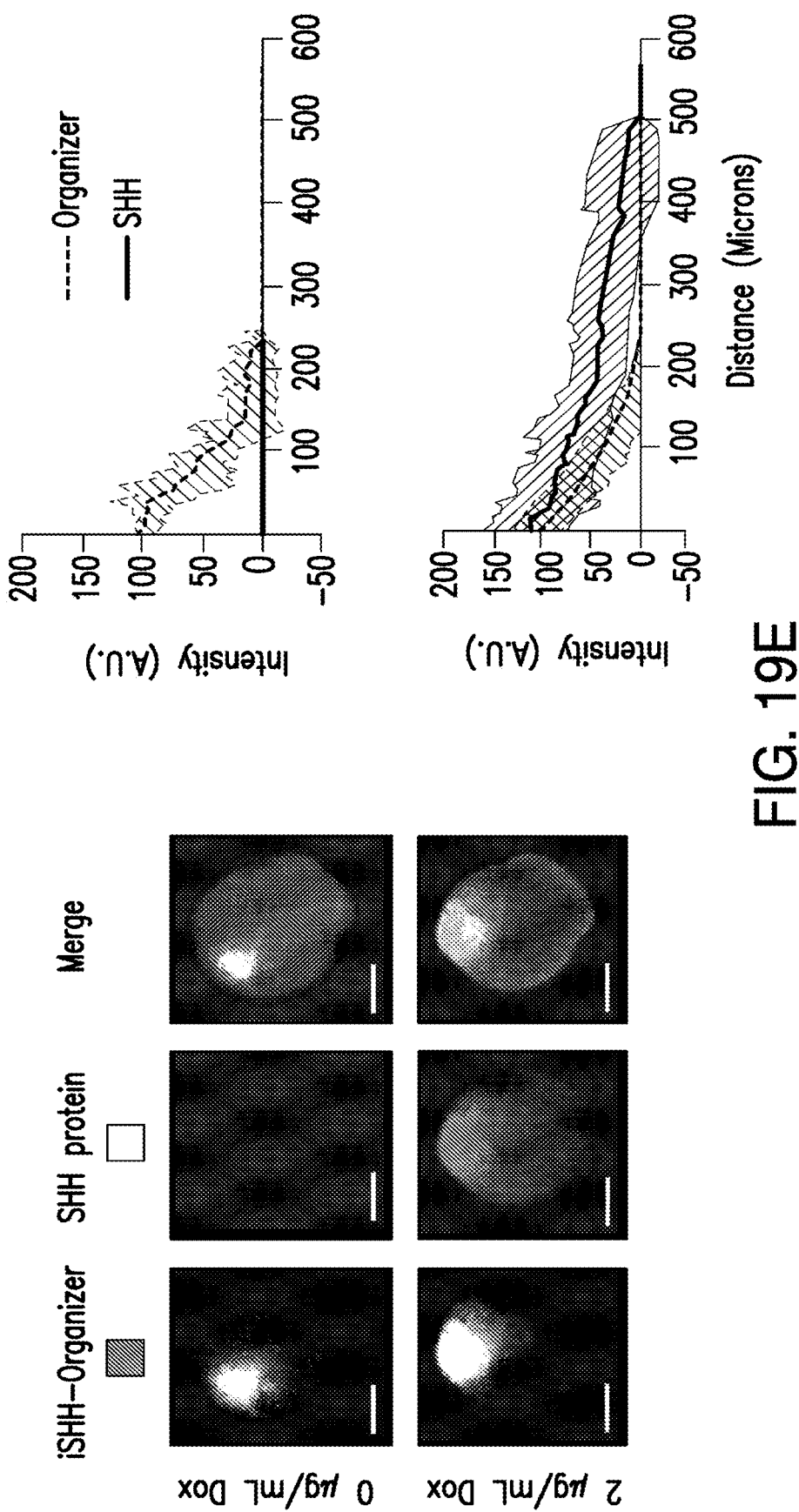
Figure 19F:
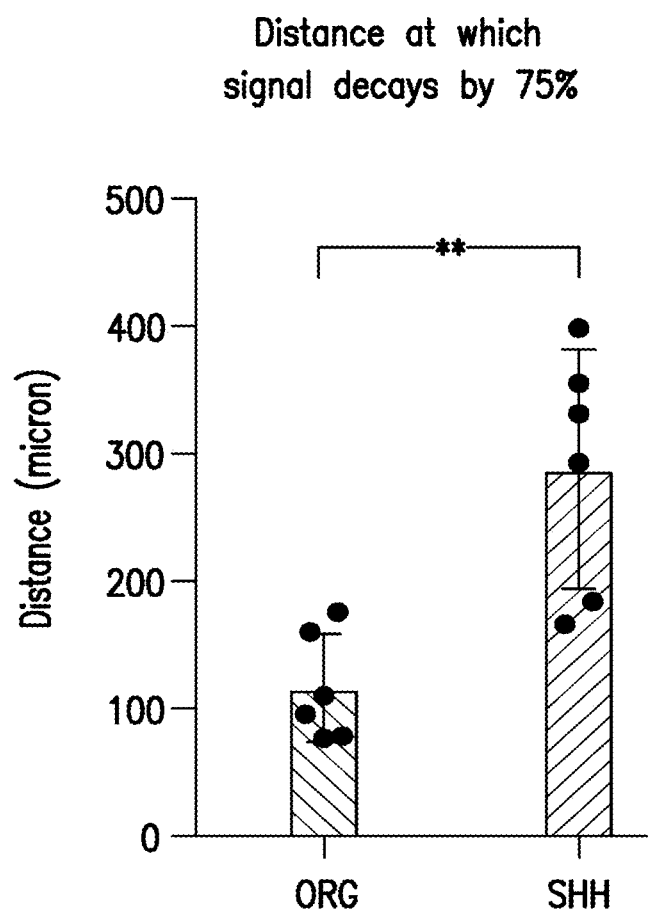
Figure 23B:
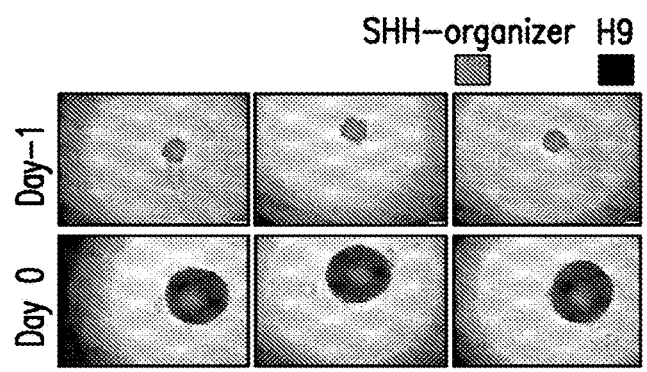
Figure 23C:
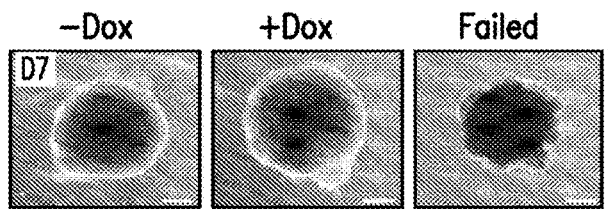
Figure 23D:
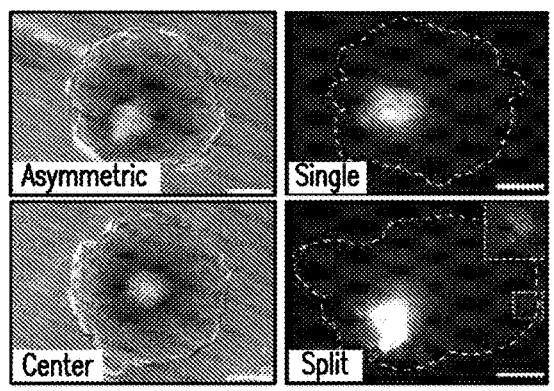
Figure 23D:
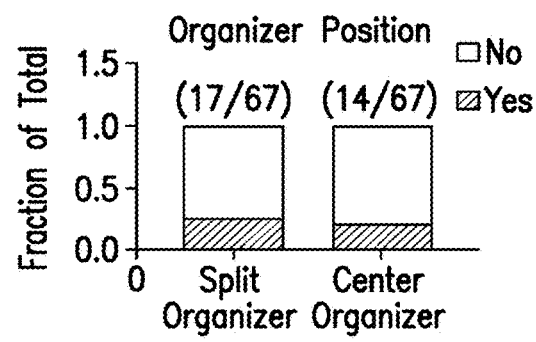

The present study next developed a method to embed iSHH cells at one pole of an hPSC spheroid, mimicking a developmental organizer. First, 1,000 iSHH cells were seeded in low-attachment round bottom microwells and allowed to aggregate for 24 hours (day −2 to −1). The next day 10,000 wild-type H9 hPSC were seeded on top of the iSHH cells (day −1 to 0) and allowed to aggregate for another 24 hours, reproducibly resulting in a chimeric iSHH-H9 spheroid in which a small cluster of iSHH cells are embedded within a larger spheroid (FIG. 23B, >90% efficiency). These chimeric 3D hPSC cultures were referred as SHH-spheroids in the present study. For the specific induction of forebrain identity, a strategy was devised that combined aspects of several previous organoid induction protocols. In brief, SHH-spheroids were cultured in the presence of inhibitors of TGFβ, BMP, and WNT (3-inhibitor protocol) for 6-8 days to promote specification of anterior forebrain identity[11]. After 6-8 days of differentiation, spheroids were embedded in matrigel droplets to promote neuroepithelial organization and moved to an orbital shaker upon outgrowth of neuroepithelial buds, which was typically 4-6 days[4,22] (FIG. 23C). Doxycycline (400 ng/ml) was added to the differentiation medium starting at day 0 to induce an asymmetric SHH signal (FIG. 19D). Under those conditions, the iSHH-organizer typically remained positioned at one end of the developing organoid, though it was observed small clusters of organizer cells separated from the main organizer in 25% of instances (FIG. 23D). To assess whether this strategy generates a gradient of SHH protein, immunocytochemistry was performed at day 4 of the differentiation. In the absence of doxycycline, no SHH protein was detectable. In the presence of doxycycline, high levels of SHH expression were detected in the region of the iSHH cells, and the abundance of SHH protein was quantified as a function of distance from the SHH-organizer (FIGS. 19E-19F).

Figure 19G:
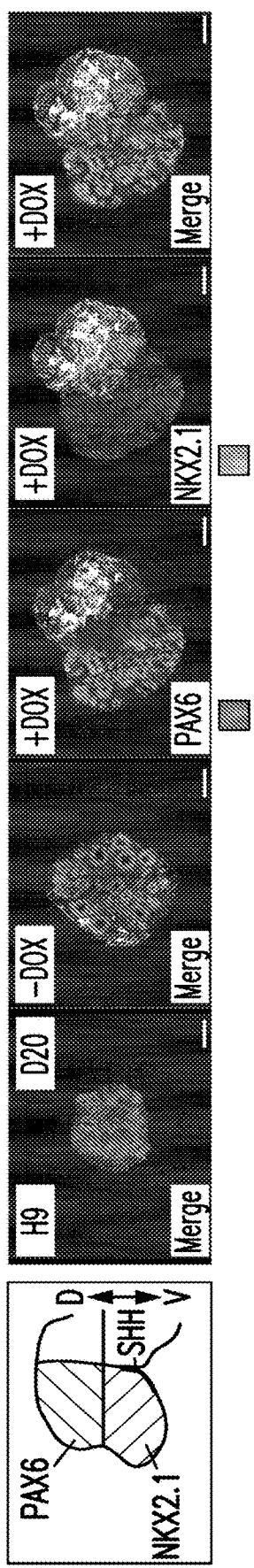
Figure 19H:
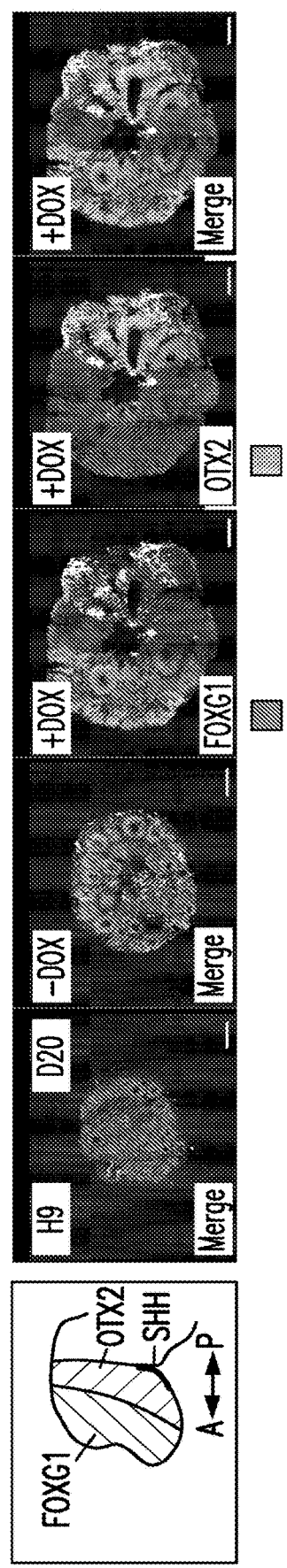
Figure 19I:
Figure 19J:
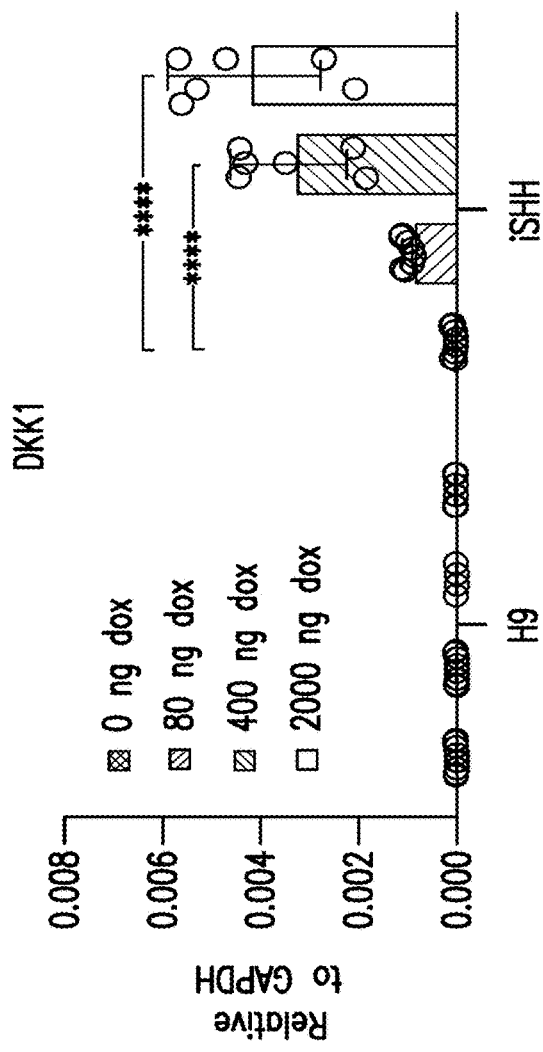

Functional subdivisions within the mammalian forebrain are located at discrete positions within a Cartesian coordinate system, whose axes are arranged in the dorso-ventral, medio-lateral, and antero-posterior directions. Each of the dorso-ventral and antero-posterior domains can be identified by the expression of characteristic transcription factors. PAX6 is expressed in the dorsal forebrain and NKX2.1 in the ventral forebrain (FIG. 19G). FOXG1 is expressed in the anterior forebrain, or telencephalon, while it is absent from the posterior forebrain, or diencephalon. In contrast, OTX2 is expressed in the diencephalon (FIG. 19H). When the present study differentiated H9 spheroids or SHH-spheroids in the absence of doxycycline they predominantly expressed PAX6 and FOXG1 within self-organized neuroepithelium, in agreement with previous findings[11] (FIGS. 19G-19H). This indicates that the default identity of the present 3D cultures is dorsal-anterior forebrain, which gives rise to the neocortex. SHH-spheroids grown in the presence of doxycycline (400 ng/ml) induced NKX2.1 near the organizer, while PAX6 expression was suppressed (FIG. 19G).

Surprisingly, FOXG1 expression was also suppressed near the organizer, while OTX2 expression was maintained (FIG. 19H), suggesting that SHH can lead to posterior forebrain specification. The present study therefore examined the expression of TCF7L2, which is expressed in the diencephalon[23,24] and SIX3[25], which is expressed in optic recess and hypothalamus, in SHH organoids. Both TCF7L2 and SIX3 were induced the near organizer tissue, supporting a role for SHH in anterior-posterior patterning, as well as dorsoventral patterning. SHH exhibited dose-dependent induction of DKK1 (FIG. 1j), a secreted antagonist that shapes the anterior-posterior WNT gradient in vivo, is commonly induced in regions of high WNT/β-catenin activity[26,27], and is a critical regulator of anterior-posterior patterning[28,29]. It is thus interesting to hypothesize that SHH might exert anterior-posterior patterning activity via regulation of WNT signaling[30].

Figure 20A:
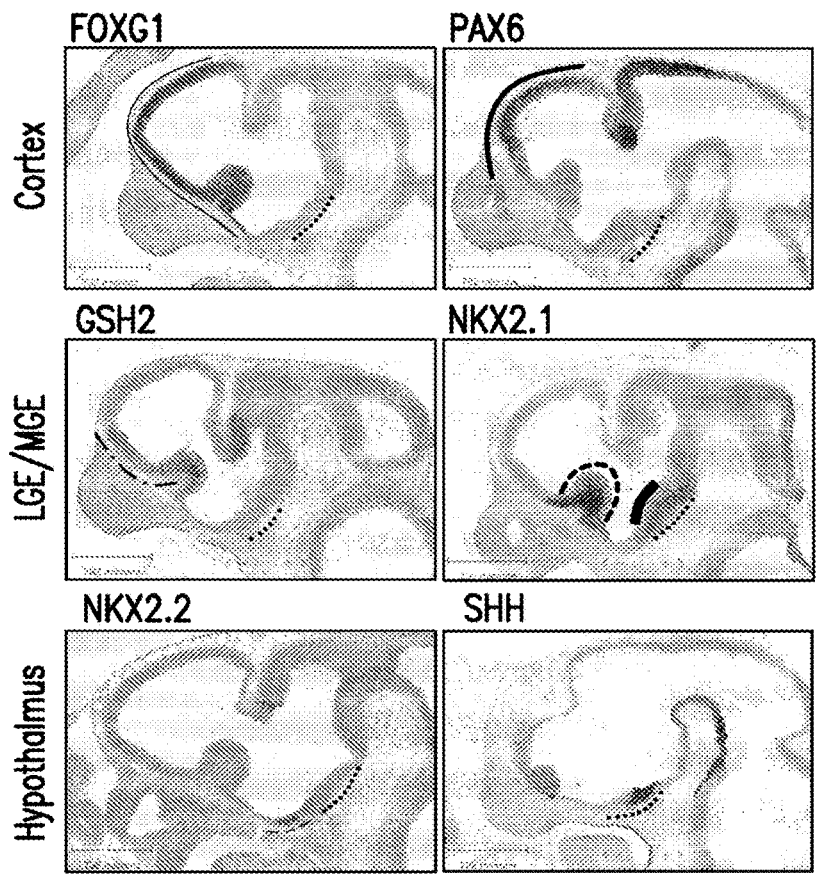

Given that a SHH protein gradient could specify distinct dorso-ventral and antero-posterior positional domains, it was next sought to determine if the resulting forebrain subdivisions are aligned according to an anatomically appropriate topography. The position of the presumptive forebrain subdivisions in vivo can be defined by their distance from the SHH source in the hypothalamus. The neocortex (PAX6+/FOXG1+) represents the anterior and dorsal subdivision of the forebrain which is located most distal from the SHH source. Just ventral to the neocortex is the lateral ganglionic eminence (LGE) characterized by the co-expression expression of GSH2+/FOXG1+, followed by the medial ganglionic eminence (MGE) characterized by co-expression of NKX2.1+/FOXG1+, the antero-dorsal hypothalamus characterized by expression of NKX2.2+, and finally the ventro-posterior hypothalamus characterized by the expression of NKX2.1+/FOXG1-, representing the brain region located most ventral and proximal to the SHH source (FIG. 20A).

Figure 20B:
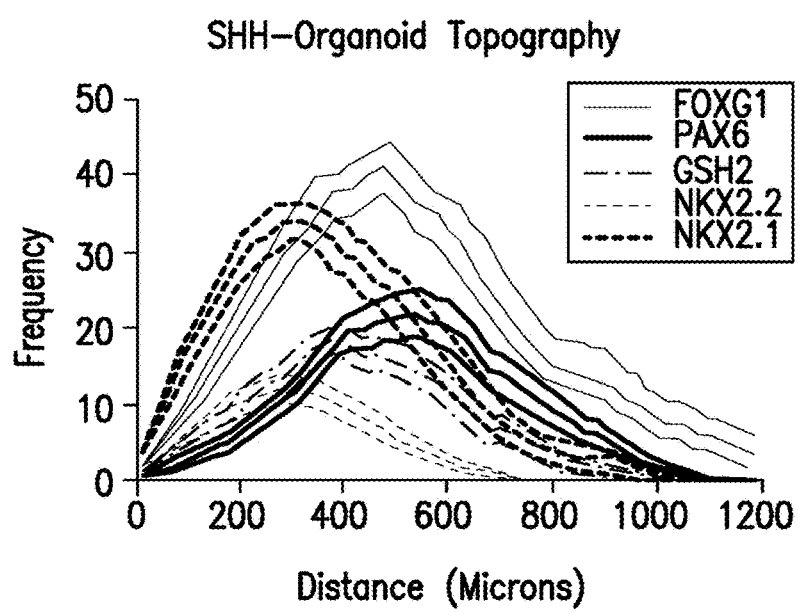
Figure 20C:
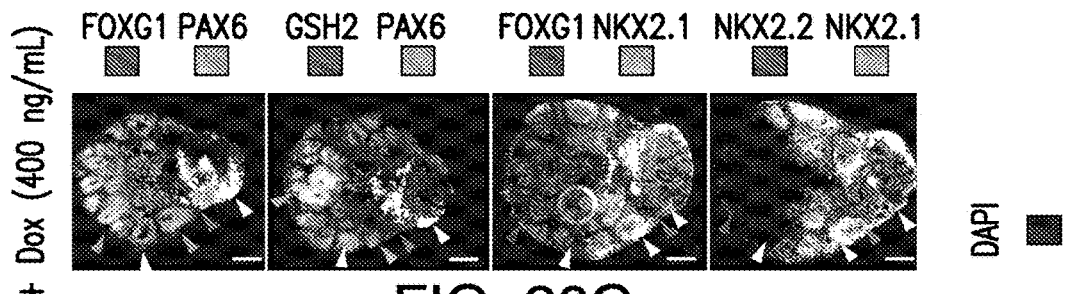
Figure 20D:
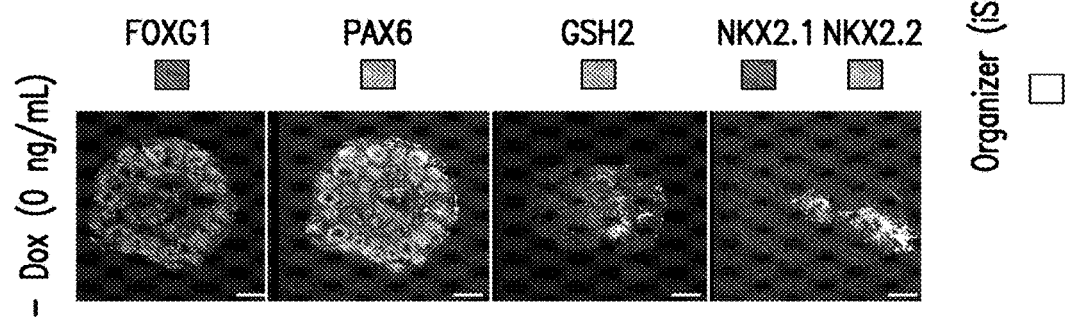
Figure 20E:
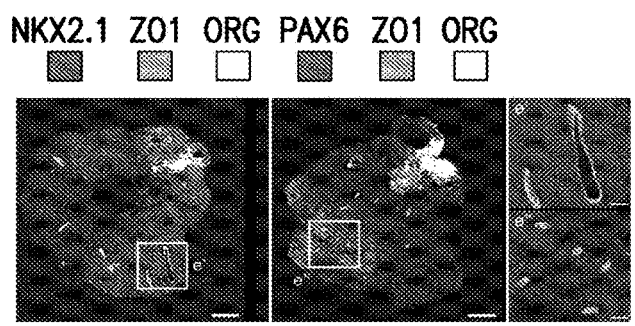
Figure 20E:
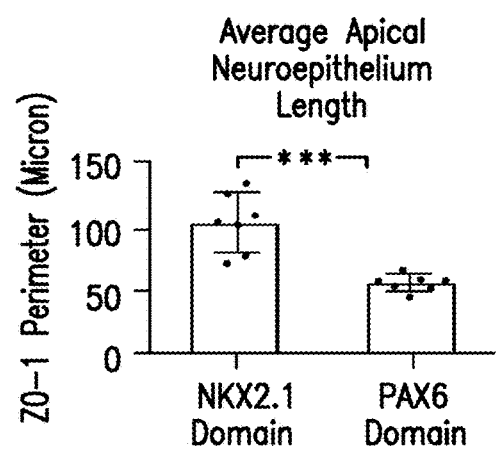

When differentiated in the presence of doxycycline (400 ng/ml), SHH-spheroids formed at least five topographically distinct presumptive forebrain domains. Quantification of the distance of forebrain domains from the SHH-organizer, identified by protein expression, revealed that the positioning of these domains mimics broadly the pattern observed in vivo (FIG. 20B). Topographic organization could be triggered in a similar manner in at least five additional hESC or iPSC lines using the same H9-based iSHH organizer, though the specific growth rates and size of regional domains could differ (FIG. 25). It was next identified presumptive neocortical (FOXG1+/PAX6+), LGE (GSH2+), MGE (FOXG1+/NKX2.1+), anterior hypothalamic (NKX2.2+) and ventro-posterior hypothalamic (NKX2.1+/FOXG1-) regions by immunocytochemistry (FIG. 20C). FOXG1 expression was absent from the organizer tissue itself, but robust expression of NKX2.1 was observed in at least a subset of the organizer cells, suggesting hypothalamic identity[31] (FIG. 26A). The resulting topographic patterning is in contrast to the patterning exerted by bath application of SHH agonist to forebrain organoids, which results in subpallium-restricted identities[15,16]. Topographic patterning could also be achieved in the absence of matrigel (FIG. 26B). SHH-spheroids differentiated in the absence of doxycycline expressed markers of dorsal-anterior forebrain, including PAX6 and FOXG1, with a small proportion of GSH2 expressing cells. These 3D cultures in the absence of doxycycline did not express the ventral identity genes NKX2.1 and NKX2.2 (FIG. 20D).

Interestingly, tissue cytoarchitecture differed between areas that are proximal (hypothalamic-like) and distal (telencephalic-like) to the SHH source. At day 20, PAX6+ distal neuroepithelia acquired circular, rosette-like morphologies (FIG. 20E, inset), consistent with the self-organizing radial structures described for forebrain organoids[4,11]. In contrast, the NKX2.1+ proximal region contained many thin and highly extended neuroepithelia (FIG. 20E, inset) as observed previously for 3D structures of early hypothalamic lineages[10,32]. This appears to be restricted to diencephalic NKX2.1+ regions, as presumptive MGE domains (FOXG1+/NKX2.1+) typically acquired circular, rosette-like morphologies (FIG. 20C, FIG. 26C). The present data indicate that an asymmetric SHH cue enables the ordered patterning and topographical organization of brain regions without interfering in the self-organization process, which leads to the establishment of region-specific tissue microarchitectures. These 3D cultures were referred as SHH-organoids.

Figure 27A:
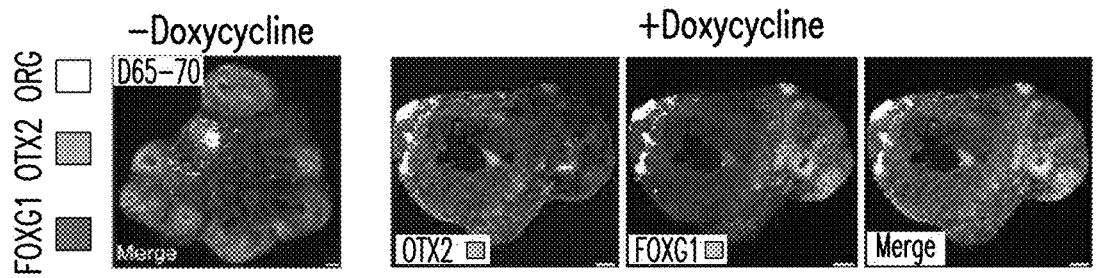
Figure 27B:
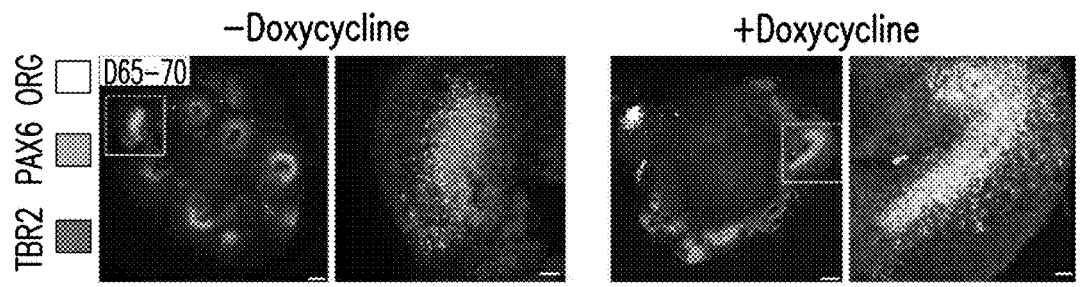
Figure 27C:
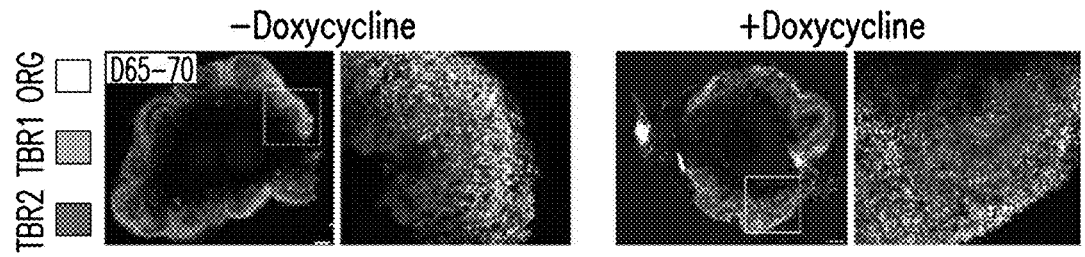
Figure 27D:
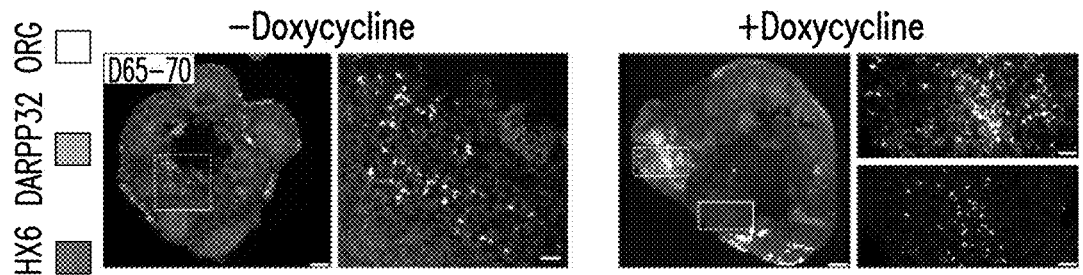
Figures 27E, 27F:
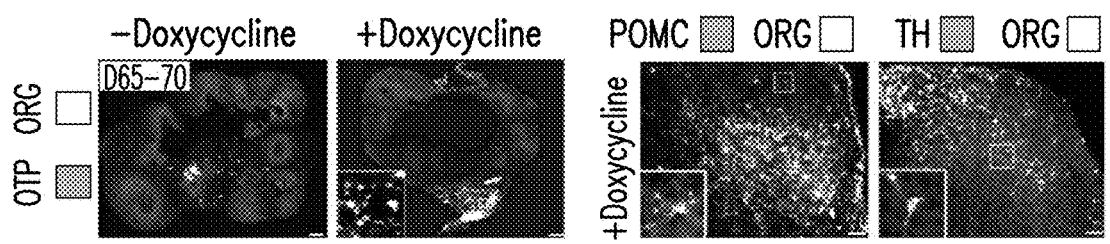

To explore the degree to which topography is maintained over time, SHH-organoids were cultured for up to 70 days. Whole-mount analysis by iDISCO clearing revealed that FOXG1+ and OTX2+ domains remained largely discrete at this stage. Typically, the OTX2+ domain was located proximal to the organizer, while the FOXG1+ domain was located distally (FIG. 27A). Radially organized PAX6, TBR2, TBR1 cerebral cortex-like tissue and DARPP32+ striatum-like tissue emerged in distal domains (Supplementary FIG. 5b-d), while hypothalamic-like tissue, expressing LHX6, OTP, POMC, and TH, was found in the immediate vicinity of the organizer cells (FIG. 27D-27F). In some instances, organoid topography was more difficult to discern because the organizer seemed to have dispersed throughout the tissue. In addition, tissue necrosis in the center of those larger organoids may degrade organization over time.

Figure 28D:
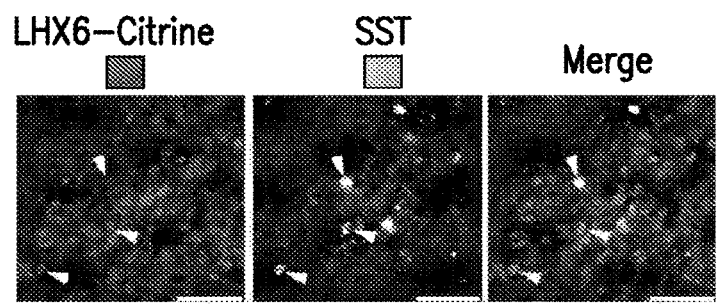
Figure 28E:
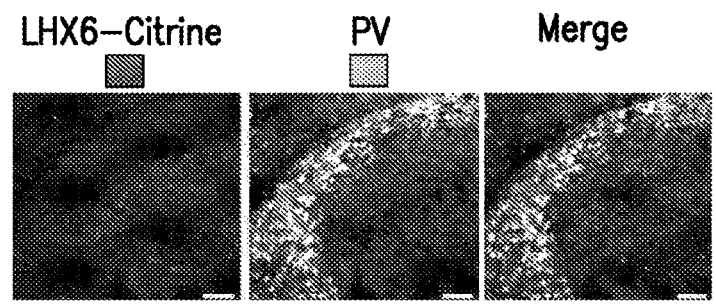
Figure 28F:
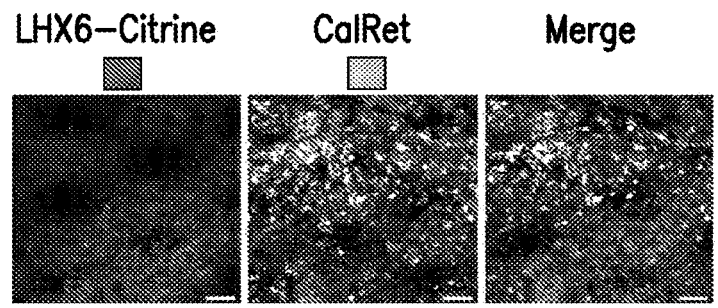

The identity of LHX6+ cells including the presence of cortical interneurons was further defined by differentiating SHH-organoids using an LHX6-citrine hPSC line. As expected, LHX6+, putative hypothalamic precursors, emerge near the organizer, with some cells co-expressing NKX2.1 (FIG. 28A). A subset of LHX6+ cells co-express FOXG1+ (FIG. 28B), while a subset are negative for FOXG1, suggesting the presence of both MGE and hypothalamic LHX6 lineages. Some FOXG1+/LHX6+ cells exhibit a leading-process morphology characteristic of migrating interneurons (FIG. 28C). Cells expressing somatostatin, parvalbumin, or calretinin were observed in SHH-organoids (FIGS. 28D-28F), suggesting the emergence of diverse interneuron populations. However, parvalbumin+ cells did not co-express LHX6 indicating that those PV+ cells many not represent cortical interneurons.

It was next sought insight into the mechanisms by which a SHH signaling gradient establishes forebrain topography. Using the suppression of PAX6 as a read-out of SHH signaling activity, the present study compared the radial extent of PAX6 suppression in 2D versus 3D cultures. High-dox conditions (2 mg/ml) were used in assessing SHH activity. In 3D cultures, it was observed the suppression of PAX6 expression at an average distance of 335±54 µm from the organizer tissue (FIG. 21A). Interestingly, this range is similar to the distances reported for SHH signaling in vivo based on studies across multiple tissues of the developing mouse or chick embryos[33-35]. However, in 2D cultures in which a similar 1:10 ratio of iSHH to wildtype cells is maintained, the present study saw suppression of PAX6 at much shorter average distances (75±31 µm) from the SHH source tissue (FIG. 21A).

The observation that the range of SHH signaling activity is restricted in 2D raises the question how SHH establishes long-range gradients in 3D. The present study generated 2 theoretical models based on known mechanisms of SHH signaling in vivo (FIG. 21B). The first model is a concentration-dependent model. In this model, SHH signaling activity is determined by the local concentration of SHH morphogen, and is dependent on mechanisms that can transport SHH protein over long distances, such as diffusion, facilitated transport, or cell-to-cell relay[33,35-39]. The second model is a temporal model. In this model, SHH signaling is restricted to tissue immediately adjacent to the source, which is relieved of SHH signaling as tissue grows away from the source[40]. Tissue that grows away from a SHH source will record a brief duration of signaling activity, while tissue that remains near the SHH source will record a long duration of signaling activity. This temporal model does not rely on transport of SHH over long distances.

To experimentally test these models, the iSHH organizer was embedded within a circumscribed ring of GFP-expressing hPSCs. This was achieved by sequential plating of 1,000 iSHH cells, followed by 1,000 GFP cells 8 hours later, followed by 10,000 H9 cells the next day. It was reasoned that if the activity of SHH extends past the GFP boundary, then this would support a long-range concentration dependent mechanism. On the other hand, if the GFP boundary expands coincident with the extent of SHH activity, this would support a temporal model, in which tissue growth rather than protein transport establishes long-range SHH activity (FIG. 21B). After growing SHH-GFP-organoids for 20 days in doxycycline (2 mg/ml), it was observed that the GFP expressing cells stay within 285±44 µm to the SHH organizer cells. The activity of SHH, determined as suppression of PAX6 expression, extends to 430±96 µm, thus extending past the green boundary (FIG. 21C). These data provide evidence for a concentration-dependent signaling mechanism in which SHH protein is transported long distances away from producing cells. Still, because the long-range SHH signal degrades in 2D culture, but a short-range signal persists, the present data do not exclude the possibility of a concurrent short-range signaling mechanism. In fact, during limb patterning, SHH is known to utilize both short- and long-range signaling mechanisms[41] and such an interplay of short- and long-range signaling may also be critical during forebrain development[31,42,43].

The reproducible topography of SHH-organoids might make them suitable to discern phenotypes related to the development and maldevelopment of forebrain morphogenesis. As proof-of-principle the present study sought to use SHH-organoids to study the potential adverse effects of statins during fetal forebrain development. Statins are among the most widely prescribed drugs and are known to lower cholesterol levels. Cholesterol is an integral component of the SHH pathway as both a post-translational ligand modification[36,44-46] and as an agonist of the smoothened receptor[47,48]. Interestingly, a retrospective case series examining birth defects associated with statin use during first trimester pregnancy found a high percentage of infants born with a range of adverse birth outcomes ranging from growth delay to limb, heart and CNS midline defects, which may be associated with reduced SHH signaling[49]. Subsequent follow-up studies did not observe the same effects in alternative cohorts[50-52]. F1 progeny of pregnant mice exposed to high-doses of statins typically exhibited fetal loss, neurologic, or skeletal abnormalities[53]. Thus, it remains an important, unresolved question whether statins can interrupt SHH-related signaling events during human embryonic development.

Figure 22A:
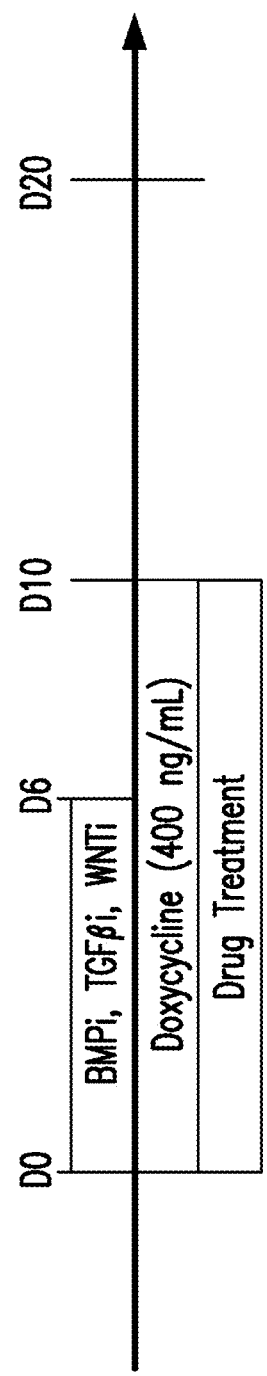
Figure 22B:
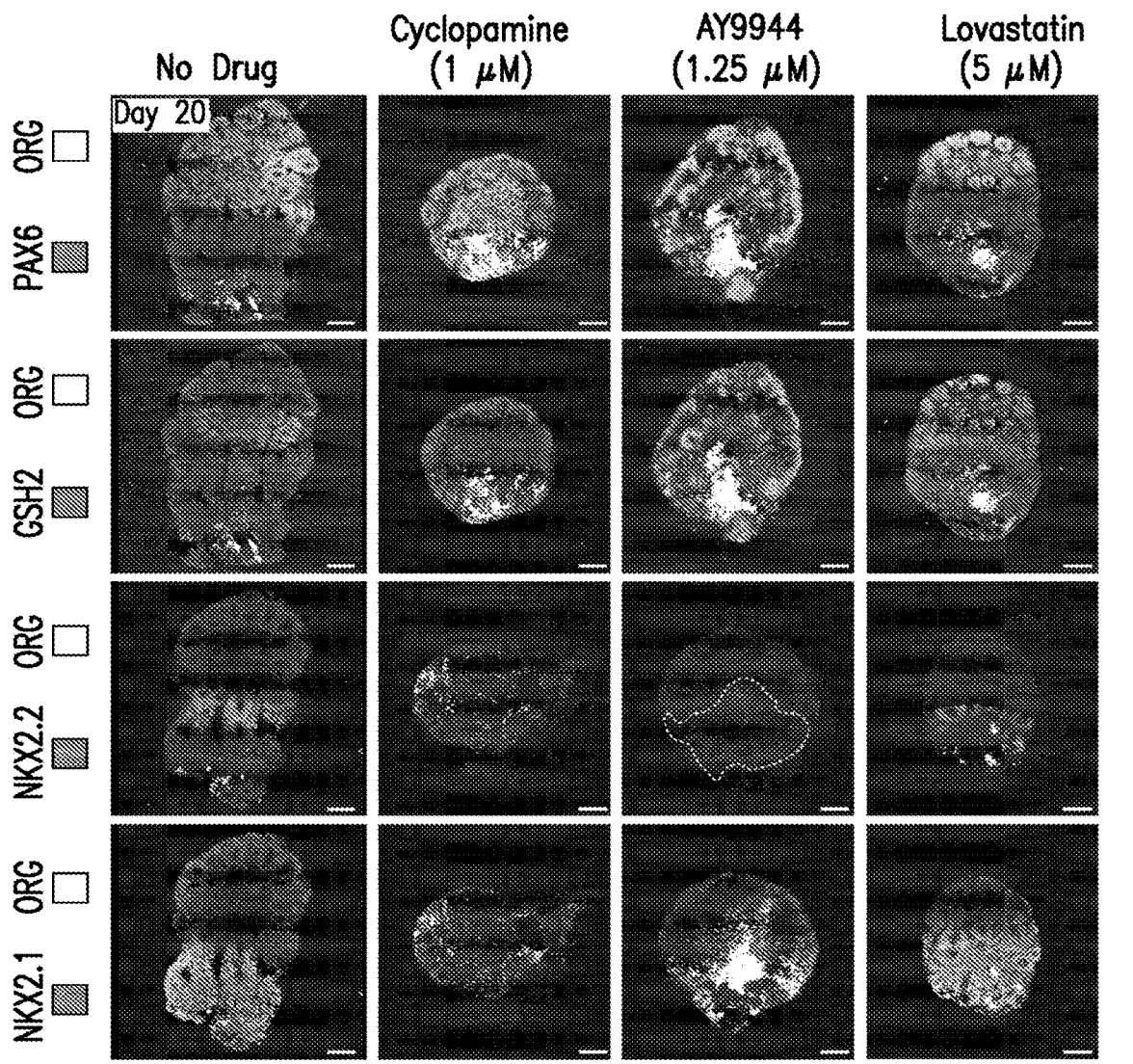
Figure 22B:
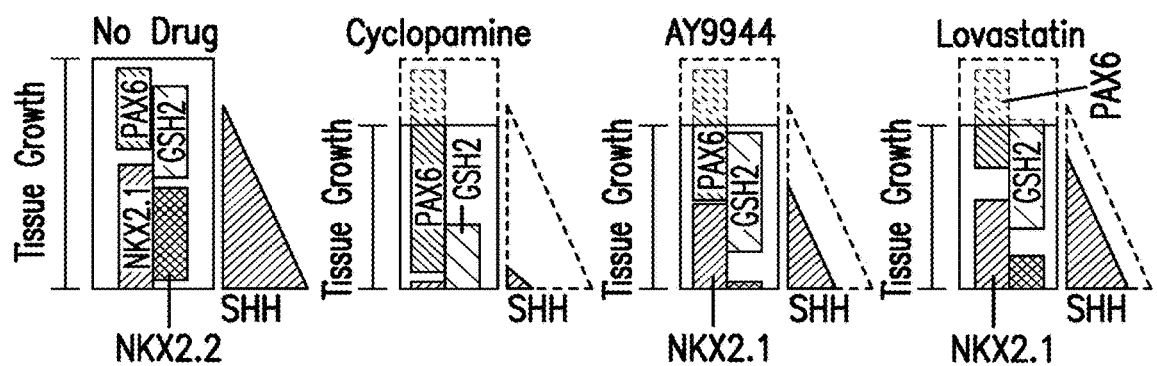
Figure 22C:
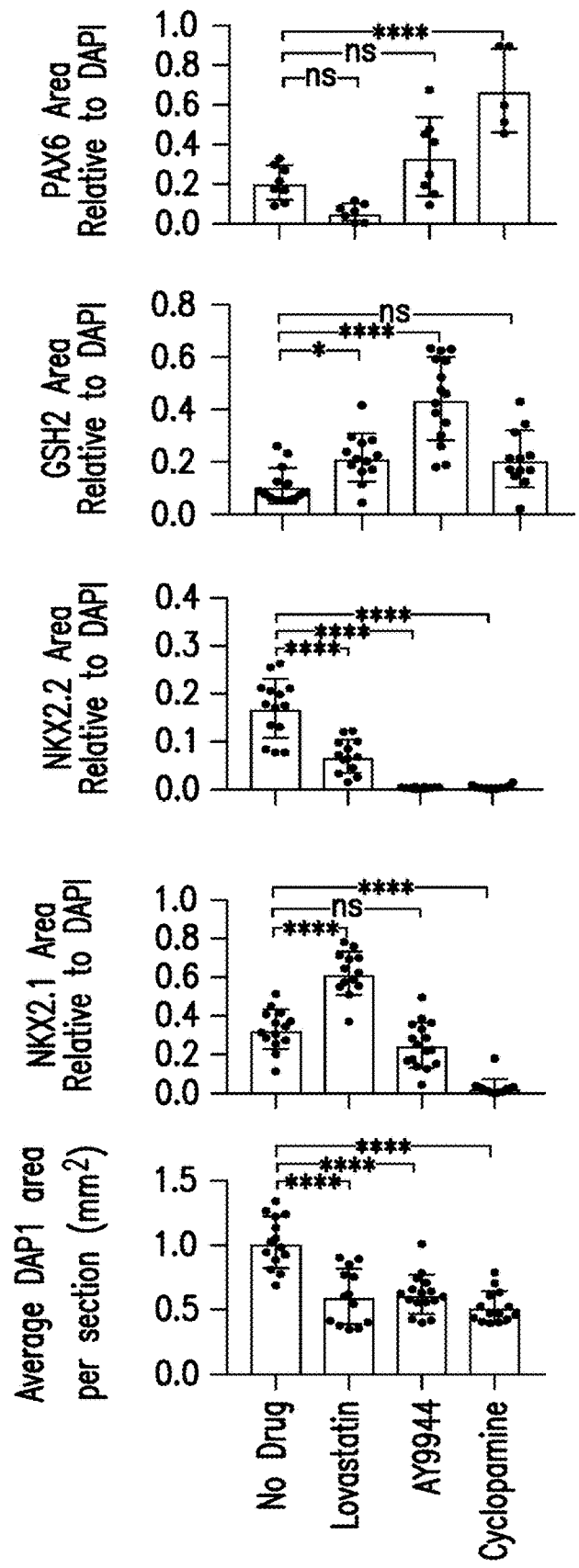

To test whether statins perturb fetal brain growth or patterning, SHH-organoids were treated with doxycycline (400 ng/ml) plus lovastatin (5 µM)[54] from day 0-10 of differentiation (FIG. 22A), and analyzed at day 20. The effects of AY9944 (1.25 µM)[54], a specific inhibitor of the 7-dehydrocholesterol reductase enzyme (DHCR7) that facilitates the terminal step of cholesterol synthesis, and cyclopamine (1 µM[55]) a Smoothened antagonist that blocks all SHH activity were also tested. In the no drug condition, SHH-organoids established distinct positional domains marked by the expression of PAX6, GSH2, NKX2.2, and NKX2.1 at discrete distances from the SHH-organizer (FIG. 22B). As expected, SHH-organoids grown in the presence of cyclopamine were nearly uniform for PAX6 expression consistent with inhibition of SHH signaling activity (FIGS. 22B-22C). AY9944 treatment reduced the efficacy and range of SHH signaling activity, shifting the organoid to a more dorsal identity. NKX2.2 induction was largely blocked, while cells just adjacent to the organizer expressed GSH2 and PAX6 (FIGS. 22B-22C). Lovastatin treatment caused similar but milder effects than AY9944. There was a partial block in NKX2.2 induction, with concomitant increase in GSH2 expression (FIGS. 22B-22C), consistent with a dorsal shift and reduction in the efficacy and range of SHH signaling activity. Interestingly, the organizer cells retained diencephalic NKX2.1 expression in the presence of AY9944 or lovastatin, but not cyclopamine (FIG. 29A), suggesting cholesterol synthesis-inhibition has minimal impact on local SHH activity.

Figure 22D:
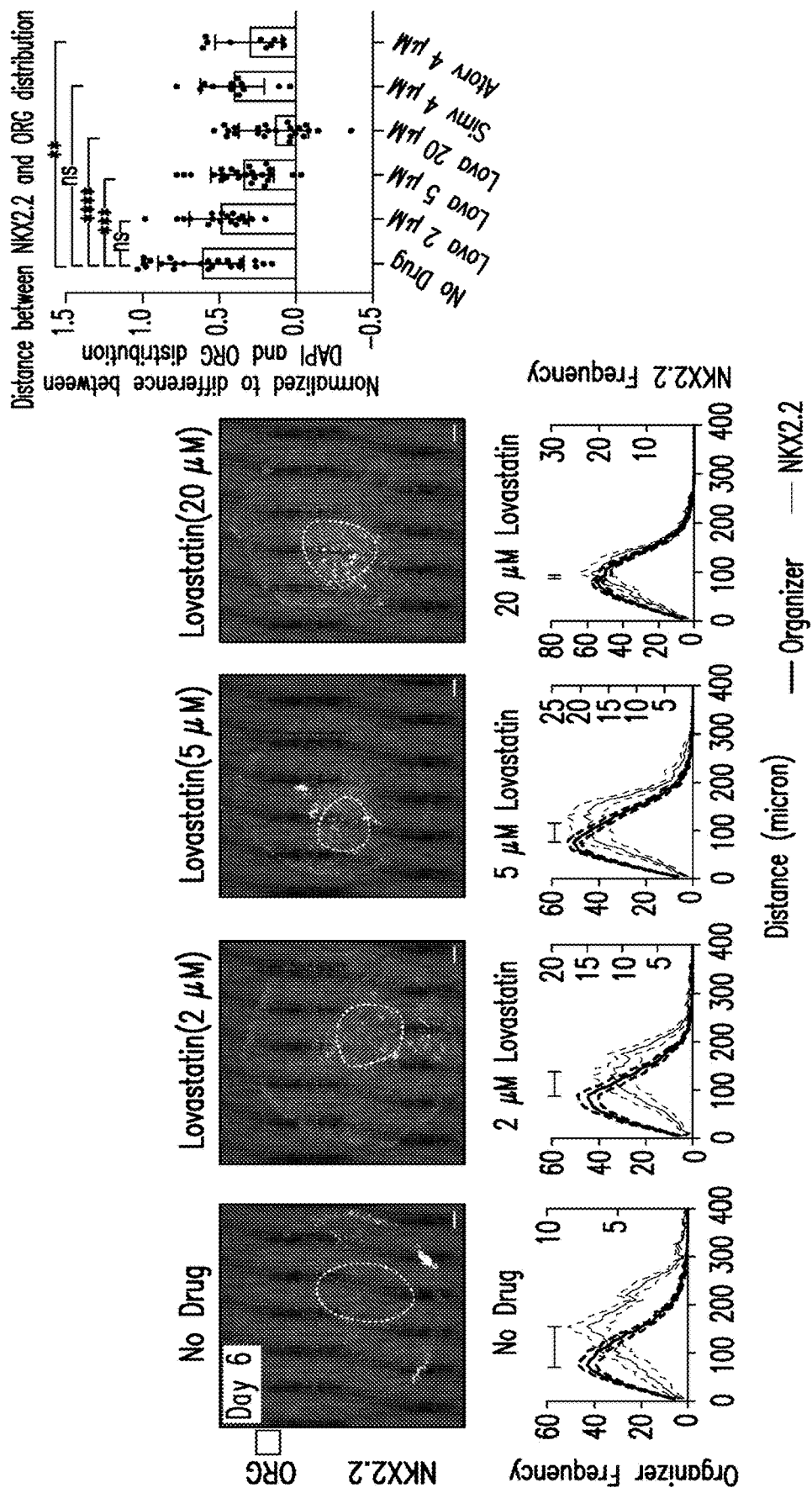
Figure 29A:
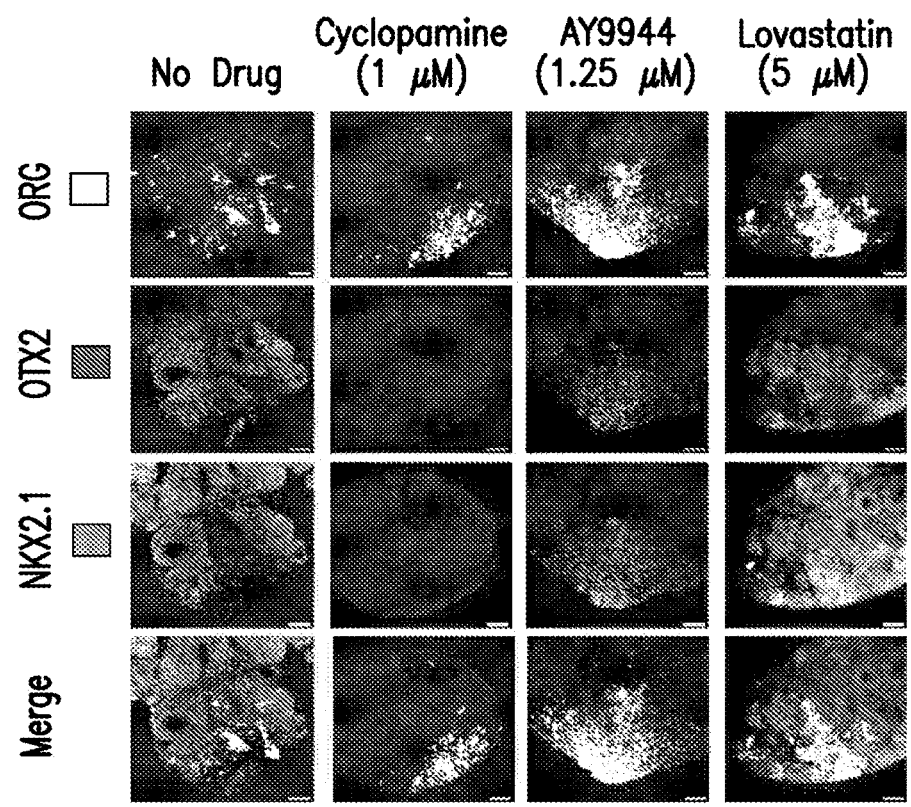
Figure 29B:
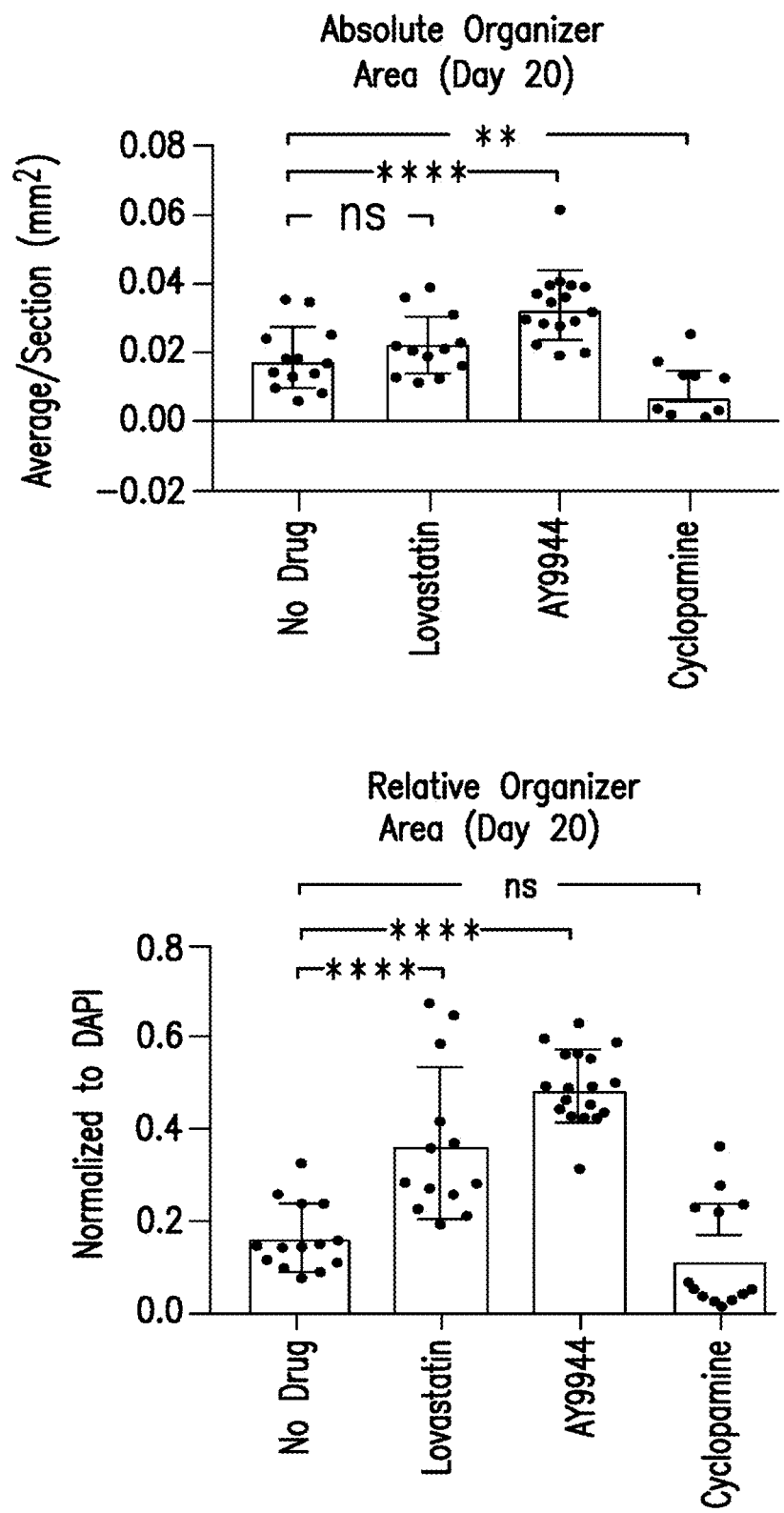
Figure 29C:
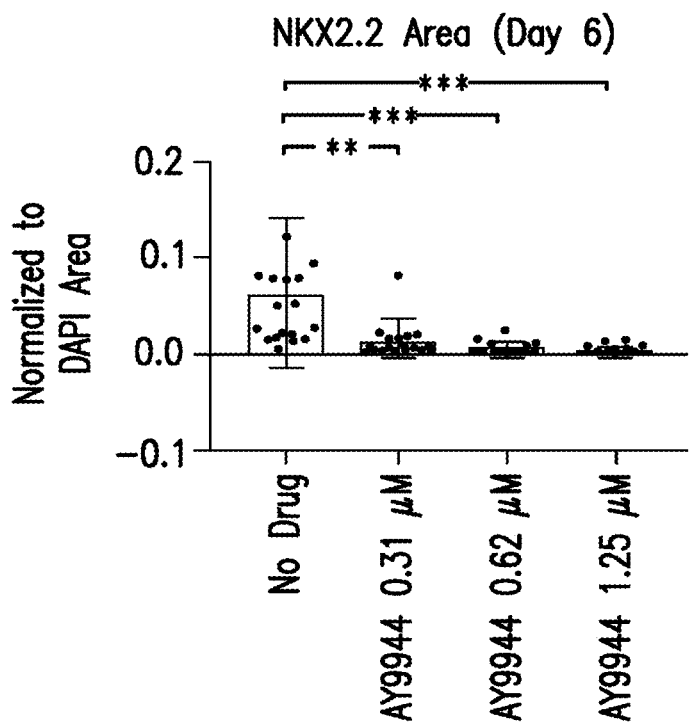
Figure 29D:
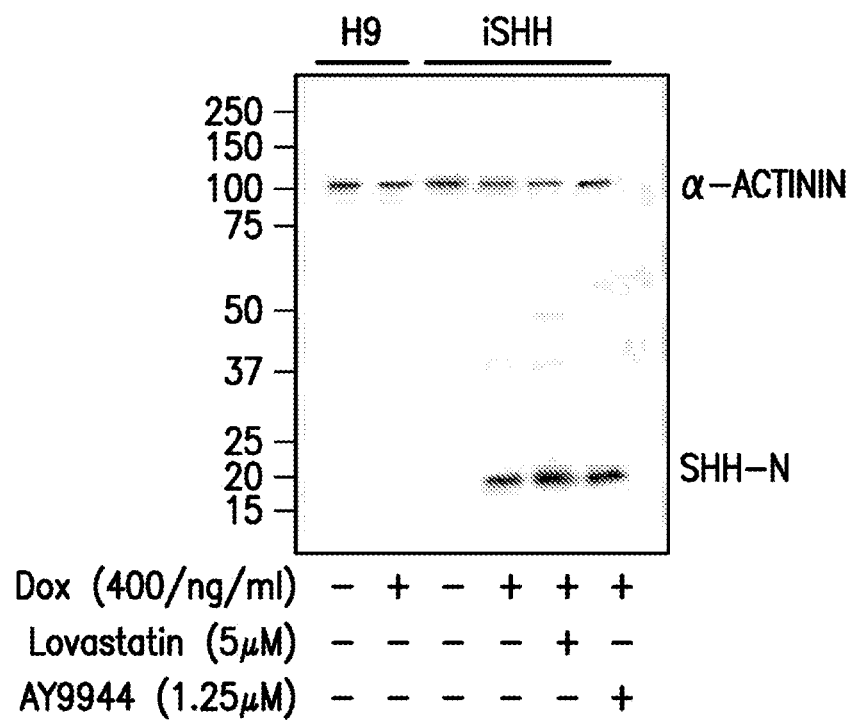

In addition to the effects on patterning, the drugs affected organoid growth. Overall organoid size was reduced in all treatment conditions (FIGS. 22B-22C). However, AY9944 and Lovastatin did not reduce the size of the organizer itself (FIG. 29B), consistent with the interpretation that cholesterol synthesis-inhibition has differential effects on local and long-range SHH activity. To dissociate growth and patterning phenotypes, the present study analyzed organoids at day 6, during the early stages of SHH patterning, and prior to the major phase of tissue growth (which occurs after matrigel embedding). NKX2.2 was used, a direct target of GLI[56], as a read-out of SHH signaling activity. By measuring the distance at which NKX2.2 is expressed from the SHH producing cells, the distance of SHH signaling activity could be inferred. Lovastatin reduced the distance at which NKX2.2 is induced from the organizer in a dose-dependent manner (FIG. 22D). AY9944 strongly inhibited NKX2.2 induction at all concentrations tested (FIG. 29C). Neither AY9944 nor lovastatin grossly perturbed processing of SHH peptide length (FIG. 29D). Together, these data support a model in which inhibition of cholesterol synthesis by Lovastatin or AY9944 result in a complex developmental phenotype characterized by impaired growth and a reduction in the range of SHH signaling activity.

This study provided the first evidence that an asymmetric morphogenetic cue provided positional information from which in vivo-like topography could emerge in brain organoids. Furthermore, the present evidence showed that SHH used a long-range signaling mechanism during forebrain organoid development, recapitulating aspects of in vivo behavior[41]. The emergence of long-range activity in 3D that was not present in 2D cultures highlighted the importance of tissue geometry on the spatial dynamics of signaling activity.

The reproducibility and robustness of the present strategy allowed us to use SHH organoids as a developmental toxicology platform. Statins have been reported to be associated with fetal maldevelopment in a small number of cases[49]. The present data suggested that statins can impair forebrain development by degrading long-range SHH signaling and reducing tissue growth. These effects were observed in the present organoid system in the low micromolar range, which was significantly higher than the typical plasma concentration of statins (15-20 nM)[57]. However, levels during pregnancy in the developing nervous system of an embryo or fetus are not known and could be substantially higher for lipophilic statins. Furthermore, prenatal exposure to statin may only affect a subset of patients who harbor a genetic predisposition to holoprosencephaly[58], or who present with additional co-morbidities that allow statins to accumulate in fetal tissue[53,59,60]. The present data showed that cholesterol supports long-range SHH signaling[36], which may occur through the formation of soluble multimeric complexes[37] and by facilitating interactions with SHH-transport proteins essential for long-range activity[45,46].

A key feature of the patterning strategy presented here was the establishment of well-ordered positional domains during early organoid development. Manipulating soluble ECM components was a strategy to improve the maintenance of radially organized structures within organoids over time[61].

The present disclosure of establishment of forebrain topography in organoids enabled the study of a wide range of phenotypes in a single organoid system, for example, complex neurodevelopmental diseases that may alter or derive from regional specification during forebrain patterning, including autism[63], epilepsy[64], bi-polar disorder[65], or superstellar pediatric gliomas[66]. The present disclosed can be used as a general approach to establish topographies across all regions of the CNS beyond the forebrain. Establishing properly organized forebrain organoids, with the correct regional topography is an important step on the road of realizing the full potential of human "mini-brain" technology.

Methods hPSC Maintenance and Monolayer Differentiation hPSC (H9 and derivatives (EF1α::GFP (GFP), EF1α:: RFP; TRE-SHH (iSHH), MEL1, HUES6, HUES8, LHX6-citrine) and iPSC (J1 and 348) were maintained with Essential 8 medium or Essential 8 flex (E8, Thermo, A15117001 or A28558501) in feeder-free conditions on vitronectin (VTN-N) substrate (Thermo, A14700). hPSCs were passaged as clumps with EDTA solution (0.5 M EDTA/PBS). For neural monolayer differentiation, hPSCs were dissociated to single cells and plated on matrigel substrate (BD Biosciences, 354234) in E8 at a density of 250,000 cells/cm$^2$ in the presence of ROCK inhibitor (Y-27632, 10 mM, Tocris 1254) (Day -1). From Day 0 to 7, cells were cultured in Essential 6 medium (E6, Thermo, A1516401) in the presence of TGFb and BMP inhibitors (LDN193189, 100 nM, Stem Cell Technologies, 72142; SB431542, 10 mM, Tocris, 1614). From day 7 to 12, cells were cultured in E6 alone. Floorplate was specified by addition of SHH (200 ng/ml, R&D Systems 464-SH) and CHIR99021 (0.7 mM, Tocris 4423). Media was changed every day during the differentiation.

SHH Inducible Line

The iSHH hPSC was generated according to a previously described gene targeting strategy[21]. Briefly, two donor constructs were targeted to the first intron of the AAVS1 locus using TALEN-facilitated homologous recombination. One construct contained a constitutively expressed reverse tetracycline transactivator (M2rtTA) and the second construct contained a tetracycline inducible (TRE) SHH cassette. The SHH cassette was generated using full length human SHH cDNA (Genecopoeia T1004). Targeting was performed in a constitutive RFP expressing line (WA09 derived, EF1α:: RFP) so iSHH cells could be visualized[20].

SHH-Spheroid Aggregation 1,000 iSHH cells were dissociated to single cell and aggregated in low-attachment round bottom microwells for 24 hours in the presence of ROCK inhibitor (Y-27632, 10 mM) and WNT inhibitor (XAV939, 5 mM). For FIG. 21C, the GFP boundary was established by first plating iSHH cells and allowing them to aggregate for 8 hours. 1,000 GFP cells were then plated on top and allowed to aggregate overnight. The next day, 10,000 wildtype H9 hPSCs were dissociated to single cell and allowed to aggregate on top of the iSHH cells, in E8 medium with ROCK inhibitor (Y-27632, 10 mM) and WNT inhibitor (XAV939, 5 mM, Tocris 3748).

SHH Organoid Differentiation

SHH-spheroids were cultured in E6 with 3-inhibitors (LDN193189, 100 nM; SB431542, 10 mM; XAV939, 5 mM) plus doxycycline (400 ng/mL) until spheroid tissue began to brighten and have smooth edges, typically 6-8 days. SHH-spheroids were then embedded in matrigel drops and cultured in a N2/B27 based organoid media as previously described[3], except NeuroBrew B21 (Miltenyi Biotec) was substituted for B27. SHH-spheroids were moved an orbital shaker once formation of translucent, neuroepithelial buds was observed, typically 4-7 days after embedding. Organoids that failed to form translucent, neuroepithelial buds were discarded. Half media was changed every other day.

Histology and Immunocytochemistry

Day 20 organoids were fixed in 4% PFA overnight at 4° C. and washed three times with PBS the next day. After fixation, tissue was cryoprotected in 30% sucrose/PBS and sectioned at 30 mm on a cryostat (Leica 3050 S). Sections were blocked for 30 minutes in 10% FBS, 1% BSA, 0.3% triton in PBS, and incubated as floating section in primary antibody overnight. The next day, sections were washed with PBS and incubated as floating section in secondary antibody for 3 hours at room temperature. Day 6 organoids were fixed in 4% PFA for 2 hours at 4° C. and washed three times with PBS. After fixation, tissue was cryoprotected in 30% sucrose/PBS and sectioned at 20 mm and mounted directly onto slides prior to immunofluorescence assays.

Quantification of Organoid Patterning and SHH Activity

Organoid topography was quantified by first dividing each image into a grid of 20 mm×20 mm squares (day 20 analysis) or 5 mm×5 mm squares (day 6 analysis) that form a Cartesian coordinate grid. Each square is a discrete region of interest (ROI) that is associated with an X and Y coordinate. The origin of the grid was calculated for each image as the "center of mass" of the iSHH-organizer cells: $CM_x = \Sigma m_i x_i/M$ and $CM_y = \Sigma m_i y_i/M$, where m=grey value intensity of iSHH cells for individual ROIs, x or y=coordinate, and M=total intensity for all ROIs, and the sum includes all x or y coordinates in the image. Next, ROI's that were positive for expression of a given protein (e.g. PAX6) were defined by thresholding staining intensity and determining ROIs with positive immunoreactivity. The linear distance from the origin to each ROI ($sqrt((ROI_x - CM_x)^2 + (ROI_y - CM_y)^2)$) was calculated. The present study analyzed every sixth section for each regional marker per organoid (typically 2-5 sections/organoid, depending on organoid size), thus sampling the organoids in 150 μm intervals using uniform random sampling.

In FIGS. 20C and 22D ROI frequencies were plotted as a function of distance from the center of mass. In FIG. 21C the GFP shell distance is defined as the radial distance from the center of mass at which the ratio of GFP ROIs/DAPI ROIs drops below 35%. The SHH-activity distance is the radial distance from the center of mass to the edge of the PAX6-negative territory, defined as the distance at which the ratio of PAX6-negative ROIs/DAPI ROIs dropped below 95% (PAX6-negative ROIs were obtained by subtracting PAX6 thresholded pixels from DAPI thresholded pixels). The 35% and 95% parameters were determined prior to analysis as accurately cut off values by comparing with manual distance measurements. Sections that lacked organizer cells or that had large necrotic centers were excluded from analysis. Area measurements in FIG. 22B are determined by calculating the number of positive ROIs positive for a given gene (e.g. PAX6) divided by the ROIs positive for DAPI.

The distance of SHH patterning activity in FIG. 21A was obtained by measuring the distance of lines from the edge of PAX6 territory to the nearest organizer cells. At least 5 lines were measured per section. All quantifications were performed using ImageJ.

Microscopy was performed using a standard inverted epifluorescence microscope (Olympus IX71 or Zeiss Axio Observer). Images were acquired using Cell Sens (Olympus) or Zen Pro (Zeiss) software. Min, max and gamma (midtone) adjustments were applied uniformly to images during processing with Adobe Photoshop Creative Cloud.

RNA Extraction and RT-PCR

RNA was extracted using TRIzol (Invitrogen, 15596026) followed by chloroform extraction. RNA was precipitated in isopropanol and resuspended in nuclease free ddH2O. cDNA synthesis was performed using 1 mg of RNA (iScript, Bio-Rad, 1708840). RT-PCR was performed with EvaGreen Supermix (Bio-Rad, 1725202). Three to four individual samples were combined into a single replicate when collecting RNA from spheroids.

Visualization of SHH Protein Gradient

SHH-spheroids were fixed in 4% PFA for 6 hours at 4C, then washed three times in PBS. Standard immunocytochemistry was performed on wholemount SHH-spheroids using anti-SHH primary antibody (1:100, clone 5E1, DSHB). Secondary antibody was amplified using a tyramide signal amplification kit (Thermo, B40941). Fluorescence labeled spheroids were visualized using an inverted epifluorescence microscope. Gradients were quantified using line scans that transected the organizer tissue. Quantifications were performed using ImageJ.

Cell-Based SHH Palmitoylation Assay

Synthesis of [$I^{125}$]iodopalmitate was carried out as previously described[67-69]. iSHH hPSCs were dissociated to single cell and seeded as a confluent monolayer on matrigel substrate at a density of 250,000 cells/cm$^2$ and differentiated for 9 days in E6 with LDN193189, (100 nM) and SB431542 (10 mM) at increasing concentrations of doxycycline (0, 125, 250, 500, 1000, 2000 ng/ml). On day 9, iSHH cells were incubated for 1 h at 37° C. with DMEM containing 2% dialyzed FBS and then labeled for 4 h with 10 μCi of [$I^{125}$] iodopalmitate. The cells were lysed and subjected to immunoprecipitation with an anti-SHH antibody, and the immunoprecipitates were diluted in 100 μl of 2×SDS-PAGE sample buffer containing 10 mM DTT. The samples were analyzed on a 12.5% SDS-PAGE gel, followed by phosphorimaging on a Typhoon FLA-7000 phosphorimager. An aliquot of each immunoprecipitate was analyzed for SHH protein expression by Western blotting.

SHH Western Blot

Cells were harvested and washed with PBS. Cell pellets were lysed in RIPA buffer (Boston Bioproducts Inc. NC9517624) supplemented with protease inhibitors (Thermo 78425) and ran through a syringe several times. Lysate was incubated for 30 minutes on ice and then centrifuged to isolate the supernatant. For quantification of protein concentration, 3 ul of lysate was added to 300 ul of Precision Red (Cytoskeleton, Inc. ADV02-A) and absorbance (600 nm) was read on a plate reader and the concentration was calculated by: $(Abs^{sample} - Abs^{background}) \times 12.5$. For Western blots, 10 mg of protein was resuspended in 2X Laemmli buffer and denatured at 100 C for 5 minutes. Samples were loaded and run on a 4-12% pre-cast Bis-Tris gel (Thermo NP0322BOX) and transferred overnight onto Nitrocellulose membrane (Thermo 88018). Membranes were blocked in 5% milk and primary antibodies were incubated overnight at 4C. Blots were visualized using ECL (Perkin Elmer NEL104001EA).

Statistical Analysis

All reported measurements are from distinct samples. When comparing samples across treatment groups, samples were collected, processed, and analyzed in parallel. In the figure legends, "n" refers to an independent biological replicate (e.g. single organoid or single monolayer culture). "Organoid" refers to an individual, distinct organoid from 1 well of culture dish. "Batch" refers to a group of organoids that were differentiated in the same dish on the same day. Statistical tests are listed in the figure legends.

7. REFERENCES

1 Kelava, I. & Lancaster, M. A. Stem Cell Models of Human Brain Development. *Cell Stem Cell* 18, 736-748, doi:10.1016/j.stem.2016.05.022 (2016).
2 Sasai, Y., Eiraku, M. & Suga, H. In vitro organogenesis in three dimensions: self-organising stem cells. *Development* 139, 4111-4121, doi:10.1242/dev.079590 (2012).
3 Lancaster, M. A. & Knoblich, J. A. Organogenesis in a dish: modeling development and disease using organoid technologies. *Science* 345, 1247125, doi:10.1126/science.1247125 (2014).
4 Lancaster, M. A. et al. Cerebral organoids model human brain development and microcephaly. *Nature* 501, 373-379, doi:10.1038/nature12517 (2013).
5 Quadrato, G., Brown, J. & Arlotta, P. The promises and challenges of human brain organoids as models of neuropsychiatric disease. *Nat Med* 22, 1220-1228, doi: 10.1038/nm.4214 (2016).
6 Renner, M. et al. Self-organized developmental patterning and differentiation in cerebral organoids. *EMBO J* 36, 1316-1329, doi:10.15252/embj.201694700 (2017).
7 O'Leary, D. D., Chou, S. J. & Sahara, S. Area patterning of the mammalian cortex. *Neuron* 56, 252-269, doi:10.1016/j.neuron.2007.10.010 (2007).
8 Sagner, A. & Briscoe, J. Morphogen interpretation: concentration, time, competence, and signaling dynamics. *Wiley Interdiscip Rev Dev Biol* 6, doi:10.1002/wdev.271 (2017).
9 Eiraku, M. et al. Self-organizing optic-cup morphogenesis in three-dimensional culture. *Nature* 472, 51-56, doi: 10.1038/nature09941 (2011).
10 Suga, H. et al. Self-formation of functional adenohypophysis in three-dimensional culture. *Nature* 480, 57-62, doi:10.1038/nature10637 (2011).
11 Kadoshima, T. et al. Self-organization of axial polarity, inside-out layer pattern, and species-specific progenitor dynamics in human ES cell-derived neocortex. *Proc Natl Acad Sci USA* 110, 20284-20289, doi:10.1073/pnas.1315710110 (2013).
12 Jo, J. et al. Midbrain-like Organoids from Human Pluripotent Stem Cells Contain Functional Dopaminergic and Neuromelanin-Producing Neurons. *Cell Stem Cell* 19, 248-257, doi:10.1016/j.stem.2016.07.005 (2016).
13 Muguruma, K., Nishiyama, A., Kawakami, H., Hashimoto, K. & Sasai, Y. Self-organization of polarized cerebellar tissue in 3D culture of human pluripotent stem cells. *Cell Rep* 10, 537-550, doi:10.1016/j.celrep.2014.12.051 (2015).
14 Qian, X. et al. Brain-Region-Specific Organoids Using Mini-bioreactors for Modeling
ZIKV Exposure. *Cell* 165, 1238-1254, doi:10.1016/j.cell.2016.04.032 (2016).
15 Bagley, J. A., Reumann, D., Bian, S., Levi-Strauss, J. & Knoblich, J. A. Fused cerebral organoids model interactions between brain regions. *Nat Methods* 14, 743-751, doi:10.1038/nmeth.4304 (2017).
16 Birey, F. et al. Assembly of functionally integrated human forebrain spheroids. *Nature* 545, 54-59, doi:10.1038/nature22330 (2017).
17 Xiang, Y. et al. Fusion of Regionally Specified hPSC-Derived Organoids Models Human Brain Development and Interneuron Migration. *Cell Stem Cell* 21, 383-398 e387, doi:10.1016/j.stem.2017.07.007 (2017).
18 Jessell, T. M. Neuronal specification in the spinal cord: inductive signals and transcriptional codes. *Nat Rev Genet* 1, 20-29, doi:10.1038/35049541 (2000).
19 Lupo, G., Harris, W. A. & Lewis, K. E. Mechanisms of ventral patterning in the vertebrate nervous system. *Nat Rev Neurosci* 7, 103-114, doi:10.1038/nrn1843 (2006).
20 Fattahi, F. et al. Deriving human ENS lineages for cell therapy and drug discovery in Hirschsprung disease. *Nature* 531, 105-109, doi:10.1038/nature16951 (2016).
21 Gonzalez, F. et al. An iCRISPR platform for rapid, multiplexable, and inducible genome editing in human pluripotent stem cells. *Cell Stem Cell* 15, 215-226, doi: 10.1016/j.stem.2014.05.018 (2014).
22 Lancaster, M. A. & Knoblich, J. A. Generation of cerebral organoids from human pluripotent stem cells. *Nat Protoc* 9, 2329-2340, doi:10.1038/nprot.2014.158 (2014).
23 Shiraishi, A., Muguruma, K. & Sasai, Y. Generation of thalamic neurons from mouse embryonic stem cells. *Development* 144, 1211-1220, doi:10.1242/dev.144071 (2017).
24 Merchan, P., Bardet, S. M., Puelles, L. & Ferran, J. L. Comparison of Pretectal Genoarchitectonic Pattern between Quail and Chicken Embryos. *Front Neuroanat* 5, 23, doi:10.3389/fnana.2011.00023 (2011).
25 Oliver, G. et al. Six3, a murine homologue of the sine oculis gene, demarcates the most anterior border of the developing neural plate and is expressed during eye development. *Development* 121, 4045-4055 (1995).
26 Niida, A. et al. DKK1, a negative regulator of Wnt signaling, is a target of the beta-catenin/TCF pathway. *Oncogene* 23, 8520-8526, doi:10.1038/sj.onc.1207892 (2004).
27 Shinya, M., Eschbach, C., Clark, M., Lehrach, H. & Furutani-Seiki, M. Zebrafish Dkk1, induced by the pre-MBT Wnt signaling, is secreted from the prechordal plate and patterns the anterior neural plate. *Mech Dev* 98, 3-17 (2000).
28 Kiecker, C. & Niehrs, C. A morphogen gradient of Wnt/beta-catenin signalling regulates anteroposterior neural patterning in Xenopus. *Development* 128, 4189-4201 (2001).
29 Houart, C. et al. Establishment of the telencephalon during gastrulation by local antagonism of Wnt signaling. *Neuron* 35, 255-265 (2002).
30 Maroof, A. M. et al. Directed differentiation and functional maturation of cortical interneurons from human embryonic stem cells. *Cell Stem Cell* 12, 559-572, doi: 10.1016/j.stem.2013.04.008 (2013).
31 Blaess, S., Szabo, N., Haddad-Tovolli, R., Zhou, X. & Alvarez-Bolado, G. Sonic hedgehog signaling in the development of the mouse hypothalamus. *Front Neuroanat* 8, 156, doi:10.3389/fnana.2014.00156 (2014).
32 Merkle, F. T. et al. Generation of neuropeptidergic hypothalamic neurons from human pluripotent stem cells. *Development* 142, 633-643, doi:10.1242/dev.117978 (2015).
33 Briscoe, J., Chen, Y., Jessell, T. M. & Struhl, G. A hedgehog-insensitive form of patched provides evidence for direct long-range morphogen activity of sonic hedgehog in the neural tube. *Mol Cell* 7, 1279-1291 (2001).
34 Honig, L. S. Positional signal transmission in the developing chick limb. *Nature* 291, 72-73 (1981).

35 Fan, C. M. & Tessier-Lavigne, M. Patterning of mammalian somites by surface ectoderm and notochord: evidence for sclerotome induction by a hedgehog homolog. *Cell* 79, 1175-1186 (1994).

36 Lewis, P. M. et al. Cholesterol modification of sonic hedgehog is required for long-range signaling activity and effective modulation of signaling by Ptc1. *Cell* 105, 599-612 (2001).

37 Zeng, X. et al. A freely diffusible form of Sonic hedgehog mediates long-range signalling. *Nature* 411, 716-720, doi:10.1038/35079648 (2001).

38 Chen, M. H., Li, Y. J., Kawakami, T., Xu, S. M. & Chuang, P. T. Palmitoylation is required for the production of a soluble multimeric Hedgehog protein complex and long-range signaling in vertebrates. *Genes Dev* 18, 641-659, doi:10.1101/gad.1185804 (2004).

39 Sanders, T. A., Llagostera, E. & Barna, M. Specialized filopodia direct long-range transport of SHH during vertebrate tissue patterning. *Nature* 497, 628-632, doi: 10.1038/nature12157 (2013).

40 Harfe, B. D. et al. Evidence for an expansion-based temporal Shh gradient in specifying vertebrate digit identities. *Cell* 118, 517-528, doi:10.1016/j.cell.2004.07.024 (2004).

41 McGlinn, E. & Tabin, C. J. Mechanistic insight into how Shh patterns the vertebrate limb. *Curr Opin Genet Dev* 16, 426-432, doi:10.1016/j.gde.2006.06.013 (2006).

42 Zhang, Y. & Alvarez-Bolado, G. Differential developmental strategies by Sonic hedgehog in thalamus and hypothalamus. *J Chem Neuroanat* 75, 20-27, doi:10.1016/j.jchemneu.2015.11.008 (2016).

43 Ericson, J. et al. Sonic hedgehog induces the differentiation of ventral forebrain neurons: a common signal for ventral patterning within the neural tube. *Cell* 81, 747-756 (1995).

44 Tian, H., Jeong, J., Harfe, B. D., Tabin, C. J. & McMahon, A. P. Mouse Disp1 is required in sonic hedgehog-expressing cells for paracrine activity of the cholesterol-modified ligand. *Development* 132, 133-142, doi:10.1242/dev.01563 (2005).

45 Creanga, A. et al. Scube/You activity mediates release of dually lipid-modified Hedgehog signal in soluble form. *Genes Dev* 26, 1312-1325, doi:10.1101/gad.191866.112 (2012).

46 Tukachinsky, H., Kuzmickas, R. P., Jao, C. Y., Liu, J. & Salic, A. Dispatched and scube mediate the efficient secretion of the cholesterol-modified hedgehog ligand. *Cell Rep* 2, 308-320, doi:10.1016/j.celrep.2012.07.010 (2012).

47 Byrne, E. F. X. et al. Structural basis of Smoothened regulation by its extracellular domains. *Nature* 535, 517-522, doi:10.1038/nature18934 (2016).

48 Huang, P. et al. Cellular Cholesterol Directly Activates Smoothened in Hedgehog Signaling. *Cell* 166, 1176-1187 e1114, doi:10.1016/j.cell.2016.08.003 (2016).

49 Edison, R. J. & Muenke, M. Central nervous system and limb anomalies in case reports of first-trimester statin exposure. *N Engl J Med* 350, 1579-1582, doi:10.1056/NEJM200404083501524 (2004).

50 Taguchi, N. et al. Prenatal exposure to HMG-CoA reductase inhibitors: effects on fetal and neonatal outcomes. *Reprod Toxicol* 26, 175-177, doi:10.1016/j.reprotox.2008.06.009 (2008).

51 Kazmin, A., Garcia-Bournissen, F. & Koren, G. Risks of statin use during pregnancy: a systematic review. *J Obstet Gynaecol Can* 29, 906-908, doi:10.1016/S1701-2163(16)32656-1 (2007).

52 Winterfeld, U. et al. Pregnancy outcome following maternal exposure to statins: a multicentre prospective study. *BJOG* 120, 463-471, doi:10.1111/1471-0528.12066 (2013).

53 Edison, R. J. & Muenke, M. Mechanistic and epidemiologic considerations in the evaluation of adverse birth outcomes following gestational exposure to statins. *Am J Med Genet A* 131, 287-298, doi:10.1002/ajmg.a.30386 (2004).

54 Blassberg, R., Macrae, J. I., Briscoe, J. & Jacob, J. Reduced cholesterol levels impair Smoothened activation in Smith-Lemli-Opitz syndrome. *Hum Mol Genet* 25, 693-705, doi:10.1093/hmg/ddv507 (2016).

55 Gaspard, N. et al. An intrinsic mechanism of corticogenesis from embryonic stem cells. *Nature* 455, 351-357, doi:10.1038/nature07287 (2008).

56 Lei, Q. et al. Wnt signaling inhibitors regulate the transcriptional response to morphogenetic Shh-Gli signaling in the neural tube. *Dev Cell* 11, 325-337, doi:10.1016/j.devcel.2006.06.013 (2006).

57 Bellosta, S., Paoletti, R. & Corsini, A. Safety of statins: focus on clinical pharmacokinetics and drug interactions. *Circulation* 109, III50-57, doi:10.1161/01.CIR.0000131519.15067.1f (2004).

58 Hong, M. et al. BOC is a modifier gene in holoprosencephaly. *Hum Mutat* 38, 1464-1470, doi:10.1002/humu.23286 (2017).

59 Briscoe, J. & Therond, P. P. The mechanisms of Hedgehog signalling and its roles in development and disease. *Nat Rev Mol Cell Biol* 14, 416-429, doi:10.1038/nrm3598 (2013).

60 Guerrero, I. & Chiang, C. A conserved mechanism of Hedgehog gradient formation by lipid modifications. *Trends Cell Biol* 17, 1-5, doi:10.1016/j.tcb.2006.11.002 (2007).

61 Lancaster, M. A. et al. Guided self-organization and cortical plate formation in human brain organoids. *Nat Biotechnol* 35, 659-666, doi:10.1038/nbt.3906 (2017).

62 Di Lullo, E. & Kriegstein, A. R. The use of brain organoids to investigate neural development and disease. *Nat Rev Neurosci* 18, 573-584, doi:10.1038/nrn.2017.107 (2017).

63 Mariani, J. et al. FOXG1-Dependent Dysregulation of GABA/Glutamate Neuron Differentiation in Autism Spectrum Disorders. *Cell* 162, 375-390, doi:10.1016/j.cell.2015.06.034 (2015).

64 Cobos, I. et al. Mice lacking Dlx1 show subtype-specific loss of interneurons, reduced inhibition and epilepsy. *Nat Neurosci* 8, 1059-1068, doi:10.1038/nn1499 (2005).

65 Chen, H. M. et al. Transcripts involved in calcium signaling and telencephalic neuronal fate are altered in induced pluripotent stem cells from bipolar disorder patients. *Transl Psychiatry* 4, e375, doi:10.1038/tp.2014.12 (2014).

66 Fontebasso, A. M. et al. Recurrent somatic mutations in ACVR1 in pediatric midline high-grade astrocytoma. *Nat Genet* 46, 462-466, doi:10.1038/ng.2950 (2014).

67 Buglino, J. A. & Resh, M. D. Hhat is a palmitoylacyltransferase with specificity for N-palmitoylation of Sonic Hedgehog. *J Biol Chem* 283, 22076-22088, doi:10.1074/jbc.M803901200 (2008).

68 Berthiaume, L., Peseckis, S. M. & Resh, M. D. Synthesis and use of iodo-fatty acid analogs. *Methods Enzymol* 250, 454-466 (1995).

69 Alland, L., Peseckis, S. M., Atherton, R. E., Berthiaume, L. & Resh, M. D. Dual myristylation and palmitylation of Src family member p59fyn affects subcellular localization. *J Biol Chem* 269, 16701-16705 (1994).
70. Lancaster et al. Cerebral organoids model human brain development and microcephaly. Nature. 2013; 501(7467): 373-9. doi: 10.1038/nature12517. Epub 2013 Aug. 28.
71. Bagley et a. Fused cerebral organoids model interactions between brain regions. Nat Methods. 2017; 14(7):743-751. doi: 10.1038/nmeth.4304. Epub 2017 May 10.
72. Three dimensional heterogeneously differentiated tissue culture (EP2743345 A1)
73. Paşca et al. Functional cortical neurons and astrocytes from human pluripotent stem cells in 3D culture. Nat Methods. 2015; 12(7):671-8. doi: 10.1038/nmeth.3415. Epub 2015 May 25.
74. Nature. 2017 May 4; 545(7652):54-59. doi: 10.1038/nature22330. Epub 2017 Apr. 26. Assembly of functionally integrated human forebrain spheroids. Birey F1, Andersen J1, Makinson CD2, Islam S3, Wei W3,4, Huber N1, Fan HC5, Metzler KRC5, Panagiotakos G6, Thom N1, O'Rourke NA1, Steinmetz LM3,4,7, Bernstein JAB, Hallmayer J1, Huguenard JR2, Paca SP1.
75. Kadoshima et al. Self-organization of axial polarity, inside-out layer pattern, and species-specific progenitor dynamics in human ES cell-derived neocortex. Proc Natl Acad Sci USA. 2013 Dec. 10; 110(50):20284-9. doi: 10.1073/pnas.1315710110. Epub 2013 Nov. 25.
76. Method for manufacturing telencephalon or progenitor tissue thereof (PCT/JP2014/080966)
77. Qian et al. Brain-Region-Specific Organoids Using Mini-bioreactors for Modeling ZIKV Exposure. Cell. 2016 May 19; 165(5):1238-54. doi: 10.1016/j.cell.2016.04.032. Epub 2016 Apr. 22.
79. Spin Ω-13 A Multi-well Bioreactor for Culturing 3D Organoid (PCT/US2016/061610)

Although the presently disclosed subject matter and its advantages have been described in detail, it should be understood that various changes, substitutions and alterations can be made herein without departing from the spirit and scope of the invention. Moreover, the scope of the present application is not intended to be limited to the particular embodiments of the process, machine, manufacture, and composition of matter, means, methods and steps described in the specification. As one of ordinary skill in the art will readily appreciate from the invention of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Various patents, patent applications, publications, product descriptions, protocols, and sequence accession numbers are cited throughout this application, the inventions of which are incorporated herein by reference in their entireties for all purposes.

What is claimed is:

1. A method of producing a topographically organized brain organoid, comprising:
   (i) providing an organizer that is a source of a diffusible organizing agent;
   (ii) placing the organizer in apposition to an aggregate of undifferentiated or partially differentiated stem cells to form an organizer/aggregate complex;
   (iii) contacting the organizer/aggregate complex with at least one inhibitor selected from the group consisting of bone morphogenetic protein (BMP) inhibitors, transforming growth factor beta (TGFβ)/Activin-Nodal inhibitors, and Wingless (Wnt) inhibitors for at least 1 day; and
   (iv) culturing the organizer/aggregate complex in vitro for at least 20 days to form the topographically organized brain organoid;
   wherein the organizer comprises one or more genetically modified cells that express the organizing agent or one or more beads that release the organizing agent;
   wherein the organizer releases the organizing agent to form a gradient concentration of the organizing agent effective in generating cells, in the organoid, having different phenotypes at different distances from the organizer for at least 10 days;
   wherein the organizing agent is selected from the group consisting of SHH signaling agonists, molecules that induce SHH protein expression, molecules that promote SHH activity, and a combination thereof;
   wherein the stem cells are selected from the group consisting of embryonic stem cells (ESCs), induced pluripotent stem cells (iPSCs), and a combination thereof;
   wherein said brain organoid comprises:
   (i) a cortex-like region comprising cells expressing FOXG1 and/or PAX6;
   (ii) a lateral ganglionic eminence (LGE)-like region comprising cells expressing GSH2 and contiguous to a region expressing PAX6;
   (iii) a medial ganglionic eminence (MGE)-like region comprising cells expressing NKX2.1 and FOXG1;
   (iv) a hypothalamus-like region comprising cells expressing NKX2.2 and NKX2.1;
   (v) an anterior hypothalamic-like region comprising cells expressing NKX2.2; and
   (vi) a ventro-posterior hypothalamic-like region comprising cells expressing NKX2.1 but not FOXG1.

2. The method of claim 1, wherein the at least one inhibitor promotes the formation of forebrain tissue.

3. The method of claim 1, wherein (iii) further comprises contacting the organizer/aggregate complex with at least one BMP inhibitor, at least one TGFβ/Activin-Nodal inhibitor, and at least one Wnt inhibitor.

4. The method of claim 3, further comprising contacting the organizer/aggregate complex with the at least one BMP inhibitor, the at least one TGFβ/Activin-Nodal inhibitor, and the at least one Wnt inhibitor concurrently.

5. The method of claim 1, wherein the organizer/aggregate complex is contacted with the at least one inhibitor for up to about 6, about 7, or about 8 days.

6. The method of claim 1, wherein the at least one BMP inhibitor comprises LDN193189, and/or the at least one TGFβ/Activin-Nodal inhibitor comprises SB431542, and/or the at least one Wnt inhibitor comprises XAV939.

7. The method of claim 1, wherein the stem cells are human stem cells.

8. The method of claim 1, wherein the genetically modified cells are selected from the group consisting of ESCs, iPSCs, and a combination thereof.

9. The method of claim 8, wherein the organizing agent is inducibly expressed or conditionally expressed.

10. The method of claim 1, wherein the organizing agent is a Sonic Hedgehog Protein (SHH), optionally the SHH is a human SHH (hSHH).

11. A method of producing a topically organized brain organoid comprising:
   (i) providing an organizer comprised of human stem cells engineered to express a hSHH;
   (ii) placing the organizer in apposition to an aggregate of undifferentiated or partially differentiated pluripotent human stem cells to form an organizer/aggregate complex, wherein the aggregate has a spheroid shape;
   (iii) contacting the organizer/aggregate complex with at least one inhibitor selected from the group consisting of bone morphogenetic protein (BMP) inhibitors, transforming growth factor beta (TGFβ)/Activin-Nodal inhibitors, and Wingless (Wnt) inhibitors for at least 1 day; and
   (iv) culturing the organizer/aggregate complex in vitro for at least 20 days to form the topographically organized brain organoid;
   wherein the organizer releases the hSHH to form a gradient concentration of the hSHH effective in generating the brain organoid comprising at least distinct forebrain and posterior regions for at least 10 days;
   wherein the human stem cells are selected from the group consisting of ESCs, iPSCs, and a combination thereof, wherein said brain organoid comprises:
   (i) a cortex-like region comprising cells expressing FOXG1 and/or PAX6;
   (ii) a lateral ganglionic eminence (LGE)-like region comprising cells expressing GSH2 and contiguous to a region expressing PAX6;
   (iii) a medial ganglionic eminence (MGE)-like region comprising cells expressing NKX2.1 and FOXG1;
   (iv) a hypothalamus-like region comprising cells expressing NKX2.2 and NKX2.1;
   (v) an anterior hypothalamic-like region comprising cells expressing NKX2.2; and
   (vi) a ventro-posterior hypothalamic-like region comprising cells expressing NKX2.1 but not FOXG1.

12. The method of claim 11, wherein the at least one inhibitor promotes the formation of forebrain tissues.

13. The method of claim 11, wherein (iii) further comprises contacting the organizer/aggregate complex with the at least one BMP inhibitor, the at least one TGFβ/Activin-Nodal inhibitor, and the at least one Wnt inhibitor.

14. The method of claim 13, further comprising contacting the organizer/aggregate complex with the at least one BMP inhibitor, the at least one TGFβ/Activin-Nodal inhibitor, and the at least one Wnt inhibitor concurrently.

15. The method of claim 11, wherein the organizer/aggregate complex is contacted with the at least one inhibitor for up to about 6, about 7, or about 8 days.

16. The method of claim 11, wherein the at least one BMP inhibitor comprises LDN193189, and/or at least one TGFβ/Activin-Nodal inhibitor comprises SB431542, and/or the at least one Wnt inhibitor comprises XAV939.

17. The method of claim 11, wherein the hSHH is inducibly expressed or conditionally expressed.

* * * * *